United States Patent [19]

Brown et al.

[11] Patent Number: 5,010,098

[45] Date of Patent: Apr. 23, 1991

[54] ARYLPYRROLE INSECTICIDAL ACARICIDAL AND NEMATICIDAL AGENTS AND METHODS FOR THE PREPARATION THEREOF

[75] Inventors: Dale G. Brown, Hunterdon; Jack K. Siddens, Princeton Junction; Robert E. Diehl, Lawrenceville; Donald P. Wright, Jr., Pennington, all of N.J.

[73] Assignee: American Cyanamid Company, Stamford, Conn.

[21] Appl. No.: 208,841

[22] Filed: Jun. 23, 1988

Related U.S. Application Data

[63] Continuation-in-part of Ser. No. 79,545, Jul. 29, 1987, abandoned.

[51] Int. Cl.$^5$ ............................................. A01N 43/36
[52] U.S. Cl. .................................... 514/426; 514/422; 514/423; 514/424; 514/427
[58] Field of Search ............... 514/422, 423, 426, 427, 514/424

[56] References Cited

U.S. PATENT DOCUMENTS

| | | | |
|---|---|---|---|
| 3,428,648 | 2/1969 | Umio et al. | 260/313.1 |
| 3,864,491 | 4/1975 | Bailey | 71/66 |
| 3,963,746 | 6/1976 | Bailey | 260/326.5 |
| 4,495,358 | 1/1985 | Koyama et al. | 548/550 |
| 4,563,472 | 1/1986 | Inouye et al. | 514/381 |
| 4,647,576 | 3/1987 | Hoefle et al. | 514/422 |
| 4,705,801 | 11/1987 | Martin et al. | 514/423 |
| 4,798,901 | 1/1989 | Tessier et al. | 548/561 |

FOREIGN PATENT DOCUMENTS

| | | |
|---|---|---|
| EP0130149 | 1/1985 | European Pat. Off. . |
| EP0206523 | 12/1986 | European Pat. Off. . |
| EP0300688 | 1/1989 | European Pat. Off. . |
| 44-001528-B | 1/1969 | Japan . |
| 62-098562-A | 5/1987 | Japan . |
| 2111985 | 7/1983 | United Kingdom . |

OTHER PUBLICATIONS

Van Leusen et al., Tetrahedron Letters, 52, 5337–5340 (1972).
Tsuge et al., J. Org. Chem., 52, 2523–2530 (1987).
Benages et al., J. Org. Chem., 43, 4273–4276.

*Primary Examiner*—Allen J. Robinson
*Attorney, Agent, or Firm*—Alice C. Brennan

[57] ABSTRACT

This invention is directed to certain novel insecticidal, acaricidal and nematicidal arylpyrrole agents and a method for controlling insects, acarids and nematodes therewith. The invention also is directed to a method for protecting growing plants from insect, acarid and nematode attack by applying to said plants or the soil in which they are growing, an insecticidally, acaricidally or nematicidally effective amount of a novel arylpyrrole compound. The present invention further is directed to a method for the preparation of the arylpyrrole compounds.

6 Claims, No Drawings

ARYLPYRROLE INSECTICIDAL ACARICIDAL AND NEMATICIDAL AGENTS AND METHODS FOR THE PREPARATION THEREOF

This application is a continuation-in-part of application, Ser. No. 079,545, filed July 29, 1987, now abandoned.

BACKGROUND OF THE INVENTION

Although there is a substantial body of literature which deals with a variety of natural and synthetic pyrroles as antibacterial and antifungal agents, the arylpyrroles of the present invention and the insecticidal activity associated therewith are distinct from the art.

Fujisawa Pharmaceutical's work with the antifungal agent pyrrolnitrin (structure shown below) was disclosed in U.S. Pat. No. 3,428,648. However, the Fujisawa structures are distinct from the compounds of the present invention, and there is no reference to insecticidal activity.

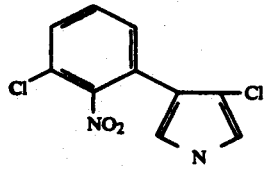

Pyrrolnitrin

Certain pyrrolomycins including antibiotic SS46506A recently isolated and identified by Meiji Seika Kaisha scientists are illustrated below. The antibiotic pyrrolomycin E contains only one pyrrole ring halogen atom. While antibiotic SS46506A is specifically claimed in U.S. Pat. No. 4,495,358, there is no mention of insecticidal activity associated with antibiotic SS46506A either in U.S. Pat. No. 4,495,358 nor in Meiji Seika Kaisha other references on pyrrolomycins.

Meiji Seika Kaisha SS46506A and Pyrrolomycins

SS46506A

Pyrrolomycins

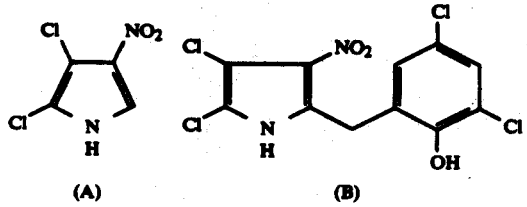

(A)    (B)

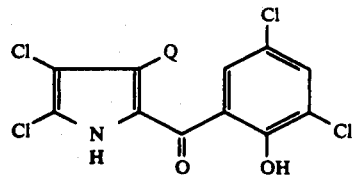

(C): Q = H
(D): Q = Cl

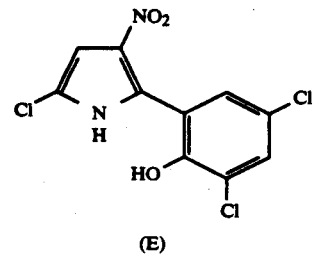

(E)

and

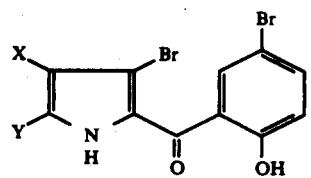

|      | X  | Y  |
|------|----|----|
| (F₁) | Br | Br |
| (F₂a)| Cl | Br |
| (F₂b)| Br | Cl |
| (F₃) | Cl | Cl |

Nippon Soda and Ciba Geigy have also worked in the area of pyrrole chemistry. Both have shown that 3-aryl-4-cyano pyrroles are effective for fungicidal and bactericidal applications. Nippon Soda has disclosed 3-aryltrihalo pyrroles as agents for the control of plant diseases.

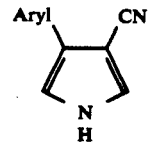

Yet another reference of interest in the pyrrole art is the U.S. Pat. No. 3,963,746 which describes 4,5-dihalopyrrol-2-yl di and tri halomethyl ketones. These compounds are said to have some activity against mites, however, when evaluated by the screening procedures described in the present specification, 4,5-dichloropyrrol-2-yl trichloromethylketone was inactive against insects, mites and nematodes.

Other references that disclose somewhat related pyrroles include the Japanese Fujisawa Pharm. Co. ltd. patent application J69001528-B that describes certain aryl/cyano and aryl/nitro pyrroles in which the pyrrole function is trisubstituted and the compounds are muscle relaxants. The compounds of the present invention have a tetrasubstituted pyrrole function and the compounds are insecticidal, nematicidal or acaricidal.

The U.S. Pat. 4,563,472, issued Jan. 7, 1986 and assigned to Meiji Seika Kaisha ltd. describes a number of tetrazoles that are effective as anti-microbial agents. The patentees provide a broad disclosure covering certain pyrroles, imidazoles, pyrazoles, and tetrazoles. In the case of the pyrroles, substitution may be construed to include a phenyl or a 3-chloro-2-nitrophenyl group in combination with a halogen atom and a nitro group. In all cases, the structures are substituted on nitrogen by a triiodoallyl or iodopropargyl group. There are no examples of tetra-substituted pyrroles of the types included in the present case and no finding of insecticidal activity.

A Japanese patent application J62098562-A, Sanyo Electric Company on May 8, 1987 describes organic semiconductors derived from reaction products of nitrogen oxides with heterocyclic compounds. Among the broad characterization of heterocyclic compounds covered i.e. furans, thiophenes, and selenophenes are included, in a broad generic sense, certain pyrroles. However, none of the pyrroles actually described in the reference are within the disclosure of the subject application and no actual example is to be found for utilizing any pyrrole of the applicant except pyrrole itself.

European patent application 206523 of Imperial Chemical Industries dated Dec. 30, 1986 describes a series of fungicidal 3-alkoxy-2-heterocyclylacrylic acid esters in which the heterocylic group may encompass certain substituted pyrroles. However, none of the actual examples disclosed in that case include pyrrole ring substituents which come within the scope of the generic disclosure of the subject application and, furthermore, such acrylic acid-pyrrole combinations are not a part of the insecticidal compounds described herein.

It is therefore an object of the present invention to provide novel arylpyrrole compounds that are highly effective for controlling insects, acarina and nematodes. It is also an object of the invention to protect harvested and growing crops from attack by insects, acarina and nematodes.

These and other objects will become more apparent from the detailed description of the invention set forth below.

SUMMARY OF THE INVENTION

The present invention is directed to certain novel arylpyrrole compounds that are highly effective insecticidal, acaricidal and nematicidal agents useful for the control of insect, acarid and nematode pests and for protecting agronomic crops, both growing and harvested, against the ravages of said pests. The present invention is also directed to methods for preparing the arylpyrrole compounds.

The novel arylpyrrole compounds of the present invention have the structural formula illustrated as formula I:

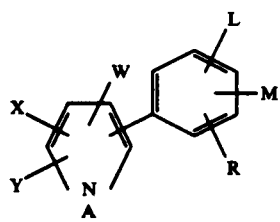

wherein X is F, Cl, Br, I, or $CF_3$; Y is F, Cl, Br, I, $CF_3$ or CN; W is CN or $NO_2$ and A is H; $C_1$-$C_4$ alkyl optionally substituted with from one to three halogen atoms, one hydroxy, one $C_1$-$C_4$ alkoxy or one $C_1$-$C_4$ alkylthio, one phenyl optionally substituted with $C_1$-$C_3$ alkyl or $C_1$-$C_3$ alkoxy or with one to three halogen atoms, one phenoxy optionally substituted with one to three halogen atoms or one benzyloxy optionally substituted with one halogen substituent; $C_1$-$C_4$ carbalkoxymethyl; $C_3$-$C_4$ alkenyl optionally substituted with from one to three halogen atoms; cyano; $C_3$-$C_4$ alkynyl optionally substituted with one halogen atom; di-($C_1$-$C_4$ alkyl) aminocarbonyl; or $C_4$-$C_6$ cycloalkylaminocarbonyl; L is H, F, Cl or Br; and M and R are each independently H, $C_1$-$C_3$ alkyl, $C_1$-$C_3$ alkoxy, $C_1$-$C_3$ alkylthio, $C_1$-$C_3$ alkylsulfinyl, $C_1$-$C_3$ alkylsulfonyl, cyano, F, Cl, Br, I, nitro, $CF_3$, $RICF_2Z$, $R_2CO$ or $NR_3R_4$, and when M and R are on adjacent positions and taken with the carbon atoms to which they are attached they may form a ring in which MR represents the structure:

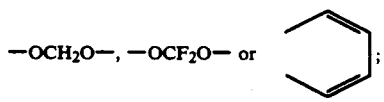

Z is $S(O)n$ or O; $R_1$ is H, F, $CHF_2$, CHFCl, or $CF_3$; $R_2$ is $C_1$-$C_3$ alkyl, $C_1$-$C_3$ alkoxy, or $NR_3R_4$; $R_3$ is H or $C_1$-$C_3$ alkyl; $R_4$ is H, $C_1$-$C_3$ alkyl, or $R_5CO$; $R_5$ is H or $C_1$-$C_3$ alkyl; and n is an integer of 0, 1 or 2.

The term $C_4$-$C_6$ cycloalkylamino carbonyl means a $C_4$ to $C_6$ cycloalkylamino group attached directly to the carbonyl group through the nitrogen atom.

DETAILED DESCRIPTION OF THE INVENTION

A preferred group of novel arylpyrroles of the present invention are illustrated by formula II:

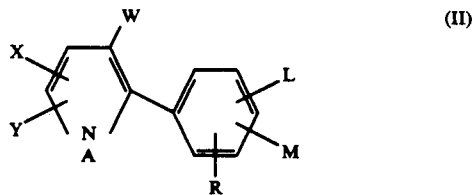

wherein A, L, M, R, W, X and Y are as described above.

Another preferred group of novel arylpyrroles of this invention are represented by formula III:

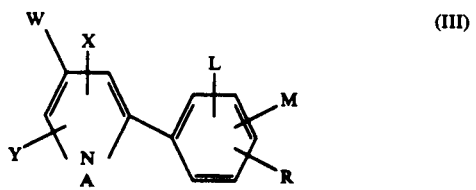

wherein A, L, M, R, W, X and Y are as described above.

Another group of preferred arylpyrroles of the invention are depicted by formula IV:

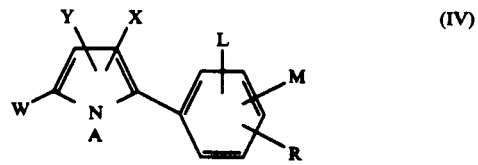

wherein A, L, M, R, W, X and Y are as described above.

Yet another group of preferred arylpyrroles of this invention are delineated by formula V:

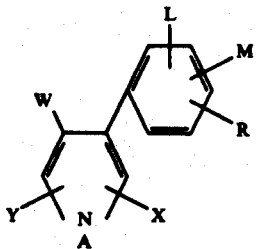

wherein A, L, M R, W, X and Y are as described above; and still other preferred arylpyrroles of the invention are depicted by formulas VI and VII:

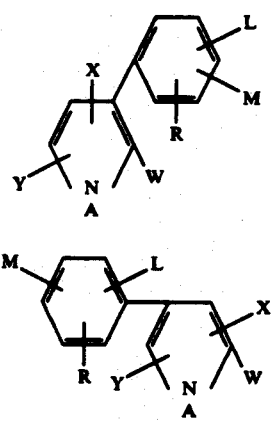

wherein A, L, M, R, W, X and Y are as described above.

Preferred formula I arylpyrroles of the invention are those in which A is hydrogen or $C_1$–$C_4$ alkoxymethyl; W is CN or $NO_2$; L is hydrogen or F; X and Y are each Cl, Br or $CF_3$; M is H, F, Cl or Br; and R is F, Cl, Br, $CF_3$ or $OCF_3$.

Preferred formula II compounds which are especially effective as insecticidal, acaricidal and/or nematicidal agents are those in which A is hydrogen or $C_1$–$C_4$ alkoxymethyl; L is hydrogen; M is hydrogen, F, Cl or Br; R is F, Cl, Br, $CF_3$ or $OCF_3$; W is CN and X and Y are each independently Cl, Br or $CF_3$.

Other formula II compounds that are highly effective as insecticidal, acaricidal and/or nematicidal agents are those in which A is hydrogen or $Cl_1$–$C_4$ alkoxymethyl; L is hydrogen; M is hydrogen, F, Cl or Br; R is F, Cl, Br, $CF_3$ or $OCF_3$; W is $NO_2$ and X and Y are each independently Cl, Br or $CF_3$.

Illustrative of some of the insecticidal, acaricidal and nematicidal arylpyrroles of the present invention are:
4,5-dichloro-2-(3,4-dichlorophenyl)pyrrole-3-carbonitrile;
4,5-dichloro-2-[p-(trifluoromethoxy)phenyl]pyrrole-3-carbonitrile;
4-bromo-5-chloro-2-(p-chlorophenyl)pyrrole-3-carbonitrile;
5-bromo-4-chloro-2-(3,4-dichlorophenyl)pyrrole-3-carbonitrile;
4,5-dichloro-2-(o-chlorophenyl)pyrrole-3-carbonitrile;
2-(p-bromophenyl)-4,5-dichloropyrrole-3-carbonitrile;
4,5-dichloro-2-(α, α, α-trifluoro-p-tolyl)pyrrole-3-carbonitrile;
4,5-dibromo-2-(α,α,α-trifluoro-p-tolyl)pyrrole-3-carbonitrile;
4,5-dibromo-2-(o-chlorophenyl)pyrrole-3-carbonitrile;
4,5-dibromo-2-(p-chlorophenyl)pyrrole-3-carbonitrile;
4,5-dichloro-2-(2,4-dichlorophenyl)pyrrole-3-carbonitrile;
4,5-dibromo-2-(2,4-dichlorophenyl)pyrrole-3-carbonitrile;
2,3-dibromo-4-nitro-5-phenylpyrrole;
2-(p-bromophenyl)-4,5-dichloro-3-nitropyrrole;
2,3-dichloro-4-nitro-5-(α, α, α-trifluoro-p-tolyl)pyrrole;
4,5-dichloro-2-(m-chlorophenyl)pyrrole-3-carbonitrile;
4,5-dichloro-2-(p-chlorophenyl)pyrrole-3-carbonitrile;
4,5-dichloro-2-phenylpyrrole-3-carbonitrile;
2,3-dichloro-5-(p-chlorophenyl)-4-nitropyrrole;
2-bromo-3-chloro-5-(p-chlorophenyl)-4-nitropyrrole;
2,3-dibromo-5-(p-chlorophenyl-4-nitropyrrole;
2,3-dichloro-4-nitro-5-phenylpyrrole;
3-bromo-2-chloro-4-nitro-5-(α,α, α-trifluoro-p-tolyl)-pyrrole;
5-Chloro-2-(3,4-dichlorophenyl)-1-(methoxymethyl)-4-(trifluoromethyl)pyrrole-3-carbonitrile;
5-Bromo-2-(m-fluorophenyl)-3-nitro-4-(trifluoromethyl) pyrrole;
2-(p-chlorophenyl)-5-(trifluoromethyl)pyrrole-3-carbonitrile;
3-Bromo-5-(p-fluorophenyl)-4-nitro-2-(trifluoromethyl) pyrrole;
4-Bromo-2-(p-chlorophenyl)-1-(ethoxymethyl)-5-(trifluoromethyl)pyrrole-3-carbonitrile;
4-Chloro-2-(3,5-dichloro-4-methylphenyl)-3-nitro-5-(trifluoromethyl)pyrrole;
2-(2-Bromo-4-chlorophenyl)-1-(2-propynyl)-4,5-bis-(trifluoromethyl)pyrrole-3-carbonitrile;
2-(2,5-Difluorophenyl)-3-nitro-4,5-bis-(trifluoromethyl)pyrrole;
5-[p-(Trifluoromethoxy)phenyl]pyrrole-2,4-dicarbonitrile;
5-(p-Dimethylaminophenyl)-4-nitropyrrole-2-carbonitrile;
3-Bromo-5-(p-chlorophenyl)pyrrole-2,4-dicarbonitrile;
4-Bromo-2-(p-chlorophenyl)-5-nitropyrrole-3-carbonitrile;
5-(p-Methylthiophenyl)-3-(trifluoromethyl)pyrrole-2,4-dicarbonitrile;
1-Allyl-4-nitro-5-(α, α, α-trifluoro-p-tolyl)-3-(trifluoromethyl)pyrrole-2-carbonitrile;
4-Chloro-2-(p-chlorophenyl)pyrrole-3-carbonitrile;
2-(m-Methanesulfonylphenyl)-4-(trifluoromethyl)pyrrole-3-carbonitrile;
2-(3-chloro-4-methylphenyl)-1-methyl-3-nitro-4-(trifluoromethyl)pyrrole;
2-Phenylpyrrole-3,4-dicarbonitrile;
5-(p-Ethanesulfinylphenyl)-4-nitropyrrole-3-carbonitrile;
2-Bromo-5-phenylpyrrole-3,4-dicarbonitrile;
2-Chloro-5-(3,5-dichlorophenyl)-4-nitropyrrole-3-carbonitrile;
1-Benzyl-4-nitro-5-(p-chlorophenyl)-2-(trifluoromethyl) pyrrole-3-carbonitrile;
2-Chloro-5-(m-bromophenyl)pyrrole-3-carbonitrile;
2-Bromo-1-(p-chlorophenoxy)methyl-5-(p-chlorophenyl)-3-nitropyrrole;
2,4-Dibromo-5-phenylpyrrole-3-carbonitrile;
5-(p-Bromophenyl)-2,4-dichloro-3-nitropyrrole;
2-Bromo-5-(3-bromo-4-methylphenyl)-1-(n-propyloxy)methyl-4-(trifluoromethyl)pyrrole-3-carbonitrile;

2-Bromo-5-(p-chlorophenyl)-3-nitro-4-(trifluoromethyl) pyrrole;
5-[m-(Difluoromethoxy)phenyl]-2-(trifluoromethyl)pyrrole-3-carbonitrile;
5-(2,3-Dichlorophenyl)-1-methoxymethyl-3-nitro-2-(trifluoromethyl)pyrrole;
4-Chloro-5-(β-napthyl)-2-(trifluoromethyl)pyrrole-3-carbonitrile;
3-Bromo-2-(3,4-dichlorophenyl)-4-nitro-5-(trifluoromethyl)pyrrole;
5-(2-Bromo-5-ethylphenyl)-2,4-bis-(trifluoromethyl)pyrrole-3-carbonitrile;
1-Ethyl-2-(p-fluorophenyl)-4-nitro-3,5-bis-(trifluoromethyl)pyrrole;
1-[(2,6-Dichlorophenoxy)methyl]-5-(m-chlorophenyl)pyrrole-2,3-dicarbonitrile;
3-Nitro-5(α,α,α-trifluoro-p-tolyl)pyrrole-2-carbonitrile;
4-Chloro-5-(4-chloro-2-methylphenyl)pyrrole-2,3-dicarbonitrile;
4-Bromo-5-(3,4-dibromophenyl)-2-nitropyrrole-3-carbonitrile;
1-[(1-Methoxy)ethyl]-5-(p-chlorophenyl)-4-(trifluoromethyl)pyrrole-2,3-dicarbonitrile;
5-(p-Isopropylphenyl)-2-nitro-4-(trifluoromethyl) pyrrole-3-carbonitrile; 4-Chloro-5-(3,4-difluoromethylenedioxyphenyl)pyrrole-3-carbonitrile;
3-Bromo-2-(3-chloro-4-cyanophenyl)-4-nitropyrrole;
1-[(3,4-dichlorobenzyloxy)methyl]-2-(m-bromophenyl)pyrrole-4-carbonitrile;
2-(3,5-Dichloro-4-methylphenyl)-4-nitro-3-trifluoromethylpyrrole;
2-Phenylpyrrole-3,4-dicarbonitrile;
2-(2-Bromo-4-chlorophenyl)-4-nitropyrrole-3-carbonitrile;
2-Bromo-5-phenylpyrrole-3,4-dicarbonitrile;
5-Chloro-2-(3,4-dibromophenyl)-1-methyl-4-nitropyrrole-3-carbonitrile;
2-(p-Chlorophenyl-5-(trifluoromethyl)pyrrole-3,4-dicarbonitrile;
2-(o-Bromophenyl)-4-nitro-5-(trifluoromethyl)pyrrole-3-carbonitrile;
3-Bromo-5-(3-chloro-4-methoxy)pyrrole-2-carbonitrile;
3-Bromo-5-(m-bromophenyl)-2-nitropyrrole;
3,4-Dibromo-5-(3,4-dichlorophenyl)pyrrole-2-carbonitrile;
2-(3-Chloro-4-cyanophenyl)-5-nitro-3,4-dichloropyrrole;
3-Chloro-1-(p-methoxybenzyl)-5-(3,4-difluorophenyl)-4-(trifluoro-methyl)pyrrole-2-carbonitrile;
3-Bromo-5-(3,5-dibromo-p-tolyl)-2-nitro-4-(trifluoromethyl)pyrrole;
1-(2,3,3-Trichloroally)-5-(p-chlorophenyl)-3-(trifluoromethyl)pyrrole-2-carbonitrile;
2-(p-Iodophenyl)-5-nitro-4-(trifluoromethyl)pyrrole;
4-Chloro-5-(m-isopropylphenyl)-3-(trifluoromethyl)pyrrole-2-carbonitrile;
3-Bromo-1-methyl-2-(3-fluoro-4-methylphenyl)-2-nitro-3-(trifluoromethyl)pyrrole;
5-(p-Bromophenyl)-1-isopropyl-3,4-bis-(trifluoromethyl) pyrrole-2-carbonitrile;
2-(3,4-Dichloro-4-methylthio)-5-nitro-3,4-bis-(trifluoromethyl)pyrrole;
5-(m-Difluoromethoxyphenyl)pyrrole-2,3-dicarbonitrile;
5-(3-Bromo-4-cyanophenyl)-2-nitropyrrole-3-carbonitrile;
4-Chloro-1-methoxymethyl-5-(p-bromophenyl)pyrrole-2,3-dicarbonitrile;
4-Bromo-5-(2,6-dichloro-4-methylthio)-2-nitropyrrole-3-carbonitrile;
1-[(p-Bromophenoxy)methyl]-5-(m-trifluoromethyl)-4-(trifluoromethyl)pyrrole-2,3-dicarbonitrile;
5-(α-Naphthyl)-2-nitro-4-(trifluoromethyl)pyrrole-3-carbonitrile;
4-Bromo-5-(3-bromo-4-trifluoromethylphenyl)pyrrole-2-carbonitrile;
3-Chloro-2-(2,3-dichlorophenyl)-5-nitropyrrole;
5-(m-Cyanophenyl)-3-(trifluoromethyl)pyrrole-2-carbonitrile;
2-(3-Bromo-4-isopropoxy)-5-nitro-3-(trifluoromethyl) pyrrole;
5-(p-Chlorophenyl)pyrrole-2,4-dicarbonitrile;
2-(3,4-Dichlorophenyl)-5-nitropyrrole-3-carbonitrile;
3-Bromo-5-(3,4-dichlorophenyl)pyrrole-2,4-dicarbonitrile;
4-Bromo-2-(3,4-dichlorophenyl)-5-nitropyrrole-3-carbonitrile;
5-(3,4-Dibromophenyl)-3-(trifluoromethyl)pyrrole-2,4-dicarbonitrile;
2-(m-Chlorophenyl)-5-nitro-4-(trifluoromethyl)pyrrole-3-carbonitrile;
5-Bromo-3-(3,5-dichloro-4-difluoromethoxyphenyl)pyrrole-2-carbonitrile;
2-Bromo-4-(2,5-dibromophenyl)-5-nitropyrrole;
2,3-Dibromo-4-(p-chlorophenyl)pyrrole-5-carbonitrile;
2,3-Dichloro-4-(3,5-difluorophenyl)-5-nitropyrrole;
5-Bromo-3-(p-chlorophenyl)-1-hydroxyethyl-4-(trifluoromethyl)pyrrole-2-carbonitrile;
2-Chloro-5-nitro-3-(trifluoromethyl)-4-(m-trifluoromethylphenyl)pyrrole;
3-(3-Bromo-4-chlorophenyl)-5-(trifluoromethyl)pyrrole-2-carbonitrile;
3-(3-Chloro-4-fluorophenyl)-2-nitro-5-(trifluoromethyl) pyrrole;
4-Bromo-3-(p-chlorophenyl)-1-methylthiomethyl-5-(trifluoromethyl)pyrrole-2-carbonitrile;
3-(4-Bromo-3-cyanophenyl)-4-chloro-2-nitro-5-(trifluoromethyl)pyrrole;
4-(p-Chlorophenyl)-2,3-bis-(trifluoromethyl)pyrrole-2-carbonitrile;
3-(2,3-Dichlorophenyl)-2-nitro-4,5-bis-(trifluoromethyl)pyrrole;
3-(3,4-Dichlorophenyl)pyrrole-2,5-dicarbonitrile;
4-(2-Bromo-4-methylphenyl)-5-nitropyrrole-2-carbonitrile;
3-Bromo-4-(3,5-dichloro-4-methylthiopheny.1)pyrrole-2,5-dicarbonitrile;
4-(m-Bromophenyl)-3-chloro-5-nitropyrrole-2-carbonitrile;
3-(p-Acetamidophenyl)-4-(trifluoromethyl)pyrrole-2,5-dicarbonitrile;
4-(m-Bromophenyl)-5-nitro-3-(trifluoromethyl)pyrrole-2-carbonitrile;
4-Chloro-3-(3,4-dichlorophenyl)-1-(1-propenyl)pyrrole-2-carbonitrile;
3-Bromo-4-(p-dimethylaminophenyl)-5-nitropyrrole;
1-(3,4-Dichlorobenzyl(-3-(p-chlorophenyl)-4-(trifluoromethyl)pyrrole-2-carbonitrile;
2-Nitro-3-(p-tetrafluoroethoxyphenyl)-4-(trifluoromethyl)pyrrole;
3-(3-Bromo-4-i-propylphenyl)pyrrole-2,4-dicarbonitrile;
4-(p-Ethylsulfonylphenyl)-5-nitropyrrole-3-carbonitrile;
5-Bromo-1-(2-methoxyethyl)-4-(2,4,6-trichlorophenyl)pyrrole-2,4-dicarbonitrile;

2-Chloro-4-(2,3-dichlorophenyl)-5-nitropyrrole-3-carbonitrile;

3-(p-Fluorophenyl)-5-(trifluoromethyl)pyrrole-2,4-dicarbonitrile;

4-(p-Iodophenyl)-5-nitro-2-(trifluoromethyl)pyrrole-3-carbonitrile;

5-Chloro-4-[p-(N-methylacetamido)phenyl]pyrrole-2-carbonitrile;

5-Bromo-4-(o-bromophenyl)-1-propargylpyrrole-2-carbonitrile;

5-Bromo-3-(o-bromophenyl)-5-nitropyrrole;

4-(p-Chlorophenyl)-3,5-dichloro-1-(2,3,3-trichloroally)pyrrole-2-carbonitrile;

3-Bromo-5-chloro-4-(p-chlorophenyl)-2-nitropyrrole;

5-Bromo-4-[p-(2,2-dichloro-1,1-difluoroethoxy)-phenyl]-3-(trifluoromethyl)pyrrole-2-carbonitrile;

2-Chloro-3-(2-bromo-4-ethylthiophenyl)-5-nitro-4-(trifluoromethyl)pyrrole;

3-(3-Bromo-4-acetylphenyl)-5-(trifluoromethyl)pyrrole-2-carbonitrile;

1-Cyano-3-(3,4-dibromophenyl)-5-nitro-2-(trifluoromethyl)pyrrole;

3-Bromo-1-methoxymethyl-4-(m-trifluoromethyl)-5-(trifluoromethyl)pyrrole-2-carbonitrile;

3-(p-Chlorophenyl)-4-iodo-5-nitro-2-(trifluoromethyl)pyrrole;

4-(p-Bromophenyl)-1-[(1-ethoxy)ethyl]-3,5-di-(trifluoromethyl)pyrrole-2-carbonitrile;

3-(2-Bromo-4-methoxyphenyl)-5-nitro-2,4-di-(trifluoromethyl)pyrrole;

3-(p-Chlorodifluoromethoxyphenyl)pyrrole-2,5-dicarbonitrile;

2-(p-Isobutyrylaminophenyl)-5-nitropyrrole-2-carbonitrile;

3-Bromo-4-(3,4-dimethoxyphenyl)pyrrole-2,5-dicarbonitrile;

4-Chloro-3-(p-chlorophenyl)-1-isopropyloxycarbonylmethyl-5-nitropyrrole-2-carbonitrile;

3-(o-Bromophenyl)-4-(trifluoromethyl)pyrrole-2,5-dicarbonitrile;

1-(2-Chloroethyl)-3-(3,4-dichlorophenyl)-4-(trifluoromethyl)pyrrole-2-carbonitrile;

4-(4-Bromo-3-trifluoromethoxyphenyl)-3-chloropyrrole-2-carbonitrile;

3-Bromo-4-(2,4-dichlorophenyl)-1-isopropyl-2-nitropyrrole;

4-(3-Methoxy-4-cyanophenyl)-3-(trifluoromethyl)pyrrole-2-carbonitrile;

1-(3,4-Dichlorobenzyl)-4-(2-methyl-4-iodophenyl)-2-nitro-3-trifluoromethylpyrrole;

1-Methyl-4-[3,5-di(trifluoromethyl)phenyl]pyrrole-2,3-dicarbonitrile;

4-(3,4-Dichlorophenyl)-2-nitropyrrole-3-carbonitrile;

4-(m-Bromophenyl)-1-carbomethoxymethyl-5-chloropyrrole-2,3-dicarbonitrile;

5-Bromo-4-(2,6-dichloro-4-methanesulfinylphenyl)-2-nitropyrrole-3-carbonitrile;

4-(p-Chlorophenyl)-1-(2,2,2-trifluoroethyl)-5-(trifluoromethyl)pyrrole-2,3-dicarbonitrile;

4-(3,5-Dichlorophenyl)-2-nitro-5-(trifluoromethyl)pyrrole-3-carbonitrile;

2-Chloro-4-(3-chloro-4-N-methylacetamidophenyl)pyrrole-3-carbonitrile;

2-Bromo-4-(3-bromo-4-n-propylphenyl)-3-nitropyrrole;

2,5-Dichloro-4-(3,5-dichloro-4-methylthiophenyl) pyrrole-3-carbonitrile;

2,5-Dibromo-1-(2,4-dibromophenoxymethyl)-3-(p-chlorophenyl-4-nitropyrrole;

4-(3-Bromo-4-cyanophenyl)-2-chloro-5-(trifluoromethyl) pyrrole-3-carbonitrile;

2-Bromo-1-methyl-3-nitro-4-(α,α,α-trifluoro-p-tolyl) pyrrole;

4-(p-chlorophenyl)-1-(n-butyloxymethyl)-5-(trifluoromethyl)pyrrole-3-carbonitrile;

4-(3,4-Methylenedioxyphenyl)-3-nitro-2-(trifluoromethyl)pyrrole;

5-Chloro-4-(3-chloro-4-trifluoromethoxyphenyl)-2-(trifluoromethyl)pyrrole-3-carbonitrile;

2-Bromo-3-(3,4-dichlorophenyl)-1-ethylthiomethyl-4-nitro-5-(trifluoromethyl)pyrrole;

4-[p-(tetrafluoroethoxy)phenyl]-2,5-di-(trifluoromethyl)pyrrole-3-carbonitrile;

3-(3-Bromo-4-acetoxyphenyl)-1-(3,4-dichlorophenoxymethyl)-4-nitro-2,5-di-(trifluoromethyl) pyrrole;

4-(p-Bromophenyl)-1-[(2-methoxy)ethyl]pyrrole-2,3-dicarbonitrile;

4-(m-Isopropionamidophenyl)-3-nitropyrrole-2-carbonitrile

5-Bromo-4-(2-chloro-4-methylthio)pyrrole-2,3-dicarbonitrile;

5-Chloro-4-(p-chlorophenyl)-1-hydroxyethyl-3-nitropyrrole-2-carbonitrile;

4-(3,5-Dibromo-4-cyanophenyl)-5-(trifluoromethyl)pyrrole-2,3-dicarbonitrile;

4-(4-Chloro-2-methylphenyl)-1-isopropylthiomethyl-3-nitro-5-(trifluoromethyl)pyrrole-2-carbonitrile;

5-Bromo-4-(3,4-dichlorophenyl)-1-(difluoromethyl) pyrrole-3-carbonitrile;

2-Chloro-3-(m-difluoromethoxyphenyl)-4-nitropyrrole;

1-(2,4-Dibromophenoxymethyl)-4-(m-chlorophenyl)-5-(trifluoromethyl)pyrrole-3-carbonitrile;

3-(3-Bromo-4-ethoxy)-4-nitro-2-(trifluoromethyl) pyrrole;

3-(2,4,6-Trichlorophenyl)pyrrole-2,4-dicarbonitrile;

3-(4-Bromo-3-chlorophenyl)-1-(difluoromethyl)-4-nitropyrrole-2-carbonitrile;

5-Bromo-3-(p-chlorophenyl)-1-(isobutyloxymethyl) pyrrole-3-carbonitrile;

3-(4-Bromo-3-methylphenyl)-5-chloro-4-nitropyrrole-2-carbonitrile;

3-(2-Naphthyl)-5-(trifluoromethyl)pyrrole-2,4-dicarbonitrile;

3-(3-Cyano-4-methylphenyl)-1-methyl-4-nitro-5-(trifluoromethyl)pyrrole-2-carbonitrile;

2,3-dichloro-5-(3,4-dichlorophenyl)-4-nitropyrrole 2-(3,5-dibromo-4-methoxyphenyl)-4,5-dichloropyrrole-3-carbonitrile;

2,3-dichloro-4-nitro-5-(2,4,6-trifluorophenyl)-4-nitropyrrole;

4,5-dibromo-2-(2,3,6-trifluorophenyl)-3-carbonitrile 4,5-dichloro-2-(3,4-dichlorophenyl)-1-(ethoxymethyl)-pyrrole-3-carbonitrile;

4,5-dibromo-1-methyl-2-(α,α,α-trifluoro-p-tolyl) pyrrole-3-carbonitrile;

4,5-dichloro-2-(3,4-dichlorophenyl)-1-ethylpyrrole-3-carbonitrile;

2,3-dichloro-4-nitro-5-[p-(trifluoromethoxy)phenyl]-pyrrole;

4,5-dichloro-2-[p-(trifluoromethoxy)phenyl]pyrrole-3-carbonitrile;

4,5-dichloro-2-(3,4-dichlorophenyl)-1-methylpyrrole-3-carbonitrile;

2,3-dichloro-5-(p-chlorophenyl)-1-methyl-4-nitro pyrrole; and 4-bromo-5-chloro-2-(p-chlorophenyl)-1-methylpyrrole-3-carbonitrile.

5-chloro-2-(3,4-dichlorophenyl)-4-fluoropyrrole-3-carbonitrile 2-bromo-5-(p-chlorophenyl)-1-(ethoxymethyl)-4-fluoropyrrole-3-carbonitrile 3-bromo-5-(p-chlorophenyl)-2-fluoro-4-nitropyrrole Certain novel arylpyrrole compounds of formula I, wherein A is hydrogen; W is CN and X, Y, L, M and R are as described above, can be prepared by reacting N-formyl-DL-phenyl-glycine or a substituted N-formylphenylglycine represented by the structure formula VIII:

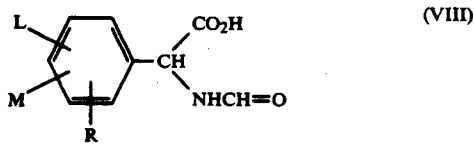

(VIII)

wherein L is H, F, Cl or Br; R and M are each independently H, $C_1$-$C_3$ alkyl, $C_1$-$C_3$ alkoxy, $C_1$-$C_3$ alkylthio, $C_1$-$C_3$ alkylsulfinyl, $C_1$-$C_3$ alkylsulfonyl, cyano, F, Cl, Br, I, nitro, $CF_3$, $R_1CF_2Z$, $R_2CO$ or $NR_3R_4$ and when on adjacent positions and taken together with the carbon atoms to which they are attached, M and R may form a ring in which MR represents the structure:

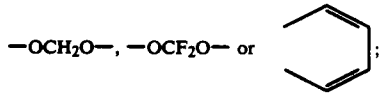

Z is $S(O)_n$ or O; $R_1$ is H, F, $CHF_2$, $CHFCl$ or $CF_3$; $R_2$ is $C_1$-$C_3$ alkyl, $C_1$-$C_3$ alkoxy or $NR_3R_4$; $R_3$ is H or $C_1$-$C_3$ alkyl; $R_4$ is H, $C_1$-$C_3$ alkyl or $R_5CO$; $R_5$ is H or $C_1$-$C_3$ alkyl and n is an integer of 0, 1 or 2; with at least an equivalent amount of a 2-chloroacrylonitrile and two to three equivalents of acetic anhydride. The reaction is conducted at an elevated temperature, preferably about 70° to 100° C.

The reaction can be illustrated as follows:

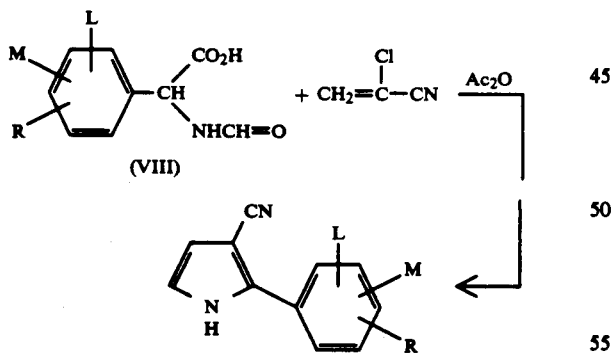

Conversion of the thus prepared 2-phenylpyrrole-3-carbonitrile or 2-(substituted phenyl)pyrrole-3-carbonitrile to the corresponding formula II, 4-halo, 5-halo or 4,5-dihalo-2-(substituted phenyl)pyrrole-3-carbonitrile, is readily achieved by reaction of the above said 2-phenylpyrrole-3-carbonitrile or 2-(substituted phenyl)-pyrrole-3-carbonitrile with at least about 1 or 2 equivalents of a sulfuryl halide, bromine or chlorine, in the presence of a solvent such as dioxane, THF, acetic acid or a chlorinated hydrocarbon solvent. For preparation of a monohalo pyrrole-3-carbonitrile use of about 1 equivalent of the halogenating agent is required;

whereas, preparation of a dihalo pyrrole-3-carbonitrile requires 2 to 3 equivalents of said halogenating agent. When sulfuryl chloride or sulfuryl bromide is used the reaction is generally conducted at a temperature below about 40° C. and preferably between about 0° and 30° C., but when elemental bromine is employed, the reaction is usually conducted at about 30°-40° C. Other effective halogenating agents that may be employed in these reactions include sodium hypochlorite, t-butylhypochlorite, N-bromosuccinimide, N-iodosuccinimide and the like. The reaction may be illustrated as follows:

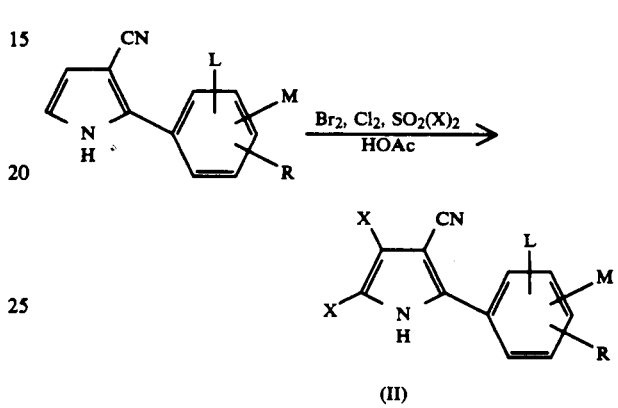

(II)

The formula II carbonitrile compounds of the present invention may also be prepared from the reaction of a substituted or unsubstituted benzoyl acetonitrile with a 2,2-di($C_1$-$C_4$ alkoxy)ethylamine in the presence of an aromatic solvent to form the α(2,2-di($C_1$-$C_4$ alkoxy)ethylamino-β-cyano-(substituted)styrene which is then converted to the 2-(substituted-phenyl)pyrrole-3-carbonitrile of formula II by reaction of said β-3-cyano-(substituted)styrene compound with trifluoroacetic acid or with concentrated HCl at a temperature between about 20° and 40° C. The reactions may be graphically illustrated as follows:

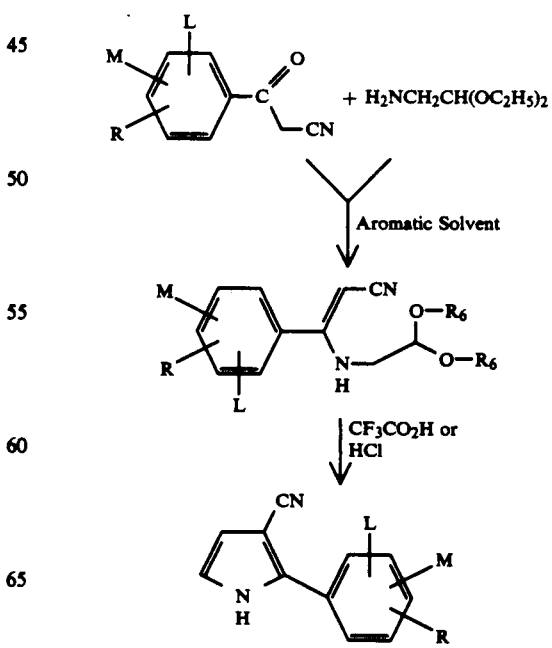

wherein $R_6$ is $C_1$–$C_4$ alkyl and L, R and M are as described above.

Also in accordance with the present invention formula II 3-nitro-2-phenylpyrrole and 3-nitro-2-(substituted)phenylpyrrole compounds can be prepared by reaction of an α-nitroacetophenone or a substituted α-nitroacetophenone with a 2,2-di($C_1$–$C_4$-alkoxy)ethylamine. The reaction is generally conducted in the presence of an inert organic solvent preferably an aromatic solvent, at an elevated temperature to give an α-(2,2-di($C_1$–$C_4$-alkoxy)ethylamino)-β-nitrostyrene or a substituted α-(2,2-di($C_1$–$C_4$-alkoxy)ethylamino)-β-nitrostyrene that is converted to the formula II 3-nitro-2-phenylpyrrole or 3-nitro-2-(substituted)phenylpyrrole by treatment with a mineral acid such as hydrochloric or hydrobromic acid. Reaction of the thus prepared nitrophenylpyrrole with sodium hypochlorite in the presence of an inert organic solvent at a reduced temperature yields the formula II 2,3-dichloro-4-nitro-5-phenyl or 5-(substituted)phenylpyrrole.

The above reactions may be graphically illustrated as follows:

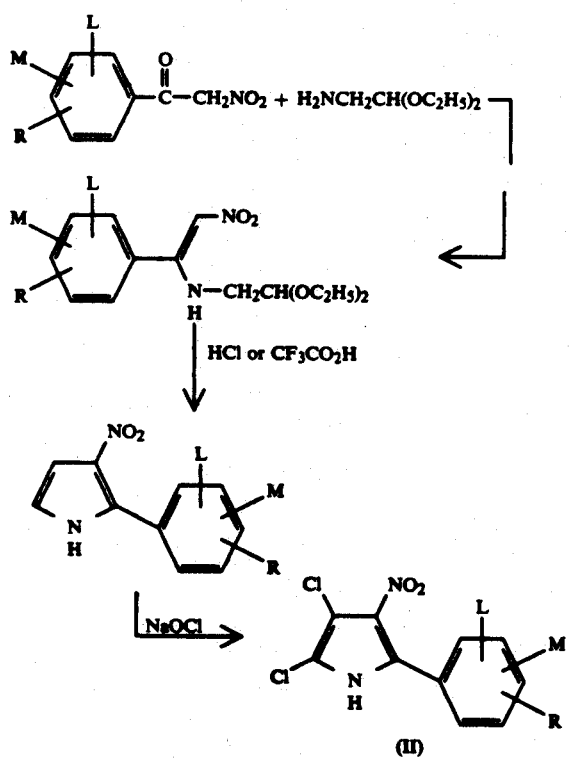

In addition to the several methods described in the literature for preparing substituted and unsubstituted benzoyl acetonitriles, surprisingly we have found that these compounds may also be prepared by reacting an appropriately substituted benzoyl halide with an alkali metal hydride and an alkyl cyanoacetate, such as t-butyl cyanoacetate, to yield the corresponding t-butyl(benzoyl or substituted benzoyl)cyanoacetate. These reactions may be graphically illustrated as follows:

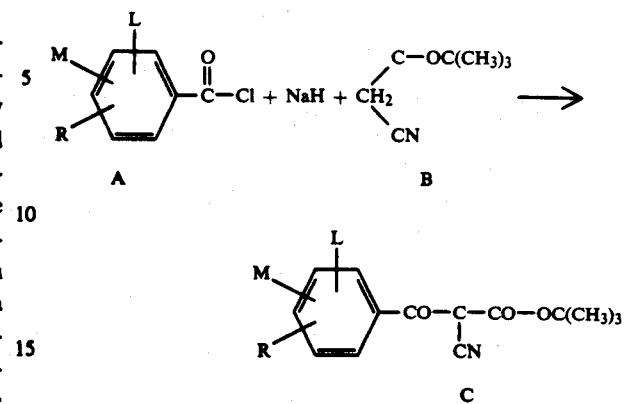

The thus formed cyanoacetate ester can then be converted to a substituted or unsubstituted benzoyl acetonitrile by heating the compound in toluene containing p-toluene sulfonic acid. The reaction may be graphically illustrated as follows:

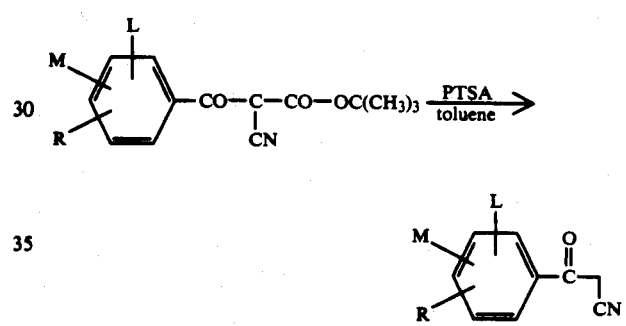

Examples of the t-butyl(benzyl and substituted benzoyl acetonitriles used in the above reactions are shown in Tables below.

t-Butyl(benzyl and Substituted benzyl)cyanoacetates

| L | M | R | mp °C. |
|---|---|---|---|
| H | 3-Cl | 4-Cl | 91–94 |
| H | H | 4-OCF$_3$ | 81–84 |
| H | H | 4-Br | 113–115 |
| H | H | 4-CF$_3$ | 146–147 |
| H | H | 4-F | 98–100 |
| H | H | 4-CN | 127–128 |
| H | H | 4-CF$_3$CH$_2$O | 136–139 |
| H | H | 4-CH$_3$SO$_2$ | 127–129 |
| H | 3-F | 4-F | 91–94 |
| H | H | 4-CH$_3$S | 117–119.5 |
| H | H | 4-CHF$_2$CF$_2$O | 92–94 |
| 3-Cl | 5-Cl | 4-CH$_3$O | — |

Benzoyl Acetonitriles

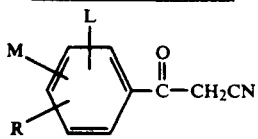

| L | M | R | mp °C. |
|---|---|---|---|
| H | H | 4-Cl | 128.5–129.5 |
| H | 3-Cl | 4-Cl | 105–107 |
| H | H | 2-C | 153–55 |
| H | H | 4-OCF$_3$ | 79–81 |
| H | H | 4-CF$_3$ | 44–45 |
| H | 2-Cl | 4-Cl | 66–67 |
| H | H | 3-Cl | 80–83 |
| H | H | 4-CN | 126–128 |
| H | H | 4-F | 78–80 |
| H | H | 4-SO$_2$CH$_3$ | 129–132 |
| H | 3-F | 4-F | 74–75 |
| H | H | 3-CF$_3$ | 58–60 |
| H | H | 4-CH$_3$ | 103.5–106 |
| H | H | 4-NO$_2$ | 119–124 |
| 3-Cl | 5-Cl | 4-OCH$_3$ | — |

Preparation of N-substituted formula I arylpyrroles can be achieved by reaction of the appropriately substituted formula I arylpyrrole, wherein A is hydrogen and L, M, R, W, X and Y are as described above, with an appropriate alkylating agent and a suitable base. For example, a brominated hydroxy-C$_1$–C$_4$-alkyl and potassium t-butoxide. This reaction provides an arylpyrrole having the same substituents as the starting material, but in addition is substituted on the nitrogen with hydroxy C$_1$–C$_4$ alkyl. In a similar reaction cyanogen bromide is substituted for the brominated hydroxy C$_1$–C$_4$ alkyl and yields the formula I arylpyrrole with a carbonitrile substituent on the nitrogen. The reactions may be illustrated as follows:

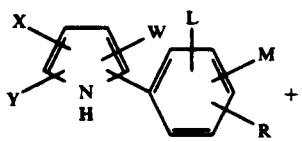

+

-continued (1) Br C$_1$–C$_4$ alcohol + K$^+$O-t-Bu (2) CNBr

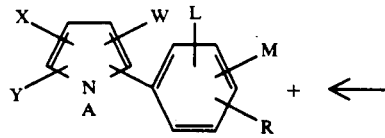

+ wherein L, M, R, W, X and Y are as described for formula I above and A is 1) C$_1$–C$_4$ alcohol or 2) CN.

Preparation of 2-phenylpyrrole 3,4-dicarbonitrile, 2-bromo-5-phenylpyrrole-3,4-dicarbonitrile and substituted phenyl derivatives thereof can be obtained by reaction of fumaronitrile with bromine in the presence of a chlorinated hydrocarbon such as chloroform at an elevated temperature to yield bromofumaronitrile. The thus formed bromofumaronitrile is then reacted with N-(trimethylsilyl)methyl-5-methyl-benzene-thioimidate or a substituted derivative thereof, in the presence of hexamethylphosphoramide at an elevated temperature to yield the 2-phenylpyrrole-3,4-dicarbonitrile. Bromination of the thus prepared 3,4-dicarbonitrile yields the 2-bromo-5-phenylpyrrole-3,4-dicarbonitrile or the substituted phenyl derivative if the substituted N-(trimethylsilyl)methyl-5-methyl-benzene-thioimidate is used in the previous reaction. The reaction may be graphically illustrated as follows:

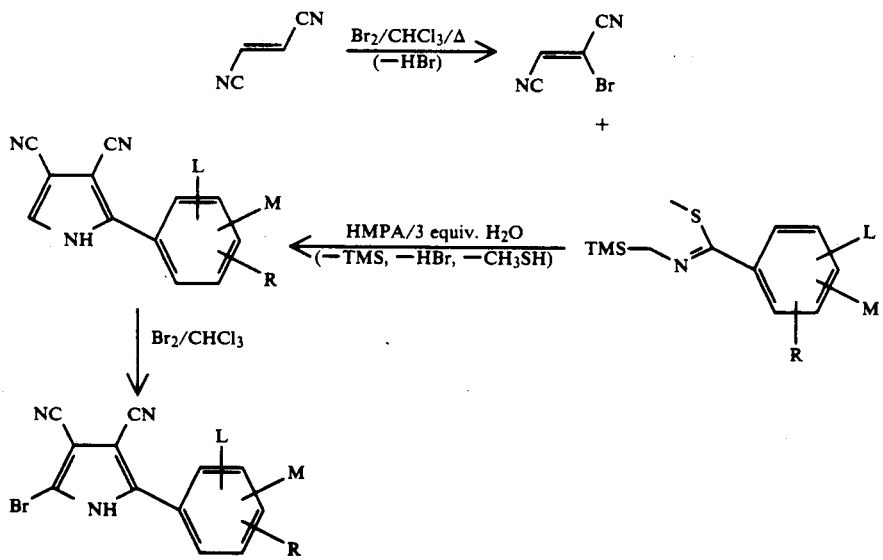

The examples provided by way of illustration below utilize the schemes illustrated above and provide a means for preparing other compounds of the invention which are not specifically described herein.

The arylpyrroles of the present invention are effective for controlling insects, acarina and nematodes. These compounds are also effective for protecting growing or harvested crops from attack by the abovesaid pests.

In practice generally about 10 ppm to about 10,000 ppm and preferably 100 to about 5000 ppm, of the formula I arylpyrrole, which encompasses all of the arylpyrrole isomers of formulas II, III, IV, V, VI and VII, dispersed in water or other inexpensive liquid carrier is effective when applied to the plants, the crops or the soil in which said crops are growing to protect said crops from attack by insects, acarina and/or nematodes. These compounds are also useful for protecting turf grass from attack by pests such as grubs, chinch bugs and the like.

The formula I arylpyrroles of this invention are also effective for controlling insects, nematodes and acarina, when applied to the foliage of plants and/or to the soil or water in which said plants are growing in sufficient amount to provide a rate of from about 0.125 kg/ha to about 4.0 kg/ha of active ingredient. Obviously higher rates of application of the formula I arylpyrroles may be used to protect crops from attack by insects, nematodes and acarina, however, higher rates of application are generally unnecessary and wasteful.

While the arylpyrroles of this invention are effective for controlling insects, nematodes and acarina when employed alone, they may be used in combination with other biological chemicals, including other insecticides, nematicides and acaricides. For example, the arylpyrroles of this invention may be used effectively in conjunction or combination with phosphates, carbamates, pyrethroids, formamidines, chlorinated hydrocarbons, halobenzoylureas and the like.

Advantageously, the above-said arylpyrroles may be formulated into dry compacted granules, flowable compositions, granular formulations, wettable powders, dusts, dust concentrates, microemulsions and the like, all of which lend themselves to soil, water and/or foliage application and provide the requisite plant protection. Such formulations include the compounds of the invention admixed with inert, pharmacologically-acceptable solid or liquid diluents.

For example, wettable powders, dusts and dust concentrate formulations of the invention can be prepared by grinding together about 3% to 20%, by weight, of the formula I arylpyrrole compound, with about 3% to 20% by weight of a solid anionic surfactant. One suitable anionic surfactant is a dioctyl ester of sodium sulfosuccinic acid, specifically Aerosol OTB® surfactant marketed by the American Cyanamid Company. About 60% to 94%, by weight, of an inert solid diluent, such as montmorillonite, attapulgite, chalk, talc, kaolin, diatomaceous earth, limestone, silicates or the like also is used in such formulations.

Compacted granules especially useful for soil or water application can be prepared by grinding together in about equal parts, usually about 3 to 20 parts, of the arylpyrrole and a solid surfactant, with about 60 to 94 parts of gypsum. Thereafter, the mixture is compacted into small granular particles, about 24/48 mesh or larger.

Other suitable solid surfactants useful in the present formulations include not only the anionic dioctyl ester of sodium sulfosuccinic acid but also nonionic block copolymers of ethylene oxide and propylene oxide. Such block copolymers are marketed by BASF Wyandotte Corporation as Pluronic 10R8®, 17R8®, 25R8®, F38®, F68®, F77® or F87®, and are especially effective for the preparation of compacted granules.

In addition to the powders and concentrate formulations described hereinabove, wettable powders and flowables may be used because they may be dispersed in water. Preferably, such flowables will be applied at the locus with the aqueous compositions being sprayed on the foliage of plants to be protected. These sprays also may be applied to the breeding ground, food supply or habitat of the insects and acarina sought to be controlled.

Where solid formulations of the compounds of this invention are to be used in combination treatments with other pesticidal agents, the formulations can be applied as an admixture of the components or may be applied sequentially.

Similarly, liquid formulations of the arylpyrrole in combination with other pesticidal agents may be tank mixed or may be applied separately, sequentially, as liquid sprays. Liquid spray formulations of the compounds of the invention should contain about 0.001% to about 0.1% by weight of the active arylpyrrole.

The following examples are presented as illustrations of the present invention.

EXAMPLE 1

2-Phenylpyrrole-3-carbonitrile

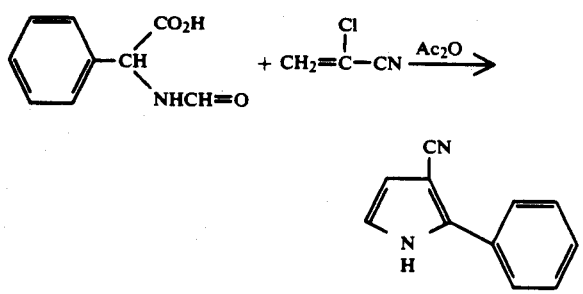

The following procedure is similar to the method given in JOC, 43, 4273-6 (1978). A magnetically stirred mixture of 30.00 g of N-formyl-phenylglycine is heated at 90° C. for 1 and ½ hours. The clear yellow reaction solution is concentrated in vacuo to give 42.5 g of an oily brownish orange semi-solid. Material partially purified by chromatography on silica gel is shown by the proton NMR spectrum to be a mixture of 73% 2-phenylpyrrole-3-carbonitrile and 27% 2-phenyl-3-cyano-5-methylpyrrole. Recrystallization once from chloroform and twice from 1,2-dichloroethane gives 1.69 g of an off-white solid which proton NMR shows it to be 96% 2-phenylpyrrole-3-carbonitrile, mp 148°-152° C.

Microanalysis (MW 168.19):
Calcd.: C, 78.55%; H, 4.79%; N, 16.66%
Found: C, 78.52%; H, 4.73%; N, 16.54%

EXAMPLE 2

4,5-Dichloro-2-phenylpyrrole-3-carbonitrile and 5-chloro-2-phenylpyrrole-3-carbonitrile

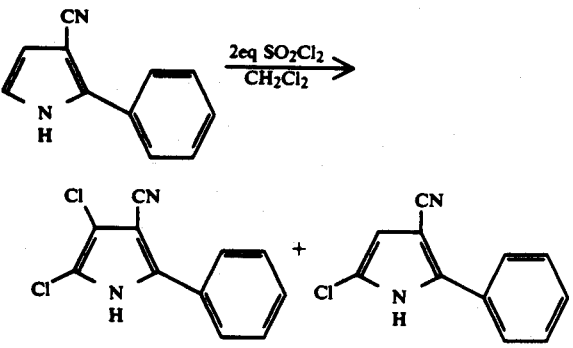

To a magnetically stirred ice-water cooled solution of 2.00 g (11.9 mmol,) of 2-phenyl-3-cyanopyrrole in 80 mL of methylene chloride is added dropwise over a period of 5 min., 1.90 mL (3.19 g, 23.6 mmol,) of sulfuryl chloride by means of a syringe. Throughout the addition the temperature is kept between 5° C. and 10° C. Stirring at 5°-10° C. is continued for 90 minutes. The reaction mixture is vacuum filtered to remove a precipitated solid (1.28 g) identified as 5-chloro-2-phenylpyrrole-3-carbonitrile, mp 192.5°-195° C. The filtrate is diluted with 400 mL of ethyl acetate, washed twice with 200 mL of water, dried (sodium sulfate), treated with charcoal, filtered, and then concentrated in vacuo to give (after slurrying of the residue with hexane) 0.60 g (21.3% yield) of a pink-purple solid. This solid is recrystallized from 5 mL of hot acetone to give 0.32 g (9% yield) of 4,5-dichloro-2-phenylpyrrole-3-carbonitrile as an orangish brown solid, mp 254°-255° C.

Max(mull,Nujol): 3165(br s), 3120(s), 2245(s), 1570(m), 1513(m), 1440(s), 1252(m), 1069(m), 996(m), 920(m), 768(s), 698(s), 665(s) cm$^{-1}$.

H-NMR(DMSO): $\delta$7.73 (d, J=6.6Hz, 1.97H, two phenyl protons at C-2,6), $\delta$7.52 (t, J=7.3Hz, 2.04H, two phenyl protons at C-3,5), $\delta$7.44 (t, J=7.3Hz, 1.02H, one phenyl proton at C-4).

C-NMR(DMSO): $\delta$137.51 (C-2 pyrrole carbon), $\delta$129.25 (C-4 phenyl carbon), $\delta$129.04 (C-3,5 phenyl carbons), $\delta$128.37 (C-1 phenyl carbon) $\delta$125.88 (C-2,6 phenyl carbons), $\delta$114.32 (either C-5 pyrrole or the nitrile carbon), $\delta$114.14 (either C-5 pyrrole or the nitrile carbon), $\delta$110.72 C-4 pyrrole carbon), $\delta$89.78 (C-3 pyrrole carbon).

Microanalysis (MW 237.09):
Calcd.: C, 55.72%: H, 2.55%: N, 11.82%; Cl, 29.91%
Found: C, 55.78%; H, 2.59%; N, 11.12%; Cl, 29.74%

EXAMPLE 3 p-Chloro-$\beta$-[(formylmethyl)amino]cinnamonitrile, diethyl acetal

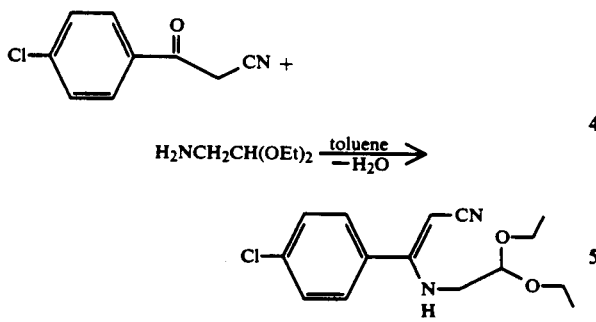

A magnetically stirred solution of 250.00 g (1.39 mol,) of p-chlorobenzoylacetonitrile, 203 mL (185.95 g, 1.39 mol) of 2,2-diethoxyethylamine, and 1300 mL of dried toluene is heated at refux for 20 hours. Water is collected in a Dean-Stark trap (23.8 mL, 95.2% theory). The hot cloudy dark brown solution with a large amount of undissolved solids is filtered through diatomaceous filter aid. After dilution with 200 mL of EtOAc, the solution is filtered through a 7 cm×13.5 cm column of silica gel. The filtrate is concentrated in vacuo to give 354.38 g (86.4% crude yield) of a clear dark oil which slowly solidifies. This solid is recrystalized from hot cyclohexane to give 324.26 g (79.1% yield) of a waxy orange solid. NMR of this product shows it to be composed of 78% (Z) and 23% (E) isomeric mixture of p-chloro-$\beta$-[(formylmethoyl)amino]cinnamonitrile, diethyl acetal, m.p. 60°-72° C. The following analytical data is for another similarly prepared sample.

Max(mull,Nujol): 3325(s), 3065(m), 2197(s), 1600(s), 1530(s), 1314(m), 1265(m), 1173(m), 1154(m), 1128(s), 1100(s), 1060(s), 1022(s), 939(m), 895(m), 844(s), 768(m), 730(m) cm$^{-1}$.

H-NMR(chloroform): $\delta$7.47 (d, J=8.6Hz, 2.12H, two aromatic protons), $\delta$7.37 (d, J=8.6Hz, 2.12H, two aromatic protons), $\delta$5.10(E) & $\delta$4.86(Z) [br t, 1.25H, one N-H proton], $\delta$4.69(Z) & $\delta$4.60(E) [t, J=5.1Hz, 1.05H, one methine proton at the acetal carbon], $\delta$4.07 (E) & $\delta$4.05(Z) [s, 0.83H, enamine $\beta$ proton], $\delta$3.71(E) & $\delta$3.68(Z) [q, J=7.1Hz, 2.22H, two methylene protons of one of two ethoxy groups], $\delta$3.56(Z) & $\delta$3.53(E) [q, J=7.1Hz, 2.22H, two methylene protons of one of two ethoxy groups], $\delta$3.18 (t, J=5.1Hz, 1.77H, two methylene protons of the ethyleneacetal group), $\delta$1.20 (t, J=7.1Hz, 4.90H, six methyl protons of the two ethoxy groups).

C-NMR(chloroform): $\delta$161.21 ($\alpha$-enamine carbon), $\delta$136.29 (Z) & $\delta$134.60(E) [either C-1 or C-4 of the phenyl ring], $\delta$134.08(Z) & $\delta$132.30(E) [either C-1 or C-4 of the phenyl ring], $\delta$129.34(Z) & $\delta$129.89(E) [either C-2,6 or C-3,5 of the phenyl ring], $\delta$128.94(Z) & $\delta$128.63(E) [either C-2,6 or C-3,5 of the phenyl ring], $\delta$121.19(Z) & $\delta$119.50(E) [nitrile carbon], $\delta$99.43(Z) & $\delta$100.63(E) [$\beta$-enamine carbon], $\delta$61.88(Z) & $\delta$63.25(E) [methine carbon of the acetal], $\delta$62.64(Z) & $\delta$63.03(E) [methylene carbons of the ethoxy groups], $\delta$46.32(Z) & $\delta$47.33(E) [methylene carbon of the ethyl amine group], $\delta$15.26 (methyl carbons of the ethoxy groups).

Microanalysis (MW 294.78):
Calcd: C, 61.11%; H, 6.50%; N, 9.51%' Cl, 12.03%.
Found: C, 61.25%; H, 6.25%; N, 9.34%; Cl, 12.35%.

EXAMPLE 4

2(p-Chlorophenyl)-pyrrole-3-carbonitrile

To 108 mL of trifluoroacetic acid stirred at 23° C. is added 54.00 g (0.183 mol) of solid p-chloro-$\beta$-[(formylmethyl)amino]cinnamonitrile, diethyl acetal over a period of 45 minutes. This addition produced an exotherm to 38° C. and, 32 minutes into the addition, a solid started to precipitate. After stirring at room temperature for 30 minutes, the reaction mixture is vacuum filtered and the collected solid is washed first with trifluoroacetic acid, secondly with an ethyl acetate-hexane mixture, and finally with hexane. The yield is 16.83 g (45.4%) of an off-white solid, mp 165°-166° C. The following anal. data is from a similarly prepared sample.

Max(mull, Nujol): 3275(br s), 2225(s), 1502(s), 1410(m), 1275(m), 1200(m), 1108(s), 1023(m), 999(m), 908(m), 843(s), 752(s), 722(s), 695(s), 620(s) cm$^{-1}$.

H-NMR(acetone): δ11.22 (v br s, 0.99H, one pyrrole N-H proton), δ7.82 (d, J=8.9Hz, 2.46H, two aromatic phenyl protons), δ7.51 (d, J=8.9Hz, 2.46Hz, two aromatic phenyl protons), δ7.02 (t, J=2.6Hz, 1.01H, one pyrrole proton at C-5), δ6.58 (t, J=2.6Hz, 0.77H, one pyrrole proton at C-4).

C-NMR(acetone): δ137.73 (pyrrole C-2), δ134.42 (p-chlorophenyl at C-4), δ129.93 (methine carbons at C-3,5 of the phenyl ring), δ128.07 (methine carbons at C-2,6 of the phenyl ring), δ121.21 (pyrrole at C-5), δ117.93 (nitrile carbon), δ113.78 (pyrrole carbon at C-4), δ90.86 (pyrrole carbon at C-3).

Microanalysis (MW 202.64):
Calcd: C, 65.19%; H, 3.48%; N, 13.83%,; Cl, 17.50%
Found: C, 64.18%; H, 3.52%; N, 13.63%; Cl, 17.74%

Use of the above procedure as shown or with the substitution of concentrated hydrochloric acid for trifluoroacetic acid affords the following compounds:

| M and/or R | mp °C. | Acid Used |
|---|---|---|
| 4-Cl | 165-166 | conc. HCl, CF$_3$COOH |
| 3,4-di-Cl | 216-221 | CF$_3$COOH |
| 2-Cl | 156-157 | CF$_3$COOH |
| 4-OCF$_3$ | 143-145 | CF$_3$COOH |
| 4-CF$_3$ | 179-180 | CF$_3$COOH |
| 2,4-di-Cl | 197-199 | CF$_3$COOH |
| 3-Cl | 150-156 | CF$_3$COOH |
| 4-CN | 210-212 | CF$_3$COOH |
| 4-F | 167-170 | conc. HCl |
| 4-SO$_2$CH$_3$ | 221-221.5 | CF$_3$COOH |
| 3,4-di-F | 173-175.5 | CF$_3$COOH |
| 3-CF$_3$ | 166-168 | CF$_3$COOH |
| 4-COOCH$_3$ | 155.5-158 | CF$_3$COOH |
| 4-CH$_3$ | 117-137 | CF$_3$COOH |
| 4-NO$_2$ | 174-177 | CF$_3$COOH |

EXAMPLE 5

4,5-Dichloro-2-(p-chlorophenyl)pyrrole-3-carbonitrile

To a mechanically stirred solution of 16.83 g (83.1 mmol) of 2-(p-chlorophenyl)pyrrole-3-carbonitrile in 450 mL of glacial acetic acid at 36° C. is added dropwise 14.7 mL (24.70 g, 183.0 mmol) of sulfuryl chloride over a period of 18 minutes. The addition produces a slight exotherm to 39° C. and, after another 16 minutes, the reaction mixture is vacuum filtered. The collected solids are washed first with acetic acid and then with water. This solid after recrystallization from hot ethyl acetate, melts at 259°-261° C. By similar procedures other samples of this product were prepared and the analytical data for one such product is shown below.

Max(mull, Nujol): 3170(br s), 3100(m), 2225(s), 1508(m), 1097(m), 825(s), 717(m), 660(m) cm$^{-1}$.

H-NMR(DMSO): d7.72 (d, J=8.6Hz, 2.00H, two aromatic protons), δ7.56 (d, J=8.6Hz, 2.00H, two aromatic protons).

C-NMR(DMSO): δ136.01 (pyrrole C-2 carbon), δ133.92 (p-chlorophenyl C-4 carbon), δ129.09 (p-chlorophenyl C-3,5 carbons), δ127.41 (p-chlorophenyl C-4 carbon), δ127.11 (p-chlorophenyl C-1 carbon), δ114.49 (nitrile carbon), δ114.10 (pyrrole C-5 carbon), δ110.92 (pyrrole C-4 carbon), δ90.09 (pyrrole C-3 carbon).

Microanalysis (MW 271.54):
Calcd.: C, 48.65%, H, 1.86%; N, 10.32%; Cl, 39.17%
Found: C, 49.22%; H, 2.12%; N, 9.85%; Cl, 39.03%

EXAMPLE 6

4,5-Dibromo-2-(α,α,α-trifluoro-p-tolyl)-pyrrole-3-carbonitrile

To a stirred mixture of 0.8 g of 2-(α,α,α-trifluoro-p-tolyl)pyrrole-3-carbonitrile in 70 mL of chloroform is added 2 mL of bromine. The mixture, on stirring overnight, deposits a white solid which is collected by filtration. Thin layer chromatography 1:1 ethyl acetate-hexane) shows a single component; m.p >230° C.

Anal. Calc'd for C$_{12}$H$_5$ Br$_2$F$_3$N$_2$C, 36.55: H, 1.27; N, 7.11; Br, 40.61.

Found: C, 36.40; H, 1.08; N, 6.99; Br, 40.55.

Following the procedures of Examples 5 and 6, but substituting the appropriately substituted phenylpyrrole-3-carbonitrile for 2-(α, α,α-trifluoro-p-tolyl) pyrrole-3-carbonitrile yields the following compounds.

| L | M | R | X | Y | mp °C. |
|---|---|---|---|---|---|
| H | H | 4-NO$_2$ | Br | Br | 274-277 |
| H | H | 4-F | Cl | Cl | >200 |
| H | H | 4-F | Br | Br | >220 |
| H | H | 4-SO$_2$CH$_3$ | Cl | Cl | >230 |
| H | 3-F | 4-F | Cl | Cl | >230 |
| H | 3-F | 4-F | Br | Br | >220 |
| 2-Cl | 3-Cl | 4-Cl | Cl | Cl | |
| 2-Br | 3-Br | 4-Br | Br | Br | |

-continued

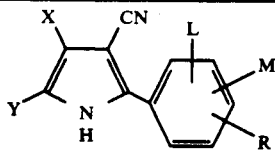

| L | M | R | X | Y | mp °C. |
|---|---|---|---|---|---|
| H | H | 4-OCF₃ | Cl | Cl | 222-225 |
| H | H | 4-OCF₃ | Br | Br | 231-232 |
| H | H | 4-OCF₃ | Cl | H | |
| H | H | 4-CN | Br | Br | >230 |
| H | H | 4-CN | Cl | Cl | >240 |
| H | H | 4-SO₂CH₃ | Br | Br | >230 |
| H | H | 4-NO₂ | Cl | Cl | 246-249 |
| H | 3-Cl | 4-Cl | Br | Br | >260 |
| H | H | 3-CF₃ | Cl | Cl | >230 |
| H | H | 4-COCH₃ | Cl | Cl | 251-254 |
| H | 2,3-CH=CH— | | Cl | Cl | 244-247 |
| H | H | 4-CH₃ | Cl | Cl | 215-217 |
| H | 2-Cl | 4-Cl | Br | Br | >230 |
| H | H | 3-Cl | Cl | Cl | >230 |
| H | 2-Cl | 4-Cl | Cl | Cl | >230 |
| H | H | 4-Cl | Br | Br | 273-274 |
| H | H | 2-Cl | Br | Br | >230 |
| H | H | 4-CF₃ | Cl | Cl | >230 |
| H | H | 4-Br | Cl | Cl | >235 |
| H | H | 2-Cl | Cl | Cl | >230 |
| H | 3-Cl | 4-Cl | Cl | Cl | >235 |
| H | H | H | Cl | Cl | 254-255 |
| H | H | 4-Cl | Cl | Cl | 255-257 |
| H | H | 4-CF₃ | Br | Br | >230 |
| H | H | 4-Cl | Cl | Br | 262-263(dec.) |
| H | H | 4-Cl | Br | Cl | 250-258(dec.) |
| H | 3-Cl | 5-Cl | Cl | Cl | >230 |
| H | 3-Cl | 4-Cl | Cl | Br | >230 |
| 2-Cl | 4-Cl | 5-F | Cl | Cl | 207-210 |

EXAMPLE 7

3-Nitro-2-phenylpyrrole

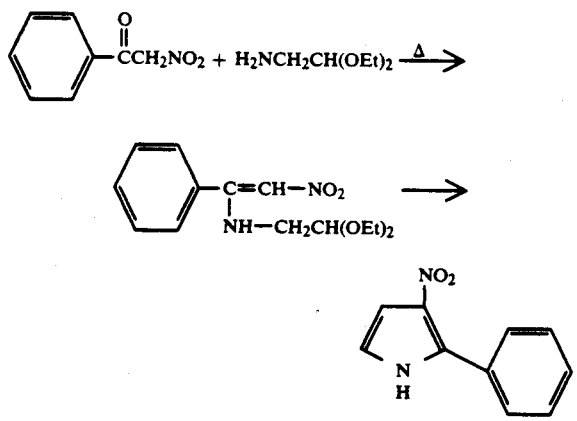

Alpha-nitro acetophenone (5.7 g, 0.0345 mol) is taken up in 100 mL toluene and 4.6 g (0.0345 mol) of amino acetaldehyde diethyl acetal is added. The reactants are put into a 250 mL RB flask fitted with a Dean-Stark trap. The trap is filled with 4A molecular sieves and the mixture is heated at reflux for 18 hours. The toluene is removed in vacuo to give 8.36 g of α-(2,2-diethoxyethylamino)-β-nitrostyrene as a brown oil. To this oil is added 50 mL of concentrated HCl. As the flask is swirled the oil turns to a yellow suspension. After 10 minutes the solid is filtered to give 2.48 g of a yellow solid. Recrystallization from ether/ethylacetate/hexane gives the product as two fractions, 2.08 g of m.p. 190°-192° C., (31%).

Max 1485 cm⁻¹(NO₂), H-NMR(CDCl₃/DMSO) δ6.73(m,2H), 7.46(m.5H).

EXAMPLE 8

2,3-Dichloro-4-nitro-5-phenylpyrrole

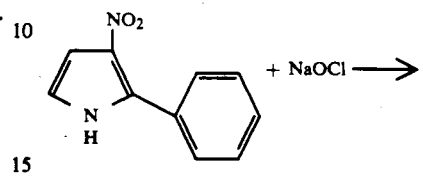

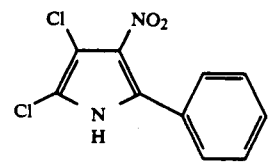

A mixture of 3-nitro-2-phenylpyrrole (1.56 g, 0.0083 mol) in 60 mL of dioxane is cooled in an ice bath while 25.9 g (0.0182 mol) of commercial sodium hypochlorite is added dropwise. After stirring for 45 minutes, the mixture is acidified with concentrated HCl. Water and Et₂O are added. The layers are separated and the top organic layer is washed with H₂O, dried over anhydrous MgSO₄ and concentrated in vacuo to give 2.21 g of yellow solid. Purification by chromatography using silica gel and eluting with increasing ratios of ethyl acetate/hexane gives, after stripping, 0.77 g of yellow solid (36%) m.p. 190°-190.5° C.;

Analysis: Calcd. for C₁₀H₆N₂O₂Cl₂C, 46.72; H, 2.35; N, 10.90

Found: C, 46.96; H, 2.86; N, 10.02

Following the procedures of Examples 7 and 8 above but using the appropriately substituted α-nitroacetophenone and 2,2-di(C₁-C₄ alkoxy)ethylamine yields the substituted α-(2,2-di(C₁-C₄ alkoxy)ethylamino)-β-nitrostyrene which is then converted to 3-nitro-2-(substituted)phenylpyrrole by treatment with HCl, HBr or CF₃CO₂H. Reaction of the thus formed substituted phenylpyrrole with sodium hypochlorite in dioxane yields the chloro analogs; whereas, reaction of the substituted phenylpyrrole with bromine in chloroform yields the bromine analogs.

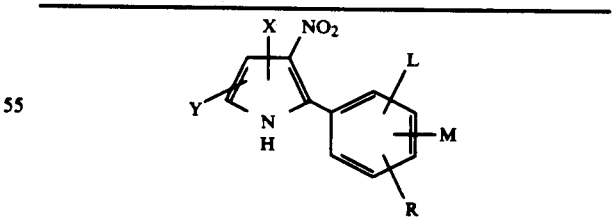

| L | M | R | X | Y | mp °C. |
|---|---|---|---|---|---|
| H | H | H | Cl | Cl | 190-190.5 |
| H | 4-Cl | H | Cl | Cl | 214-215 |
| H | 4-Cl | H | Br | Br | 203-204(dec.) |
| H | H | H | Br | Br | 148.5-149 |
| 3-Cl | 4-Cl | H | Cl | Cl | 219-220(dec.) |
| H | 4-Br | H | Cl | Cl | 222-223(dec.) |
| H | H | 4-CF₃ | Cl | Cl | 166-168 |

EXAMPLE 9

4,5-Dichloro-2-(3,4-dichlorophenyl)-1-methyl-pyrrole-3-carbonitrile

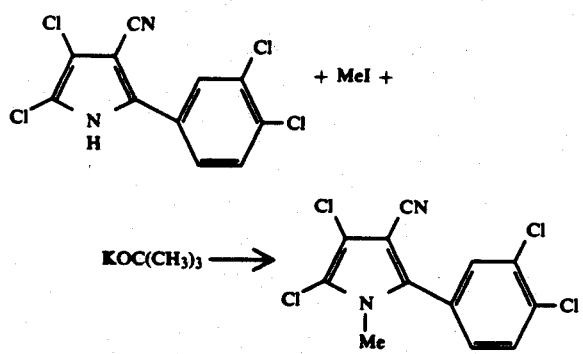

In a 100 mL flask, 2 g of 4,5-dichloro-2-(3,4-dichlorophenyl)pyrrole-3-carbonitrile in 60 mL dry THF gives a clear brown solution. 1 eq of KOtBu is added w/ stirring, this giving a clear solution after a few minutes. 1 eq of MeI is added by syringe and the solution is heated at reflux for 4 hours. It is then left to stir at RT overnight. The following day 50 mL of H2O is added and the mixture extracted with 4×50 mL CHCl3. The organic phases are combined, dried with MgSO4, and concentrated. The resulting white solid is purified by flash chromatography on silica gel, using 50/50 EtOAc/hexane as an eluent. This gives 1.80 g of a white solid.

Yield = 86%
m.p. = 154–156 deg. C

Following the above procedure but substituting the appropriately substituted phenylpyrrole-3-carbonitrile or 3-nitro-2-(substituted)phenylpyrrole for 4,5-dichloro-2-(3,4-dichlorophenyl)pyrrole-3-carbonitrile yields the compounds shown below.

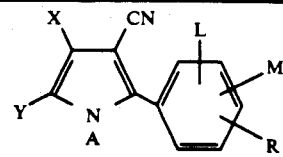

| A | L | M | R | X | Y | mp °C. |
|---|---|---|---|---|---|---|
| CH3 | H | H | 4-Cl | Cl | Cl | 152–153 |
| C2H5OCH2 | H | 3-Cl | 4-Cl | Cl | Cl | 128–130 |
| C2H5 | H | 3-Cl | 4-Cl | Cl | Cl | 137–138 |
| CH3 | H | 3-Cl | 4-Cl | Cl | Cl | 154–156 |
| CH3 | H | H | 4-CF3 | Br | Br | 145–146 |
| C6H5—CH2 | H | H | 4-CF3 | Br | Br | 145–147 |
| C6H5—CH2 | H | 3-Cl | 4-Cl | Cl | Cl | 95–96 |
| CH2=CH—CH2 | H | 3-Cl | 4-Cl | Cl | Cl | 69–70 |
| CH2=C—CH2<br>     \|<br>     Cl | H | 3-Cl | 4-Cl | Cl | Cl |  |
| CH≡C—CH2 | H | 3-Cl | 4-Cl | Cl | Cl | 147–148 |
| CH3SCH2 | H | 3-Cl | 4-Cl | Cl | Cl |  |
| C(CH3)3 | H | H | 4-CF3 | Cl | Cl |  |
| CH3 | H | H | 4-CF3 | Cl | Cl | 99–100 |
| CH3SC2H5 | H | 3-Cl | 4-Cl | Cl | Cl | 74–75 |
| C2H5—OC(O)—CH2 | H | 3-Cl | 4-Cl | Cl | Cl | 118–120 |
| C2H5—OCH2 | H | H | 4-CF3 | Cl | Cl | 99–100 |

-continued

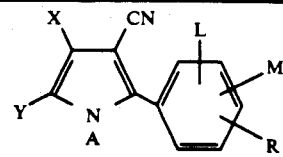

| A | L | M | R | X | Y | mp °C. |
|---|---|---|---|---|---|---|
| CH3 | H | H | 4-OCH3 | Br | Br | 112–115 |
| CH3 | H | H | 4-Cl | Br | Br | 197–201 |
| C2H5OCH2 | H | H | 4-OCF3 | Cl | Cl | 46–47 |
| CH3 | H | H | 4-OCF3 | Cl | Cl | 72–73 |
| C6H5—CH2 | H | H | 4-OCF3 | Cl | Cl | oil |
| C2H5OCH2 | H | H | 4-Cl | Cl | Cl | — |
| HOCH2CH2 | H | 3-Cl | 4-Cl | Cl | Cl | 143–145 |
| NC | H | 3-Cl | 4-Cl | Cl | Cl | 251–252 |
| C6H5CH2OCH2 | H | 3-Cl | 4-Cl | Cl | Cl | 88–89 |
| Cl O—CH2 | H | 3-Cl | 4-Cl | Cl | Cl | 118–120 |
| IC≡C—CH2 | H | 3-Cl | 4-Cl | Cl | Cl | 115–116 |
| CH3 | H | H | 4-Cl | Br | CF3 | 126–129 |
| C2H5OCH2 | H | H | 4-Cl | Br | CF3 | 91–92 |
| C2H5—OCH2 | H | 3-Cl | 4-Cl | Cl | Cl | 118–120 |
| C2H5—OCH2 | H | H | 4-Cl | Br | Br | 104–105 |
| C6H5—CH2 | H | H | 4-Cl | Br | Br | 81–82 |
| CH3 | H | H | 4-Cl | Br | Br | 197–201 |
| CN | H | H | 4-CF3 | Cl | Cl | 138–139 |
| C2H5—OCH2 | H | H | 4-CF3 | Br | CF3 | 104–105 |
| C2H5—OCH2 | H | H | 4-CF3 | H | CF3 | 76–77 |
| C2H5OCH2 | H | 3-Cl | 4-Cl | Br | CF3 | 80–81 |

EXAMPLE 10

1-Benzyl-4,5-dibromo-2-(α,α,α-trifluoro-p-tolyl)pyrrole-3-carbonitrile

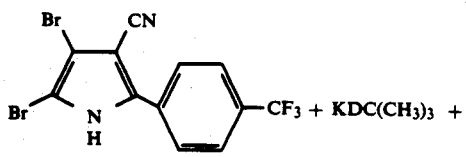

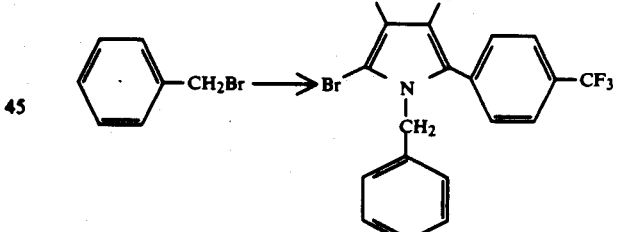

In a 100 mL flask, 1.5 g of 4,5-dibromo-2-(α,α,α-trifluoro-p-tolyl)pyrrole-3-carbonitrile is mixed with 50 mL dry THF to give a clear dark solution. 1 eq of KOtBu is added with stirring. After a few minutes the solution clears. Benzyl bromide (0.65 g) is added by syringe. The mixture is heated at reflux overnight. The following day TLC (50/50 EtOAc/hexane) indicates the presence of both starting material and product. The reaction is worked up in the following manner; 50 mL of water is added and the mixture is extracted with 4×50 mL CHCl3. The organic phases are combined and washed with 4×50 mL 10% aq. NaOH. The organic phase is dried with MgSO4 and stripped. This gives a brown solid which is crystallized from EtOAc/hexane.

Yield = 0.75 g = 40.7%
m.p. = 145–147 deg.C dec.

EXAMPLE 11

4,5-Dichloro-2-(3,4-dichlorophenyl)-1-(ethoxymethyl)-pyrrole-3-carbonitrile

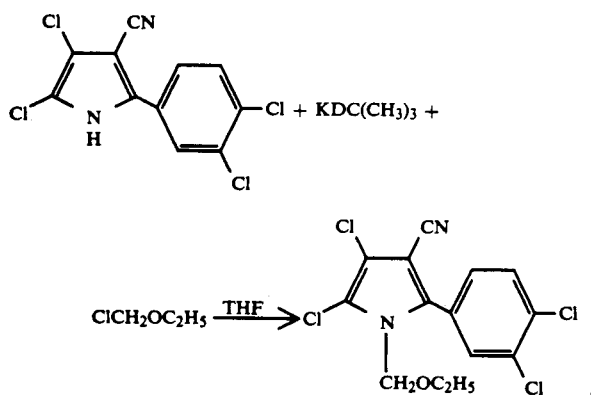

A sample of 4,5-dichloro-2-(3,4-dichlorophenyl)pyrrole-3-carbonitrile (1.0 g, 0.003 mole) is dissolved in 10 mL of dry tetrahydrofuran. To this solution is added potassium t-butoxide (0.37 g, 0.0033 mole) followed by chloromethyl ethyl ether (0.312 g, 0.0033 mole) The mixture is stirred for about 1 hour at room temperature and then poured into a large volume of water precipitating the product. The white solid is collected and dried to give 1.0 g (91%) with m.p. 128°–130°.

EXAMPLE 12

4-Chloro-3-cyano-2-(p-chlorophenyl)pyrrole

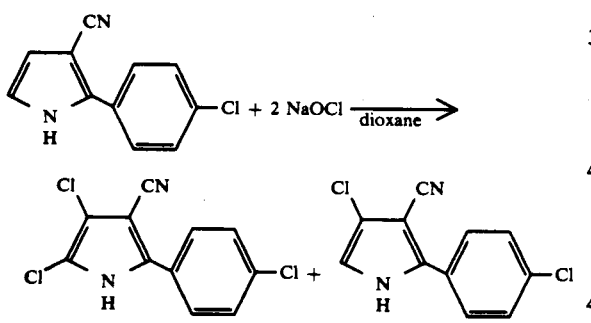

To a magnetically stirred 20° C. solution of 17.87 g (88.2 mmol, 1.00 eq) of 2-(p-chlorophenyl)-3-cyanopyrrole in 800 mL of dioxane is added dropwide 250.15 g (13.13 g real, 176.4 mmol, 2.00 eq) of 5.25 weight % bleach over a period of 30 minutes. After stirring at room temperature for a further 30 minutes, the reaction solution is poured into 2200 mL of water. The resulting mixture is vacuum filtered to remove a small amount of a black solid. The filtrate is acidified to pH 2 with concentrated HCl to produce a brown solid. This solid is vacuum filtered and the collected solids washed with water to give 22.41 g of a brown solid. This solid is treated with 100 mL of 5% aqueous sodium hydroxide to dissolve the bulk of the material while leaving a small amount of undissolved black solid. This black solid, dissolved into 100 mL of ethyl acetate, is washed with 75 mL each of 5% aqueous NaOH, water, and sat. aqueous NaCl. The ethyl acetate layer is dried (MgSO₄), treated with charcoal, filtered, and then rotary evaporated in vacuo to give 1.10 g (5.3% yield) of an orangish brown solid. This solid is recrystallized from an ethyl acetate chloroform mixture to give 0.51 g (2.4% yield) of an off-white solid of 4-chloro-3-cyano-2-(p-chlorophenyl)pyrrole. mp 251°–253.5° C.

EXAMPLE 13

Preparation of 5-bromo-2-(3,4-dichlorophenyl)pyrrole-3-carbonitrile

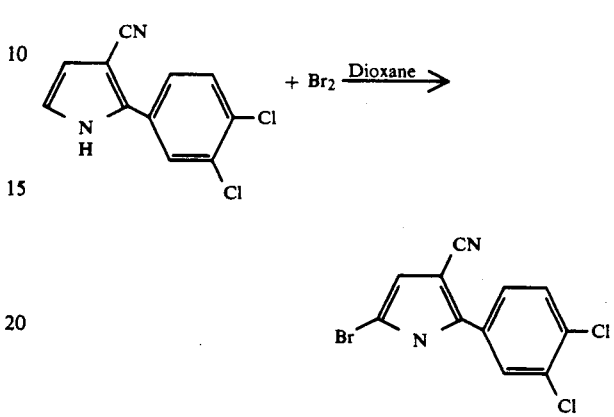

A sample of 2-(3,4-dichlorophenyl)pyrrole-3-carbonitrile (2.0 g., 0.008 mole) is dissolved in 100 mL of dioxane by warming to 40°–50°. Then the solution is cooled to 30° C. and bromine (1.3 g, 0.008 mole) is added. After stirring 1 hour at room temperature the solution is poured into water and a gray solid (2.2 g, 88%) is collected. The mp is 233°–236° C., decomposition.

In a similiar fashion one can prepare 5-bromo-2-(3,4-dichloro)-3-nitropyrrole starting with 2-(3,4-dichlorophenyl)-3-nitropyrrole.

EXAMPLE 14

Preparation of 5-bromo-4-chloro-2-(3,4-dichlorophenyl)pyrrole-3-carbonitrile

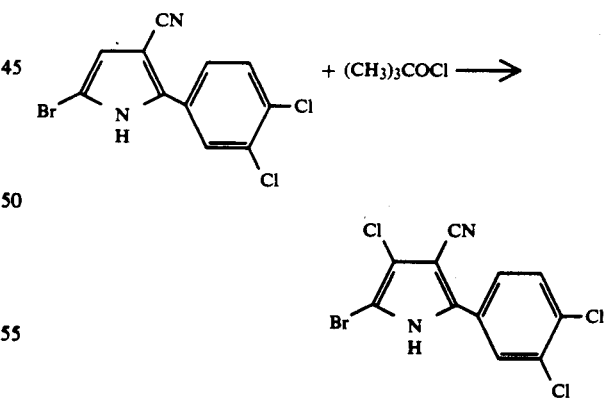

A sample of 5-bromo-2-(3,4-dichlorophenyl)pyrrole-3-carbonitrile (0.158 g, 0.005 mole) is dissolved in tetrahydrofuran (5 mL). An equivalent amount of t-butyl hypochlorite is added and the solution stirred overnight. The solution is poured into water and the precipitate (0.052 g, 30%) is collected. The mp is >275° C. In a similiar fashion one can prepare 2-bromo-3-chloro-5-(3,4-dichlorophenyl)-4-nitropyrrole by starting with 2-bromo-5-(3,4-dichlorophenyl)-4-nitropyrrole.

EXAMPLE 15

Preparation of 5-bromo-4-chloro-2-(p-chlorophenyl)-pyrrole-3-carbonitrile

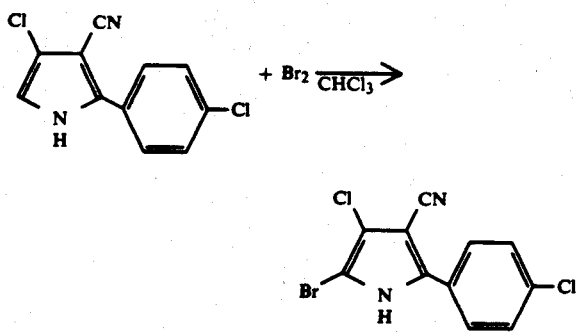

To a magnetically stirred 22° C. solution of 0.17 g (0.67 mmol., 1.00 equivalent) of 4-chloro-2-(p-chlorophenyl)pyrrole-3-carbonitrile in 100 mL of chloroform is added dropwise over a period of 30 minutes, a solution of 0.20 mL (0.62 g, 3.88 mmol., 5.79 equivalent) of bromine in 5 mL of chloroform. The addition produces no exotherm. After stirring at room temperature for 3¼ hours, the clear red reaction solution is evaporated in vacuo to give 0.28 g of an off-white solid. This solid is slurried with a hexane-methylene chloride mixture to give on vacuum filtration 0.23 g of an off-white fluffy solid. mp 262°–263° C.; dec.

EXAMPLE 16

Preparation of 5-chloro-4-bromo-2-(p-chlorophenyl)pyrrole-3-carbonitrile

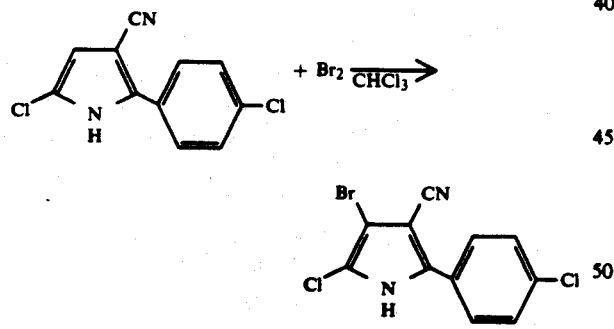

To a magnetically stirred 45° C. solution of 1.00 g (4.22 mmol., 1.00 equivalent) of 5-chloro-2-(p-chlorophenyl)pyrrole-3-carbonitrile in 300 mL of chloroform is added dropwise over a period of 30 minutes, a solution of 0.40 mL (1.24 g, 7.76 mmol., 1.84 equivalent) of bromine in 25 mL of chloroform. The addition produces no exotherm and towards the end of the addition, a small amount of a solid starts to precipitate. After stirring at room temperature for 19¼ hours the reaction mixture is evaporated in vacuo to give 1.49 g of an orangish white solid. This solid is slurried with a hexane-methylene chloride mixture to give on vacuum filtration 1.33 g (100% yield) of a fluffy white solid. mp 250°–258° C., dec.

EXAMPLE 17

Preparation of 5-chloro-2-(p-chlorophenyl)pyrrole-3-carbonitrile

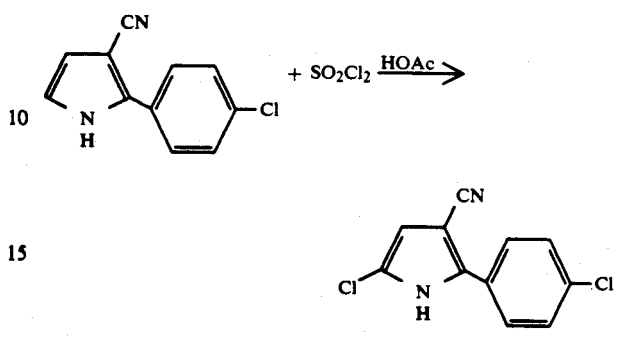

To a 35° C. magnetically stirred solution of 2.40 g (11.8 mmol., 1.00 equivalent) of 2-(p-chlorophenyl)pyrrole-3-carbonitrile, and 65 mL of glacial acetic acid is added dropwise by syringe 0.75 mL (1.26 g, 9.34 mmol., 0.79 equivalent) of sulfuryl chloride over a period of 5 minutes. Approximately 5 minutes after the completion of the addition, a solid precipitated out of the reaction solution. After stirring at room temperature for 45 minutes, the reaction mixture is filtered and the collected solid is washed well with cold acetic acid to give 2.08 g (74% crude yield) of an off-white solid. This solid is recrystallized from 75 mL of hot acetic acid to give 1.63 g (58% yield) of 97 wt % pure. Product mp 258.5°–261° C.

EXAMPLE 18

Preparation of 2-(3,4-dichlorophenyl)-1-methylpyrrole-3-carbonitrile

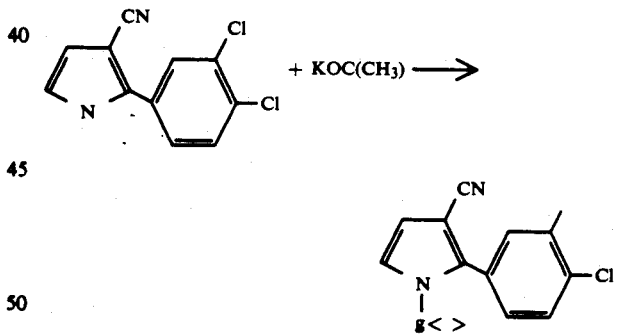

In a 100 mL flask, 2.0 g of 2-(3,4-dichlorophenyl)pyrrole-3-carbonitrile is dissolved in 50 mL of dry THF and 1 equivalent of potassium t-butoxide is added. This gives a slightly cloudy solution. One equivalent of methyl iodide is then added to the mixture by pipette. This leads to a slight lightening of the colour. A drying tube is attached to the flask and it is left to stir at ambient temperature overnight.

The next morning there is a slight light-coloured precipitate in the flask. 50 mL of water is then added and the solution becomes clear before a solid precipitates out of the solution. This solid is filtered out of the solution and compared to the starting material by TLC (25% ethyl acetate/hexane). This indicates a new single spot which is faster moving than the starting material. It is dried in a vacuum oven at 50 deg. C overnight. The product yield is 1.31 g or 62% yield and has a melting point of 140°-142° C.

EXAMPLE 19

Preparation of 4,5-dichloro-2-(3,4-dichlorophenyl)-1-methylpyrrole-3-carbonitrile

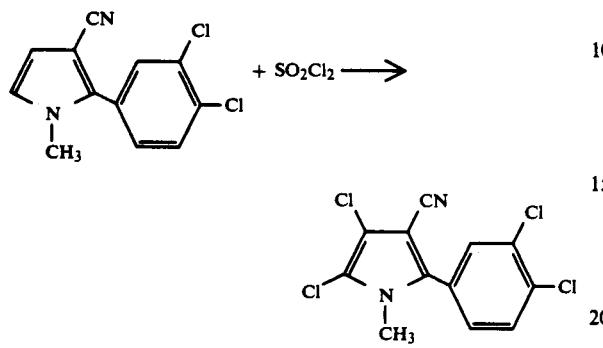

In a 50 mL round bottom flask, 0.5 g of 2-(3,4-dichlorophenyl)-1-methylpyrrole-3-carbonitrile is mixed with 35 mL of glacial acetic acid. The mixture is warmed slightly with a heat gun to dissolve all of the pyrrole.

To this clear solution is added 2 eq. of sulfuryl chloride by pipette. The solution is left to stir at room temperature for 12 hours.

After 12 hours the solution is poured into 50 mL of water, resulting in a white precipitate. This is filtered out and dried in a vacuum oven at 50° C. for 3 hours.

The resulting solid is identical by TLC, (25% ethyl acetate/hexane), and infrared analysis to the product of Example 9. Product yield is 0.36 (56%).

EXAMPLE 20

Preparation of 4,5-Dichloro-2-(3,4-dichlorophenyl)-1-(2-hydroxyethyl)-pyrrole-2-carbonitrile

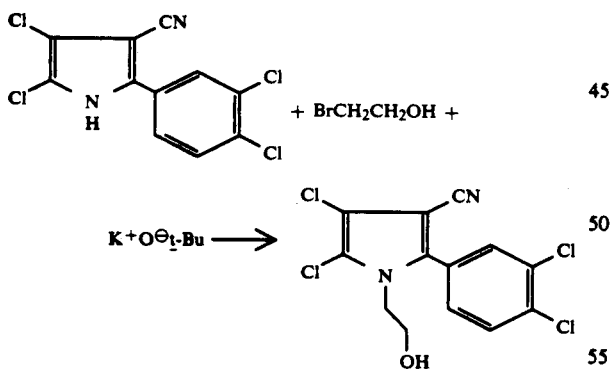

To a stirred mixture of 2.0 g (6.5 mmol) of 4,5-dichloro-2-(3,4-dichlorophenyl)-pyrrole-3-carbonitrile and 0.88 g (7.8 mmol) of potassium tert-butoxide heated at reflux in 50 mL of dioxane is added 0.98 g (7.8 mmol) of bromoethanol. The mixture is stirred at reflux for 12 hours, cooled, diluted with 50 mL of water, and extracted several times with chloroform. The combined chloroform extracts are dried over magnesium sulfate and concentrated in vacuo to leave a solid which, on warming and dissolving in ethyl acetate, deposits on cooling mostly starting pyrrole. Concentration of the mother liquor and recrystallization of the residual solid from 20% ethyl acetate in hexane gives 0.31 g of a white solid, mp 143°-145° C.; IR 5077A.

Anal. Calc'd for $C_{16}H_{23}NO_4$; C, 44.57, H, 2.29; N, 8.00; Cl, 40.57.

Found: (Agm 33139): C, 44.77; H, 2.29; N, 8.06; Cl, 40.14.

EXAMPLE 21

Preparation of 4,5-dichloro-2-(3,4-dichlorophenyl) pyrrole-1,3-dicarbonitrile

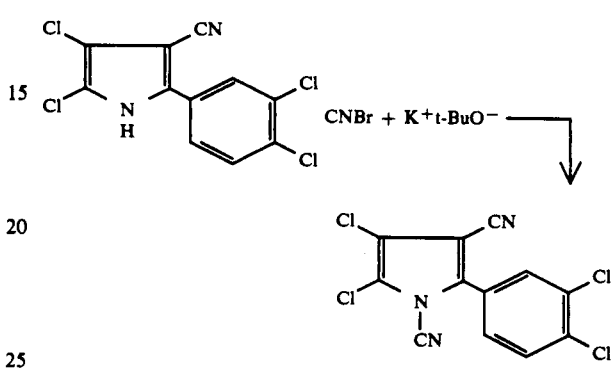

Potassium t-butoxide (617 mg, 55 mmol) is added in portions to a solution of 3-cyano-4,5-dichloro 2-(3,4-dichlorophenyl)pyrrole (1.52 g, 5 mmol) in anhydrous THF (20 mL). After 30 minutes, a solution of cyanogen bromide (583 mg, 5.5 mmol) in THF (1 mL) is added. The reaction mixture is stored at room temperature overnight. The solvent is removed in a rotary evaporator. The residue is treated with water and extracted with ethyl acetate. The organic layer is washed with water and saturated sodium chloride and dried (MgSO$_4$). Evaporation and crystallization of the residue from ethyl acetate gives while crystals (1.07 mp 250.5°-252.0° C.; IR (nujol) 2255, 2245 cm$^{-1}$ (CN); $-C$ NMR (DMSO-$d_6$) 102.7 (N-CN), 113.7 (3-CN); Mass spectrum 331.9 (M+1).

Anal. Calc'd for $C_{12}H_3CP_4N_3$ (330.99); C, 43.54; H, 0.91; N, 12.70; Cl 42.85.

Found: C, 4362; H, 0.93, N, 12.63; Cl 41.95.

EXAMPLE 22

Preparation of 4,5-Dichloro-2-(3,4-dichlorophenyl)-1-(3-iodo-2-propynyl)-pyrrole-3-carbonitrile

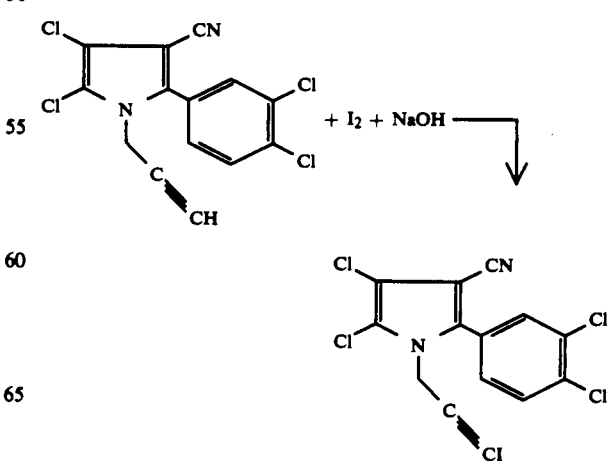

To a stirred mixture of 1.91 g (5.5 mmol) of 4,5-dichloro-2-(3,4-dichlorophenyl)-1-(2-propynyl)pyrrole-3-carbonitrile in 500 mL of methanol is added 69 mL of 10% aqueous sodium hydroxide and then 0.70 g (2.7 mmol) of iodine. The mixture is stirred for 12 hours and then acidified and diluted with 200 mL of water. The precipitated solids are collected and recrystallized from methanol to afford 0.51 g while crystals, m.p. 115°-116° C.

This reaction is also applicable to the conversion of any of the formula III, IV, V, VI or VII substituted N-alkynylarylpyrroles of the present invention to N-substituted 3-iodo-2-propynyl arylpyrroles of said invention.

EXAMPLE 23

Preparation of 2-(3,4-dichlorophenyl)-4,5-diiodopyrrole-3-carbonitrile

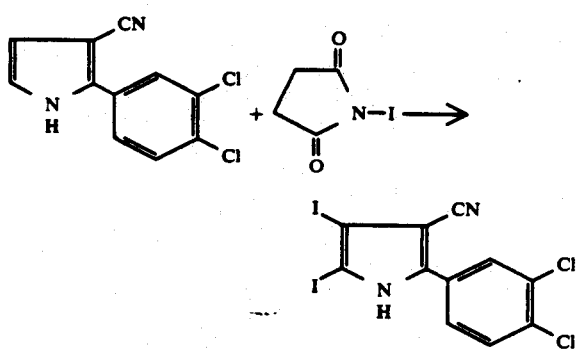

N-iodosuccinimide (5.7 g, 0.0254 mol,) is added slowly to a solution of 2-(3,4-dichlorophenyl)pyrrole-3-carbonitrile (3.0 g, 0.0127 mol) in 100 ml of THF. The reaction is stirred several hours at 25° C. until thin layer chromatography (silica gel; 100:100:1ether:petrolium ether:acetic acid) shows completion. The mixture is evaporated in vacuo to give a residue containing the pyrrole and succinimide. The crude solid is dissolved in 500 mL of ether and shaken with 5×400 mL of water to remove the succinimide. The ether is dried over $Na_2SO_4$ and evaporated in vacuo to leave 2.0 g (32.3%) of a grey-brown solid with mp >230° (loses purple vapors).

EXAMPLE 24

Preparation of 2-phenyl-1-pyrroline-4-carbonitrile

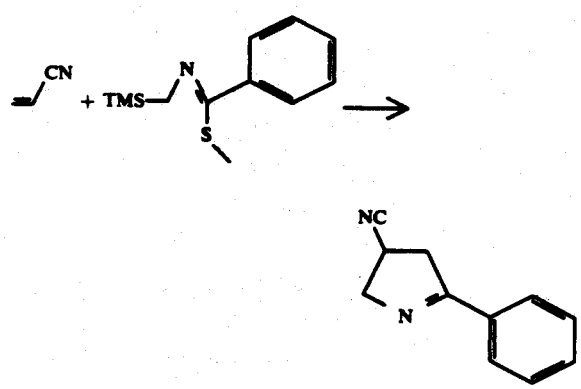

A solution of acrylonitrile (0.65 mL; 0.01 mol) and N-(trimethylsilyl)methyl-S-methyl-benzenethioimidate (2.4 g; 0.01 mol) in THF (100 mL) is cooled to −5° C. in an ice-acetone bath. Under a nitrogen purge, a solution of tetrabutylammonium fluoride (1.0 mL of a 1 N solution in THF) and THF (20 mL) is added dropwise over 30 minutes. The solution is stirred another 30 minutes at −5° C., and then allowed to warm slowly to ambient. Stirring is continued another 18 hours, and then solvent is removed under reduced pressure. The residue is partitioned between ether/water and the water layer extracted with fresh ether. The combined organic layer is washed with water, then saturated sodium chloride. The solution is dried over $MgSO_4$, and cooling the filtrate causes precipitation of an off-white solid (1.2 g; 70% theoretical yield) whose spectral characteristics are identical to the material described by Tsuge [J. Org. Chem. 52, 2523 (1987)].

Calcd. for $C_{11}H_{10}N_2$: C, 77.65; H, 5.88; N, 16.47.
Found: C, 77.55; H, 5.83; N, 16.39. mp=95°-97° C.

EXAMPLE 25

Preparation of 2-phenyl-pyrrole-4-carbonitrile

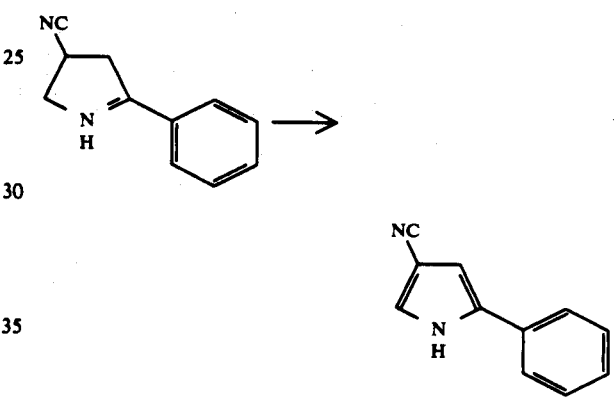

Under a nitrogen purge 2,3-dichloro-5,6-dicyano-1,4-bonzoquinone (0.23 g; 0.001 mol) and 2-phenyl-1-pyrroline-4-carbonitrile (0.17 g; 0.001 mol) is dissolved in 1,2-dimethoxyethane (13 mL) to form a clear orange solution. Pyridine (0.08 mL; 0,001 mol) is added in a single portion, causing a slight exotherm (to ca. 28° C.) and an immediate formation of a green/grey precipitate. The suspension is stirred at room temperature for 18 hours during which time much of the solvent evaporates. The brownish semi-solid residue is partitioned between ether and a half-saturated solution of sodium carbonate. The red-brown aqueous layer is extracted twice with ether and the combined ether layer is washed with fresh water, then saturated sodium chloride. After drying with $MgSO_4$, solvent is removed under reduced pressure to obtain a white semi-solid. This material was recrystallized from ethylene dichloride (DARCO treatment) to yield lavender crystals (0.1 g).

The identical product is obtained directly in a single step by condensing α-chloroacrylonitrile and N-(trimethylsilyl)methyl-S-methyl-benzenethioimidate using tetrabutylammonium fluoride catalysis (analogous to the preparation of 2-phenyl-1-pyrroline-4-carbonitrile described previously).

Calcd. for $C_{11}H_8N_2$: C, 78.57, H, 4.76; N, 16.67.
Found: C, 78.65; H, 4.70; N, 16.43. m.p.−155°-158° C.

EXAMPLE 26

Preparation of 2,4-dibromo-5-phenyl pyrrole-3-carbonitrile

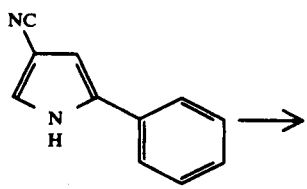

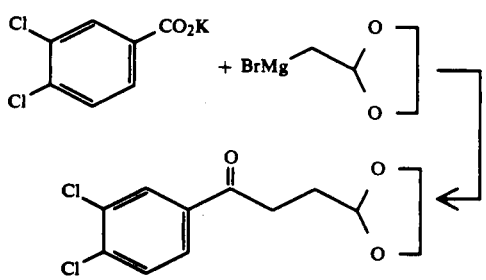

Under a nitrogen purge, a solution of bromine (0.6 mL; 0.012 mol) in CHCl$_3$ (5 mL) is added dropwise over 20 minutes to a stirring solution of 2-phenyl-pyrrole-4-carbonitrile (0.84 g; 0.05 mol) in CHCl$_3$ (20 mL). The resulting solution is stirred 18 hours at room temperature, then solvent is removed under reduced pressure to obtain a solid which is recrystallized from C$_2$H$_4$Cl$_2$ (DARCO treatment), yielding the desired final product (0.6 g), m.p.=239°-242° C.

Calcd. for C$_{11}$H$_6$Br$_2$N$_2$: C, 40.49; H, 1.84; Br, 49.08; N, 8.59.

Found: C, 39.88; H, 1.87; Br, 48.81; N, 8.48.

By the procedure described in Example 24, 25 and 26, 2,4-dibromo-5-(p-chlorophenyl)pyrrole-3-carbonitrile, m.p. 270°-272° C. (dec.) is also prepared.

EXAMPLE 27

3',4'-Dichloro-3-(1,3-dioxolan-2-yl)-propiophenone

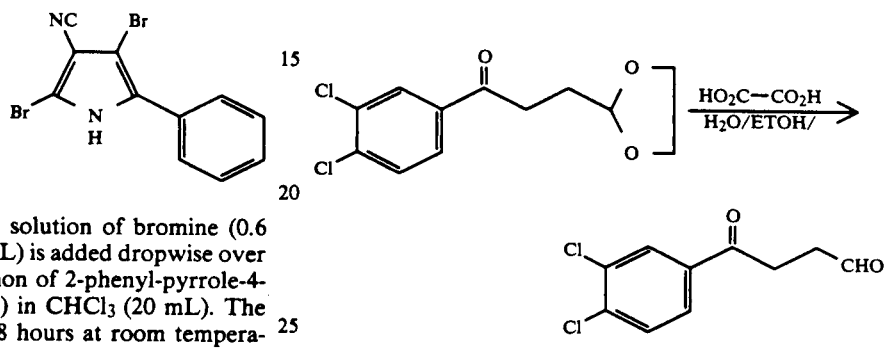

To a rapidly stirring mixture of magnesium turnings (0.64 g, 26 mmol) in 10 mL of tetrahydrofuran at 25° C. in a 100 mL three-neck round bottom flask equipped with a thermometer, a 60 mL addition funnel, and a nitrogen inlet is added dropwise 2-(2-bromoethyl)-1,3-dioxolane (4.7 g, 26 mmol) in 40 mL of tetrahydrofuran. The rate of addition is adjusted so as to maintain the reaction temperature below 50° C. The reaction is then allowed to stir for 1 hour at 25° C. 120 mL of tetrahydrofuran is mixed with potassium 3,4-dichlorobenzoate (5.0 g, 22 mmol) under a blanket of nitrogen. The Grignard solution is then quickly decanted away from the unreacted magnesium turnings, and added dropwise to the rapidly stirring potassium benzoate suspension. The reaction is then allowed to stir for 24 hours at 25° C. Fifty mL of diethyl ether and 15 mL of 3 N hydrochloric acid are added to the reaction mixture and the layers separated. The organic layer is washed with saturated aqueous sodium bicarbonate until neutral followed by one washing with 10 mL of brine. Drying over sodium sulfate, and rotary evaporation yields a beige semisolid which is chromatographed over silica gel using 3:1 hexane-ethyl acetate as eluent to give the keto-acetal (4.3 g, 60%) as a white solid, m.p. 115°-117° C.

EXAMPLE 28

Preparation of 3-(3,4-dichlorobenzoyl)propionaldehyde

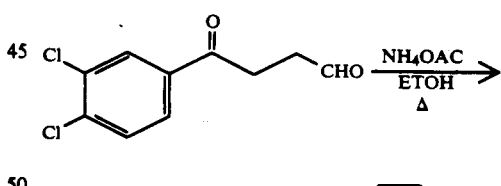

Ten grams (26 mmol) of 3',4'-dichloro-3-(1,3-dioxolan-2-yl)-propiophenone is added to 30 mL of 0.2 M oxalic acid (made by dissolving 0.9 g of oxalic acid dihydrate in 30 mL of water) and 5 mL of ethanol. The mixture is refluxed for 1 hour and then allowed to cool. Most of the ethanol is rotary evaporated off and 100 mL of diethyl ether is added along with 20 mL of saturated aqueous sodium bicarbonate. The layers are separated and the organic phase is dried over magnesium sulfate. Rotary evaporation yields a viscous yellow oil which is chromatographed over silica gel using 3:1 hexane-ethyl acetate to give the keto-aldehyde (6.3 g, as a white solid.

EXAMPLE 29

Preparation of 2-(3,4-dichlorophenyl)pyrrole

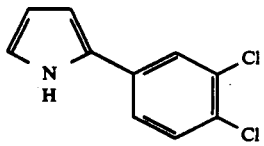

To a suspension of 3-(3,4-dichlorobenzoyl) propionaldehyde (6 g, 26 mmol) in 60 mL of absolute ethanol is added ammonium acetate (4 g, 52 mmol). The reaction is refluxed for 20 minutes and allowed to cool. Most of the ethanol is rotary evaporated and 200 mL of 1:1 dichloromethane-diethyl ether along with 50 mL of water is added. The layers are separated and the organic phase is dried over sodium sulfate. Rotary evaporation yields a dark brown oil which is chromatographed over silica gel using 3:1 hexane-ethyl acetate as eluent to give the pyrrole (4.6 g, 83%) as a light brown solid, m.p. 49°-51° C.

EXAMPLE 30

Preparation of 5-(3,4-dichlorophenyl)pyrrole-2-carboxaldehyde

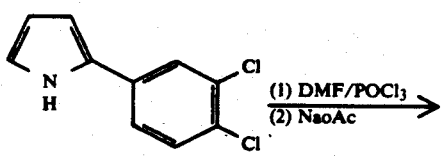

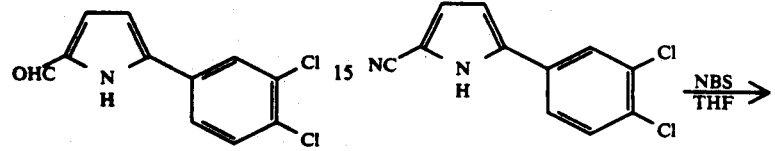

To 10 mL of dimethylformamide stirring under nitrogen in a 50 mL round bottom flask is added phosphorus oxychloride (0.6 mL, 6.5 mmol) dropwise via syringe. The solution, warms and becomes light yellow in color. It is allowed to stir for 20 minutes before the portionwise addition of 2-(3,4-dichlorophenyl)pyrrole (1 g, 4.7 mmol). The beige suspension which results is allowed to stir for 30 minutes before being heated to 50° C. for 40 minutes. A solution of sodium acetate (10 g, 122 mmol) in 15 mL of water is added to the cooled reaction which is then allowed to stir for 20 minutes. A beige precipitate is filtered off from the reaction mixture and air-dried for 20 hours to give the essentially pure aldehyde (1.1 g, 95%), mp >200° C.

EXAMPLE 31

Preparation of 5-(3,4-dichlorophenyl)pyrrole-2-carbonitrile

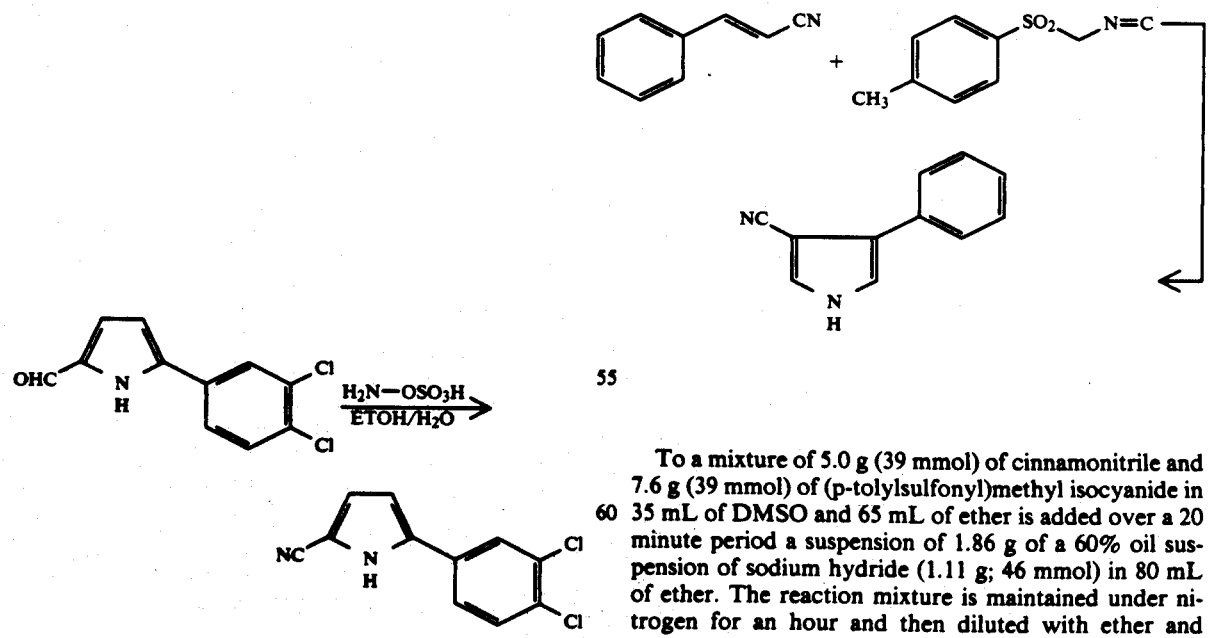

To a suspension of 5-(3,4-dichlorophenyl)pyrrole-2-carboxaldehyde (1.5 g, 6.2 mmol) in 20 mL of water and 20 mL of ethanol, is added hydroxylamine-O-sulfonic acid (0.7 g, 6.2 mmol). The reaction is refluxed for 1 hour during which time a gray precipitate appears. After being allowed to cool, the reaction is filtered to give essentially pure nitrile (1.5 g, 99%) as a gray solid, m.p. 170°–171° C.

EXAMPLE 32

Preparation of 3,4-dibromo-5-(3,4-dichlorophenyl)pyrrole-2-carbonitrile

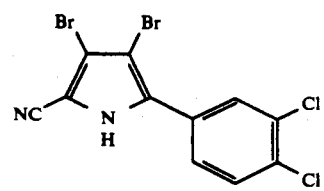

To a solution of 5-(3,4-dichlorophenyl)pyrrole-2-carbonitrile (0.5 g, 2.1 mmol) in 20 mL of tetrahydrofuran under nitrogen is added portionwise N-bromo-succinimide (0.8 g, 4.2 mmol). The reaction is stirred at 25° C. for 30 minutes before the addition of 10 mL of water and 40 mL of diethyl ether. The layers are separated and the organic layer dried over sodium sulfate. Rotary evaporation is followed by chromatography over silica gel using 3:1 hexane-ethyl acetate as eluent to afford the dibromopyrrole (0.5 g, 60%) as a brown solid, m.p. >250° C.

EXAMPLE 33

Preparation of 4-phenylpyrrole-3-carbonitrile

To a mixture of 5.0 g (39 mmol) of cinnamonitrile and 7.6 g (39 mmol) of (p-tolylsulfonyl)methyl isocyanide in 35 mL of DMSO and 65 mL of ether is added over a 20 minute period a suspension of 1.86 g of a 60% oil suspension of sodium hydride (1.11 g; 46 mmol) in 80 mL of ether. The reaction mixture is maintained under nitrogen for an hour and then diluted with ether and water. The ether layer is separated, dried over magnesium sulfate, and concentrated in vacuo. The resulting oil is chromatographed on silica gel using 1:1 chloroform ethyl acetate to give 2.5 g of cream-colored solids.

Recrystallization from etherhexane affords 1.15 g, m.p. 123°–125° C.; NMR M86-1077.

Lit.: Tet. Letters 5337 (1972: m.p. 128°–129° C.

EXAMPLE 34

Preparation of 2,5-dichloro-4-phenylpyrrole-3-carbonitrile

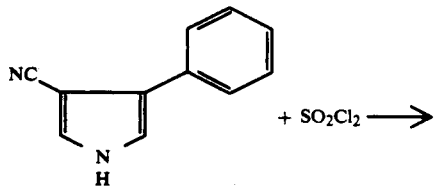

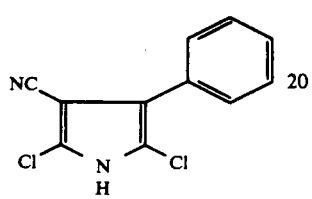

2,6-dibromo-4-(p-chlorophenyl)pyrrole-3-carbonitrile, the procedure of Example 33 is followed using bromine in dioxane to replace sulfuryl chloride and tetrahydrofuran.

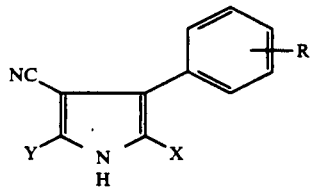

| R | X | Y | m.p. °C. |
|---|---|---|---|
| 4-Cl | Cl | Cl | 237–240 (dec.) |
| 4-CH$_3$ | Cl | Cl | 103–206 |
| 4-Cl | Br | Br | >245° |

EXAMPLE 35

Ethyl 4-(p-chlorophenyl)-pyrrole-3-carboxylate

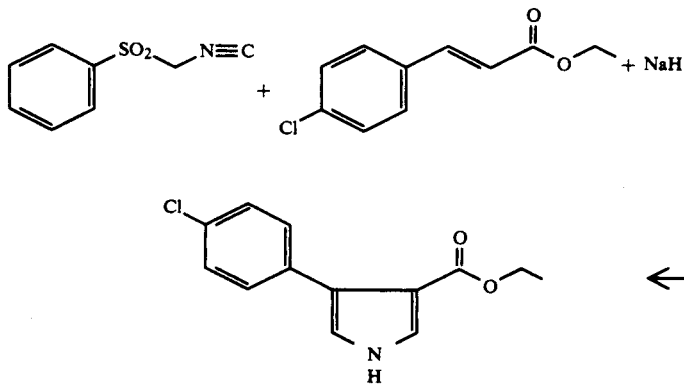

To a stirred mixture of 0.66 g (3.9 mmol) of 4-phenyl-pyrrole-3-carbonitrile in 20 mL of dry THF cooled to 6° C. with an ice-water bath is added from a syringe 0.66 mL (1.11 g; 8.2 mmol) of sulfuryl chloride over a 4 minute period. The mixture is maintained at 5°–10° C. for an additional 45 minutes and then stirred an additional 30 minutes with the ice bath removed. After the reaction mixture is poured into 80 mL of ethyl acetate and 40 mL of water, the organic phase is separated, washed with water, and dried over sodium sulfate. Filtration through a short column of silica gel, rinsing with ethyl acetate, and concentration of the combined filtrated in vacuo gives 0.95 g of dark solid. Recrystallization from chloroform gives 0.42 g of off-white crystals, m.p. 195°–196° C. (dec.).

Anal. Calcd for C$_{11}$H$_6$Cl$_2$N$_2$: C, 55.72; H, 2.55; N, 11.82; Cl, 29.91.

Found: C, 55.66; H, 2.65; N, 11.69; Cl, 29.97.

Following the procedures of Examples 33 and 34, the following analogs are prepared. For the synthesis of To a mixture of 5.63 g of a 60% sodium hydride/oil suspension in 200 mL of dry ether under nitrogen is added from an additional funnel a mixture of 23.5 g (122 mmol) of ethyl p-chlorocinnamate and 19.4 g (122 mmol) of (p-tolylsulfonyl)methyl isocyanide in solution in 180 mL of ether and 80 mL of dimethylsulfonide. The addition time is about 20 minutes and results in gentle refluxing of the mixture. After another 10 minutes stirring, the mixture is diluted with 100 mL of water. The mixture is extracted four times with ether which is then dried over magnessium sulfate followed by concentrated in vacuo. The resulting solid is recrystallized from ethylene dichlorite to give 7.8 g of crystals, m.p. 137°–138° C.

Anal. Calcd for C$_{13}$H$_{12}$ClNO$_2$: C, 62.53; H, 4.81; N, 5.61; Cl, 14.23.

Found: C, 61.31; H, 5.12; N, 5.32; Cl, 14.57.

Concentration of the mother liquor for the crystallization leaves additional crude ester which is carried on to the saponification step.

EXAMPLE 36

Preparation of 3-(p-chlorophenyl)-pyrrole

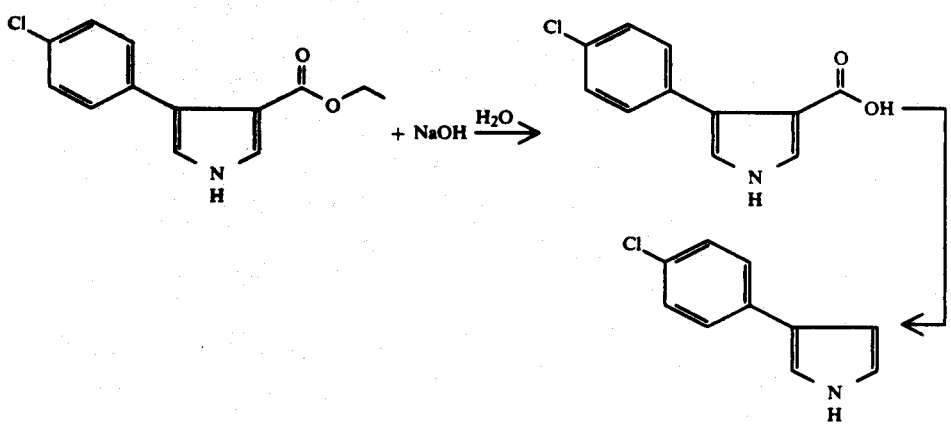

A mixture of 22.0 g of crude ethyl 4-(p-chlorophenyl)-pyrrole-3-carboxylate from the recrystallization mother liquor and the recrystallized product from the previous step is stirred at reflux with 150 mL of 10% aqueous sodium hydroxide for 2.5 hours. The mixture is cooled, extracted with ether, and acidified to give a precipitate which on collection and drying weighs 11.6 g.

A mixture of 10.5 g of the acid in 100 mL of β-ethanolamine is heated at reflux for three hours. After cooling, the mixture is poured over 400 mL of ice and the resulting mixture is extracted four times with chloroform. The chloroform solution, after drying over magnesium sulfate and treatment with activated charcoal, is concentrated in vacuo to leave a brown solid. Chromatography on silica gel using 1:1 ethyl acetate hexane gives 4.0 g of a white solid, m.p. 117°-118° C.

EXAMPLE 37

Preparation of 3-(p-chlorophenyl)-pyrrole-2-caboxaldehyde

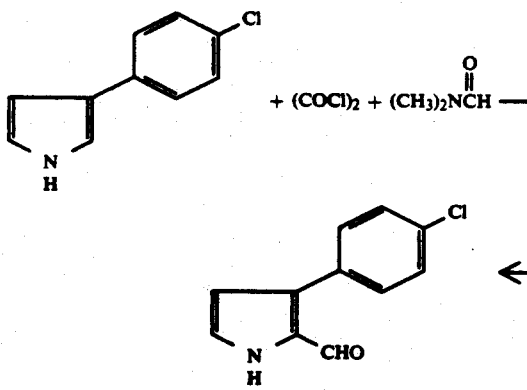

To a mixture of 0.86 g (12 mmol) of dimethylformamide in 10 mL of ethylene dichloride maintained under nitrogen and cooled in an ice bath is added 1.49 g (12 mmol) of oxalyl chloride in 10 mL of ethylene dichloride over a period of 25 minutes. The ice bath is removed, the mixture is stirred an additional 15 minutes and recooled in an ice bath. To this mixture is added 1.5 g (8.5 mmol) of 3-(p-chlorophenyl)-pyrrole in 25 mL of ethylene dichloride over a 20 minute period. The ice bath is removed and after an additional 30 minutes of stirring, the mixture is poured into 50 mL of ice-water and 6 mL of 50% sodium hydroxide. The resulting mixture is extracted with ether and with chloroform and the combined organic mixture is dried over magnesium sulfate and concentrated in vacuo. Purification of the resulting solid by chromatography on silica gel using 1:1 ethyl acetate hexane gives 0.63 g of off-white solid which is used directly for conversion to 3-(p-chlorophenyl)-pyrrole-2-carbonitrile.

EXAMPLE 38

Preparation of 3-(p-chlorophenyl)-pyrrole-2-carbonitrile

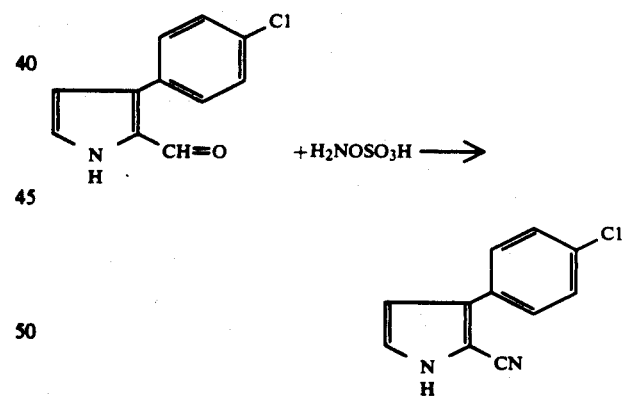

A mixture of 0.63 g (3.1 mmol) of 3-(p-chlorophenyl)-pyrrole-2-carboxaldehyde in 10 mL of water is stirred and ice-cooled while 0.52 g (4.6 mmol) of hydroxylamine-O-sulfonic acid in 10 mL of water is slowly added. After the addition, the cooling bath is removed and the mixture is heated for 25 minutes. On cooling, the resulting solid is collected and shown, by NMR, to be a mixture of product and starting aldehyde. This mixture is reacted in the same manner with an additional 0.49 g (4.2 mmol) of hydroxylamine-O-sulfonic acid in a total of 30 mL of water. The mixture is heated at 60°-70° C. for 2 hours. The mixture is cooled and the resulting solids are collected and purified by chromatography or silica gel using 1:1 ethyl acetate hexane to give 0.40 g of pink solid, m.p. 114°-115° C.

EXAMPLE 39

Preparation of
4,5-Dibromo-3-(p-chlorophenyl)-pyrrole-2-carbonitrile

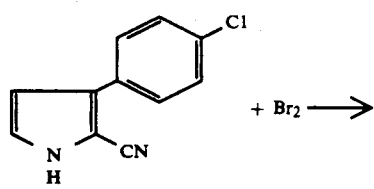
+ Br₂ →

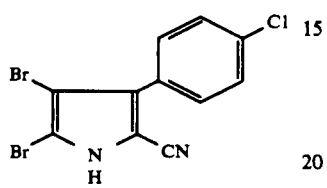

To a mixture 0.40 g (2.0 mmol) of 3-(p-chlorophenyl-pyrrole)-2-carbonitrile in 25 mL of chloroform is added 0.63 g (4.0 mmol) of bromine. After 20 minutes, the precipitate which forms is collected and recrystallized from ethyl acetate to give 0.21 g of pink crystals, m.p. >250° C.

Anal. Calcd for $C_{11}H_5Br_2ClN$: C, 36.62; H, 1.39; Br, 44.38; Cl, 9.85; N, 7.77.

Found: C, 36.92; H, 1.32; Br, 44.62; Cl, 9.88; N, 7.50

EXAMPLE 40

Preparation of Ethyl
5-bromo-4-(p-chlorophenyl)pyrrole-3-carboxylate

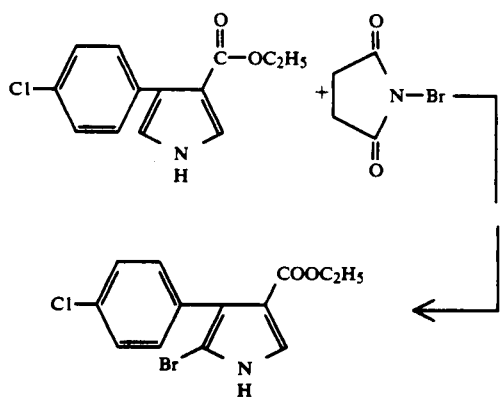

Ethyl 4-(p-chlorophenyl)pyrrole-3-carboxylate (1.6 g., 0.0064 mmol) is dissolved in tetrahydrofuran (40 mL) N-bromosuccinimide (1.14 g., 0.0064 mmol) is added in small portions at 25°-28° C. After the addition is complete, the solution is stirred overnight at room temperature. The solution is concentrated in vacuo and the solid residue partioned between water and ether. The ether layer is separated and dried over magnesium sulfate. Work-up of the ether extract leaves 1.9 g (90%) of a white solid which is purified by stirring with a mixture of 80/20 hexane/ethyl acetate. The insoluble solid (1.3 g, 62%) is collected and has m.p. 161°-164° C.

Calcd for $C_{13}H_{11}BrClNO_2$: C, 47.50; H, 3.34; N, 4.26; Br, 24.33; Cl, 10.80.

Found: C, 47.39; H, 3.38; N, 4.12; Br, 24.29; Cl, 10.77

EXAMPLE 41

Preparation of
5-bromo-4-(p-chlorophenyl)pyrrole-3-carboxylic acid

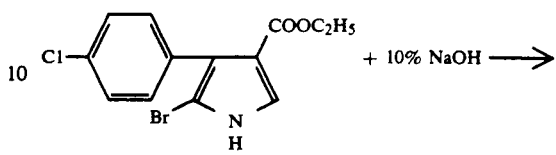
+ 10% NaOH →

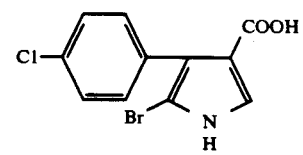

Ethyl 5-bromo-4-(p-chlorophenyl)pyrrole-3-carboxylate (15 g., 0.045 mmol) is added to 200 mL of 10% sodium hydroxide and the slurry heated to reflux. After everything appears to dissolve the mixture is refluxed an additional 40 minutes. The mixture is cooled, filtered and the filtrate acidified. The white precipitate (8.0 g, 58%) is collected and dried. The solid has m.p. >205° C. and an NMR (d₆-DMSO) which showed a pyrrole proton at 7.52 (d). The mass spectrum is also consistent for a monobrominated compound.

EXAMPLE 42

Preparation of 2-bromo-3-(p-chlorophenyl)pyrrole

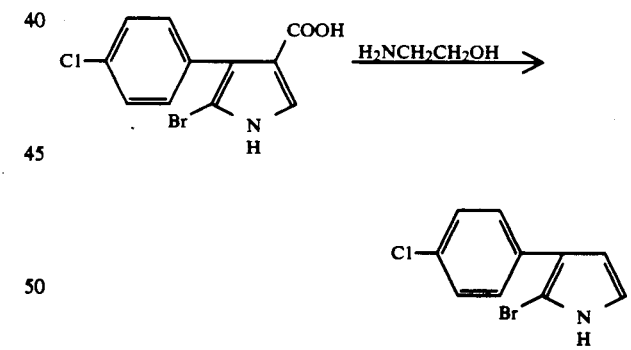

5-bromo-4-(p-chlorophenyl)pyrrole-3-carboxylic acid (8.0 g., 0.026 mmol) is added to aminoethanol (24 mL) and the slurry slowly warmed to 110°-120° C. and held at that temperature for 1 hour. The solution is cooled and poured into water and extracted with ether. The ether extract, by thin layer chromatography (75/25, hexane/ethyl acetate), shows a major fast moving spot and a slower moving minor component. Work-up of the ether leaves a dark solid (4.0 g., 56%) which is 2-bromo-3-(p-chlorophenyl)pyrrole and is used immediately to prepare 5-bromo-4-(p-chlorophenyl)pyrrole-2-carbonitrile.

EXAMPLE 43

Preparation of
5-bromo-4-(p-chlorophenyl)pyrrole-2-carbonitrile

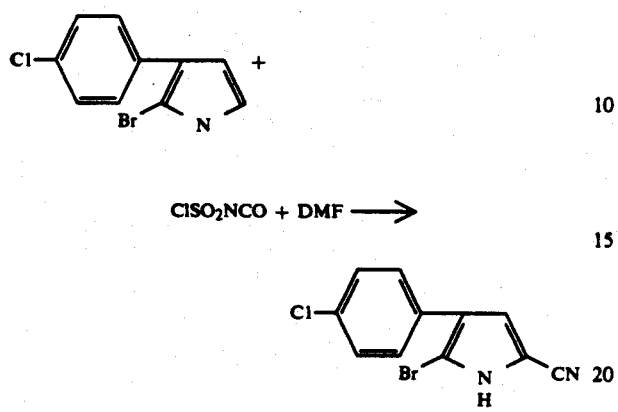

A freshly prepared sample of 2-bromo-3-(p-chlorophenyl)pyrrole (4.0 g., 0.015 mmol) is dissolved in dry dimethoxyethane (25 mL). Then while holding the temperature below 25° C., chlorosulfonyl isocyanate (3.08 g., 0.022 mmol) is added. After stirring overnight, the solution is treated with dimethylformamide (6 mL) and stirred for 3 hours. Finally, the solution is poured into water precipitating a brown solid (3.8 g, 90%). Dry column chromatography (80/20 hexane/ethyl acetate) yields 1.4 g (33%) of white solid with m.p. 202°-204° C.

Calcd for $C_{11}H_6BrClN_2$: C, 46.90; H, 2.13; N, 9.95; Cl, 12.61; Br, 28.39.

Found: C, 47.20; H, 2.09; N, 9.80; Cl, 12.36; Br, 27.42.

EXAMPLE 44

Preparation of
3,5-Dibromo-4-(p-chlorophenyl)pyrrole-2-carbonitrile

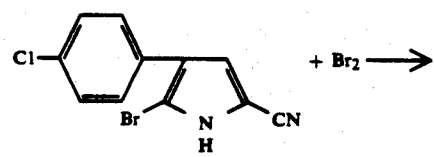

A sample of 5-bromo-4-(p-chlorophenyl)pyrrole-2-carbonitrile (2.2 g., 0.0078 mol) is dissolved in 30 mL of dry dioxane. The solution is heated with bromine (1.3 g., 0.008 mol) in dioxane (20 mL) and then stirred overnight at room temperature. The reaction mixture is poured into water precipitating a tan solid (2.6 g., 92%). A portion (1.6 g) is purified by flash chromatography using 75/25 hexane/ethyl acetate to give 0.8 g of grey solid with m.p. 191°-194° C.

Calcd for $C_{11}H_5Br_2ClN_2$: C, 36.61; H, 1.38; N, 7.76; Cl, 9.84; Br, 44.3.

Found: C, 37.46; H, 1.25; N, 7.41; Cl, 9.53; Br, 42.99.

EXAMPLE 45

Preparation of 3-(3,4-dichlorophenyl)-4-nitropyrrole

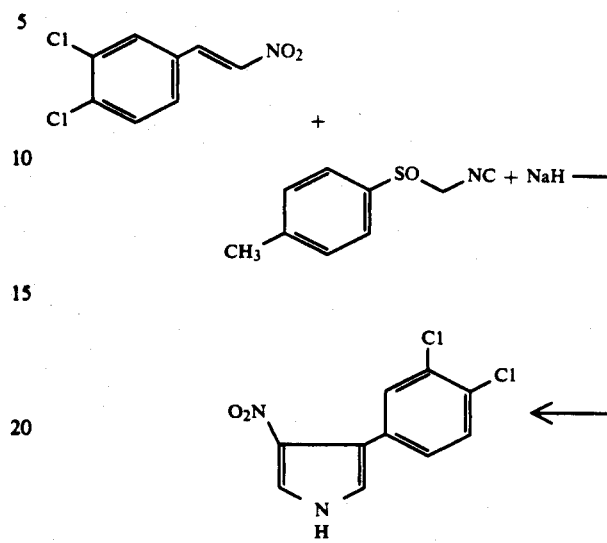

Sodium hydride (2.66 g of a 60% suspension in oil is rinsed with dry ether; 66 mmol) and suspended in 150 mL of dry ether. To this mixture is added over 15 minutes a mixture of 12.0 g (5.5 mmol) of 3,4-dichloro-β-nitrostyrene and 10.8 g (5.5 mmol) of (p-tolylsulfonyl)-methyl isocyanide in 50 mL of DMSO and 150 mL of ether. The mixture is stirred for 1.5 hours and then diluted with 150-200 mL of water and additional ether. The ether layer is separated, dried over magnesium sulfate, and concentrated in vacuo. The resulting 10.6 g of crude product is purified by chromatography on silica gel using a 4:1 mixture of chloroform and ethyl acetate. A 7.2 g solid fraction is recrystallized from chloroform-ethyl acetate-hexane to give 3.0 g of yellow solid, m.p. 187°-188° C. (dec.).

Anal. Calcd for $C_{10}H_6Cl_2N_2O_2$: C, 46.72; H, 2.35; N, 10.90.

Found: C, 46.96; H, 2.60; N, 9.77

EXAMPLE 46

Preparation of
2,5-Dichloro-3-(3,4-dichlorophenyl)-4-nitropyrrole

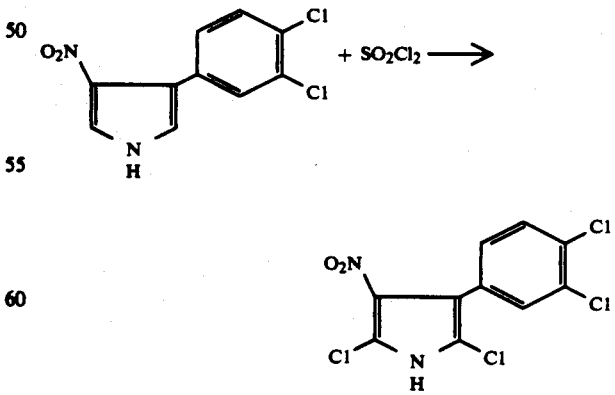

To a mixture of 3-(3,4-dichlorophenyl)-4-nitropyrrole (2.5 g, 9.7 mmol) warmed to about 40° C. in 200 mL of chloroform is added over one minute 2.95 g (22 mmol) of sulfuryl chloride. After another hour, the mixture is diluted with 100 mL of saturated sodium bicarbonate solution and 300 mL of ether. The organic layer is separated and dried over magnesium sulfate. Concentration, in vacuo, leaves a brown solid which is chromatographed on silica gel using 4:1 chloroform ethyl acetate. An orange solid fraction is recrystallized from chloroform and then rechromagraphed on silica gel using 4:1 chloroform ethyl acetate to yield 0.36 g of yellow solid, m.p. 193°–194° C.

Also prepared by procedure of Examples 45 and 46 above is 2,5-dichloro-3-nitro-4-phenylpyrrole, m.p. 193°–194° C.(dec.).

EXAMPLE 47

Preparation of
5-(p-chlorophenyl)pyrrole-2,4-dicarbonitrile

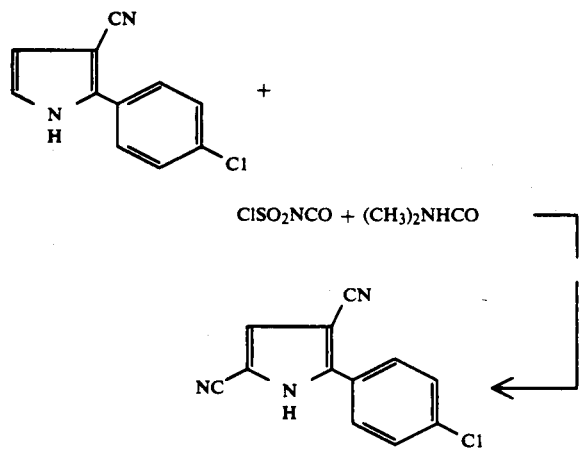

A sample of 2-p-chlorophenyl-3-cyanopyrrole, prepared by the method of Example 4, (3.0 g, 0.015 mole) is dissolved in 50 mL of dry dimethoxyethane. To this solution is added chlorosulfonyl isocyanate (3.39 g, 0.024 mole). The addition is exothermic and some cooling is necessary. After stirring 3 hours at room temperature, dimethylformamide (6–7 mL) is added and the solution is stirred 4 hours more. The solution is then poured into water precipitating a white solid (3.4 g, 100%). A sample (1.0 g) is purified by dissolving in ethyl acetate and then passing the solution through a 60 mL course filter funnel packed with silica gel. The filtrate is concentrated to yield 0.7 g of a white solid with m.p. 235°–240° C.

Following the procedure of Example 47, the following analogs are prepared:

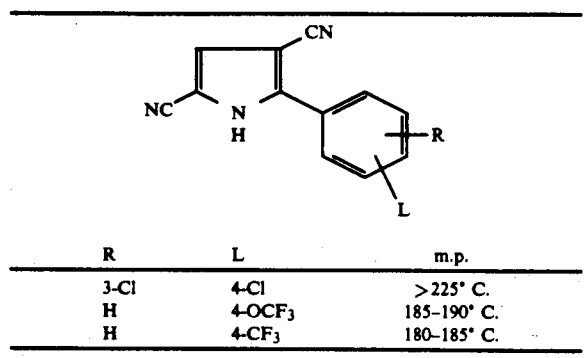

| R    | L     | m.p.      |
|------|-------|-----------|
| 3-Cl | 4-Cl  | >225° C.  |
| H    | 4-OCF3 | 185–190° C. |
| H    | 4-CF3 | 180–185° C. |

EXAMPLE 48

Preparation of
3-Bromo-5-(p-chlorophenyl)pyrrole-2,4-dicarbonitrile

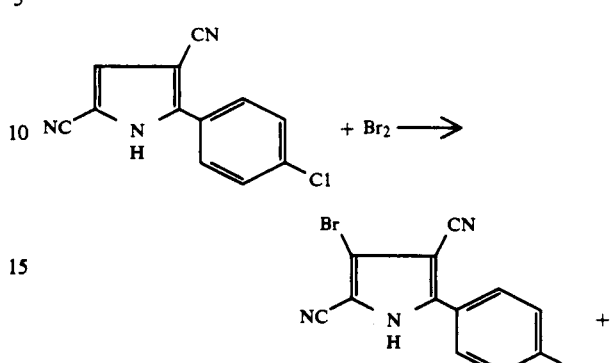

A sample of 5-(p-chlorophenyl)pyrrole-2,4-dicarbonitrile (1.0 g, 0.004 mole) is dissolved in 20 mL of dioxane and a solution of bromine (0.8 g, 0.005 mole) in dioxane (10 mL) is then added thereto. THe solution is stirred several hours at room temperature and then poured into water precipitating a white solid (1.2 g, 100%). The solid has a m.p. >225° C. and a mass spectrum of a sample gives a pattern consistent with the desired structure.

Following the procedure set forth above in Example 48, the following additional compounds are prepared:

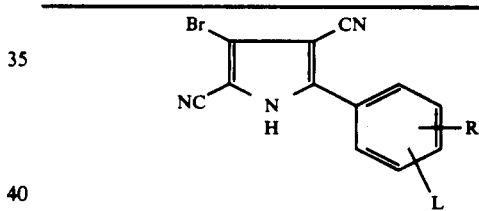

| R    | L     | m.p.      |
|------|-------|-----------|
| 3-Cl | 4-Cl  | >250° C.  |
| H    | 4-OCF3 | 218–233° C. |
| H    | 4-CF3 | 239–241° C. |

EXAMPLE 49

Preparation of bromofumaronitrile

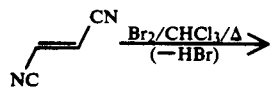

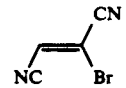

Under a nitrogen purge, fumaronitrile (15.6 g; 0.2 mol) in CHCl3 (150 mL) is heated to reflux, resulting in a clear solution. A solution of bromine (5.3 mL; 0.2 mol) in CHCl3 (25 mL) is added dropwise over 30 minutes, resulting in a slow decolorization and acidic (pH test paper) fumes being released. The solution is refluxed another 90 minutes, during which time most of the color has been discharged. The solution is cooled and solvent is removed under reduced pressure, leaving an amber oil (weight approximately theoretical for bromofumaronitrile). The oil is subjected to bulb-to-bulb distillation (0.2 mm Hg), maintaining the temperature below 120° C. (above that point, a rapid decomposition of material occurs). A semi-solid is obtained which slowly forms a waxy, amber solid, m.p. −43°-47° C.

Calcd for $C_4HBrN$: C, 30.57; H, 0.64; N, 17.83.
Found: C, 29.13; H, 0.75; N, 16.94.

EXAMPLE 50

Preparation of 2-phenyl-pyrrole-3,4-dicarbonitrile

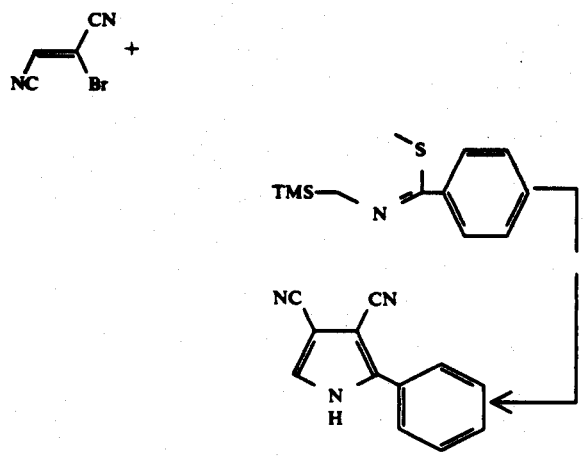

Under a nitrogen purge, a solution of bromofumaronitrile (4.7 g; 0.03 mol) and N-(trimethylsilyl) methyl-S-methyl-benzene-thioimidate (7.1 g; 0.03 mol) in hexamethylphosphoramide (HMPA) (35 mL) is stirred at room temperature. In a single portion, water (1.6 mL); 0.09 mol) is added, washed in with HMPA (10 mL). The solution almost immediately begins to exotherm, the temperature rapidly reaching 100° C. before subsiding. The resulting dark red solution is allowed to stir at ambient temperature 20 hours. Pouring the reaction mixture onto an ice/water mixture results in a gummy material which slowly yields a discreet beige solid. This material is collected by filtration and washed with cold water and dried on the filter. After further drying (vacuum oven; 60° C.), the material is twice recrystallized from $C_2H_4Cl_2$ (DARCO treatment) to yield a white powder.

Calcd for $C_{12}H_7N_3$: C, 74.61; H, 3.63; N, 21.76.
Found: C, 74.45; H, 3.84; N, 21.61. m.p.=197°-200° C.

EXAMPLE 51

Preparation of 2-bromo-5-phenylpyrrole-3,4-dicarbonitrile

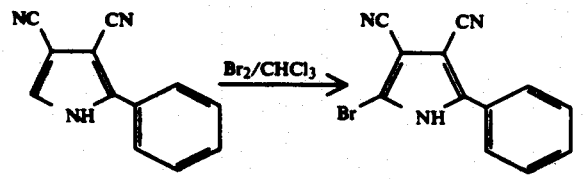

Under a nitrogen purge, 2-phenyl-pyrrole-3,4-dicarbonitrile (1.4 g; 0.0075 mol) is added to $CHCl_3$ (35 mL), much of the solid dissolving. A solution of bromine (0.4 mL; 0.008 mol) in $CHCl_3$ (5 mL) is added dropwise over 20 minutes. Initially the color is discharged rapidly, but as a new, gummy solid begins to precipitate, the color remains. After stirring 30 minutes at ambient, the mixture is brought to reflux, resulting in a much more discreet solid. After refluxing 90 minutes, the reaction mixture is cooled and an aliquot is removed and analyzed (HPLC), showing ca. 60% starting material still remaining. In a single portion fresh bromine (0.2 mL; 0.004 mol) is added, and refluxing continued another 45 minutes whereupon an aliquot shows 10% starting material remaining. Another fresh portion of bromine (0.2 mL; 0.004 mol) is added to the refluxing suspension and refluxing is continued another 30 minutes. The suspension is cooled and stirred 18 hours at room temperature. Solvent is removed under reduced pressure to yield a greenish solid which is extracted with hot $CHCl_3$, leaving behind a dark residue. The extract is treated with DARCO and filtered hot. The clear yellow filtrate quickly began to deposit a white precipitate. After cooling to −10° C., the white solid is collected by filtration.

Calcd for $C_{12}H_6BrN_3$: C, 52.94; H, 2.21; N, 15.44; Br, 29.41.
Found: C, 51.64; H, 2.35; N, 14.91; Br, 28.69. m.p.=225°-258° C.

EXAMPLE 52

Preparation of 2-(3,4-Dichlorophenyl)-5-nitropyrrole-3-carbonitrile

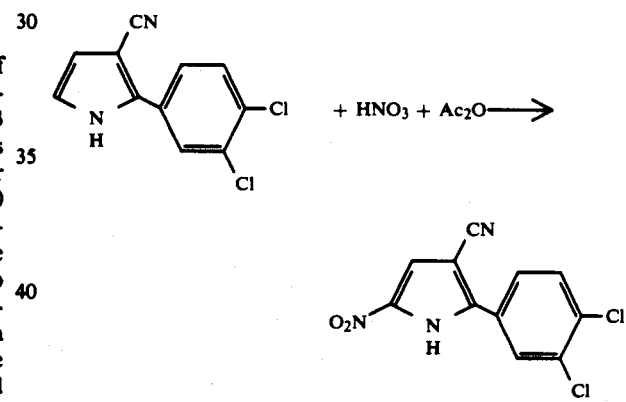

2-(3,4-Dichlorophenyl)pyrrole-3-carbonitrile (3.0 g, 0.013 mole) is added to acetic anhydride (50 mL) and 90% nitric acid (0.6 ml) with very little exotherm. The mixture is slowly warmed to 30° and is then held at 30°-33° until everything goes into solution. Gradually a new solid precipitates. The mixture is stirred for 2 to 3 hours at room temperature and then poured into water and ice to decompose the acetic anhydride. After stirring hour the mixture is filtered and the solid (2.9 g, 82%) collected and dried. A portion (1.5 g) is purified by column chromatography on silica gel using 75/25 hexane/ethyl acetate for elution to give 0.7 g of yellow solid with m.p. 228°-231°.

Calcd for $C_{11}H_5Cl_2N_3O_2$: C, 46.80; H, 1.77; N, 14.89; Cl, 25.17
Found: C, 46.50; N, 1.96; N, 14.27; Cl, 24.30.

By the same procedure, starting with 2-(p-chlorophenyl)pyrrole-3-carbonitrile, 2-(p-chlorophenyl)-5-nitropyrrole-3-carbonitrile is obtained, m.p. 201°-206° C. Also, 2-(p-trifluoromethylphenyl)pyrrole-3-carbonitrile gives 2-(p-trifluoromethylphenyl)-5-nitropyrrole-3-carbonitrile by the above procedure. This compound has a melting point of 164°-165.5° C.

EXAMPLE 53

Preparation of
4-Bromo-2-(3,4-dichlorophenyl)-5-nitropyrrole-3-carbonitrile

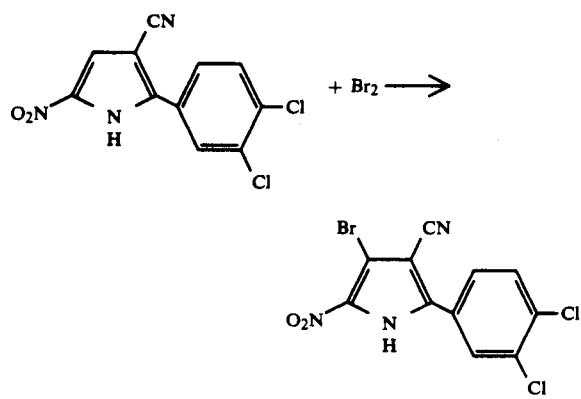

2-(3,4-Dichlorophenyl)-5-nitropyrrole-3-carbonitrile (0.5 g, 0.0017 mol) is dissolved in dry dioxane (10 mL). To this solution is added bromine (0.28 g, 0.0017 mole) in dioxane. After stirring overnight, the solution is poured into water precipitating a tan solid (0.54 g, 88%). Recrystallization from acetonitrile (5 mL) gives 0.26 g of tan solid with m.p. 195°-200° C.

Calcd for $C_{11}H_4BrCl_2N_3O_2$: C, 36.57; H, 1.10; N, 11.63; Br, 22.13; Cl, 19.67.

Found: C, 36.46; H, 1.29; N, 11.50; Br, 21.63; Cl, 19.28.

Following the above procedure of Example 53, but starting with 2-(p-chlorophenyl)-5-nitropyrrole-3-carbonitrile gives 4-bromo-2-(p-chlorophenyl)-5-nitropyrrole-3-carbonitrile, m.p. 180°-185° C.

EXAMPLE 54

5-(3,4-Dichlorophenyl)-4-nitropyrrole-2-carbonitrile

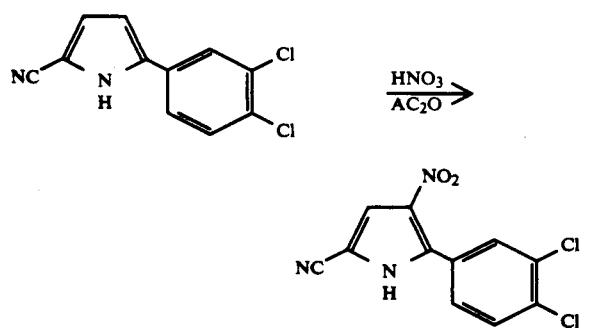

To a suspension of 5-(3,4-dichlorophenyl)pyrrole-2-carbonitrile (1.2 g, 5.1 mmol) in 25 mL of acetic anhydride at 30° under nitrogen, is added dropwise 90% nitric acid (0.3 mL, 5.1 mmol). The reaction exotherms to 45° C. and becomes a green solution. After being allowed to stir for 2 hours the reaction is poured into 50 mL of water and stirred vigorously for 5 minutes. The beige precipitate which results is filtered off and dissolved in a minimum amount of acetone. Chromatography over silica gel using 3:1 hexane-ethyl acetate affords the nitropyrrole (1.2 g, 84%) as an off-white solid, m.p. >200° C.

EXAMPLE 55

3-Bromo-5-(3,4-dichlorophenyl)-4-nitropyrrole-2-carbonitrile

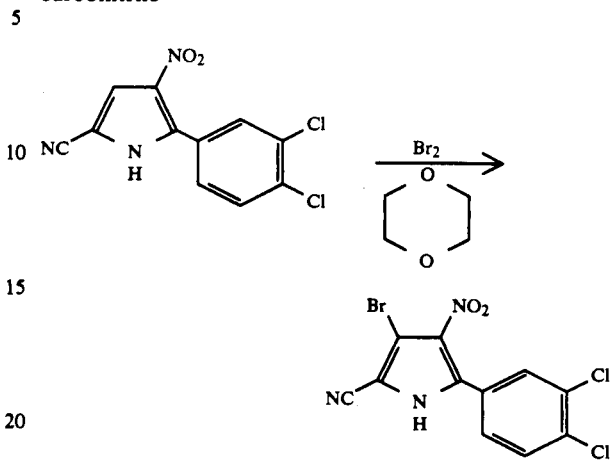

To a suspension of 5-(3,4-dichlorophenyl)-4-nitropyrrole-2-carbonitrile (0.6 g, 2.1 mmol) in 10 mL of dioxane at 25° C., under nitrogen, is added dropwise a solution of bromine (0.3 g, 2.1 mmol) in 5 mL of dioxane. The reaction is allowed to stir overnight. Addition of 50 mL of water causes precipitation of a yellow solid which is collected and vacuum oven dried (50 mm Hg, 45° C.) to afford the brominated pyrrole (0.7 g, 90%) as a light yellow solid, m.p. >200° C.

EXAMPLE 56

4-(p-chlorophenyl)-2-(trifluoromethyl-2-oxazolin-5-one

In a single portion, trifluoroacetic anhydride, (1.7 mL; 0.012 mol) is added to poWdered 2-(p-chlorophenyl)glycine (11.4 g; 0.06 mol), causing an immediate exotherm to about 40° C., a yellow color forming on the surface of the solid. As the mixture is slowly heated to 70° C., more of the solid dissolves to an orange/amber oil. All the solid dissolved in approximately 2 hours, and heating is continued another hour. Solvent is removed under reduced pressure on a rotary evaporator. Toluene is twice added and removed under reduced pressure, but the odor of trifluoroacetic acid is still evident. This yellow semi-solid (yield theoretical; purity>90% by HPLC) is the above-identified compound and is used in the next step without further purification.

EXAMPLE 57

Preparation of 2-(p-chlorophenyl)-5-(trifluoromethyl) pyrrole-3-carbonitrile 4-(p-chlorophenyl)-2-(trifluoromethyl)-2-oxazolin-5-one (2.5 g; 0.01 mol) is dissolved in nitromethane (50 mL). In a single portion, 2-chloroacrylonitrile (8.0 mL; 0.01 mol) is added to the solution, and the resulting solution is stirred 18 hours at reflux under a nitrogen atmosphere. Cooling the red/brown solution to −5° C. in an ice-acetone bath causes the formation of a precipitate which is collected by filtration and washed with a small portion of cold nitromethane. The resulting tan solid is recrystallized from hot ethylene dichloride yielding the product as white crystals (1.8 g; 56% theory), m.p. 238°-241° C. (dec.).

By utilizing the appropriate arylglycine in the procedure of Example 55 and following the procedure of this Example, the following 2-aryl-5-(trifluoromethyl)pyrrole-3-carbonitrile were prepared:

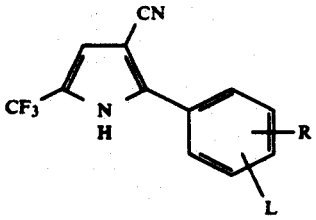

| R | L | m.p. °C. |
|---|---|---|
| H | H | 215–218 |
| H | 4-CH₃ | 191–193 |
| H | 4-OCH₃ | 168–180 (dec.) |
| 3-Cl | 4-Cl | 245–246 (dec.) |
| H | 4-CF₃ | 218–219 |

EXAMPLE 58

Preparation of 4-Bromo-2-(p-chlorophenyl)-5-(trifluoromethyl)pyrrole-3-carbonitrile Under a nitrogen purge, a suspension or 2-(p-chlorophenyl)-5-(trifluoromethyl)pyrrole-3-carbonitrile (1.6 g; 0.005 mol) in acetic acid (25 mL) is heated, all the material dissolving to a clear solution at about 60° C. A solution of bromine (0.8 mL; 0.015 mol) in acetic acid (10 mL) is added dropwise over 15 minutes to the refluxing solution. The solution is refluxed 6 hours then allowed to stir 18 hours at room temperature. The HPLC of the reaction mixture shows about 80% conversion to product. The mixture is heated back to reflux and more bromine (0.5 mL; 0.01 mol) in acetic acid (5 mL) is added dropwise. After refluxing another 3 hours, the aliquot shows >95% conversion to product. The reaction is cooled, and solvent removed under reduced pressure on a rotary evaporator to obtain a dark grey solid. Toluene is added to the mixture and removed under reduced pressure, but the odor of acetic acid still remains. The entire material is dissolved in hot toluene (75 mL) to a turbid solution which is treated with DARCO filter and filtered. The light pink solution deposits a white solid upon cooling to ambient. After cooling in the freezer, the solid is collected by filtration, washed with hexanes, and dried on the filter. Further drying in a vacuum oven at 45° C. provides the product (1.2 g; app. 60% theoretical); m.p. 247°–250° C.(dec.).

Anal. Calcd for C₁₂H₅BrClF₃N₂: C, 41.20; H, 1.43; N, 8.01; Br, 22.89; Cl, 10.16; F, 16.31.

Found: C, 41.27; H, 1.48; N, 8.10; Br, 22.92; Cl, 10.16; F, 16.03.

By brominating the appropriate 2-aryl-5-(trifluoromethyl)pyrrole-3-carbonitrile, obtained by the procedure of Example 57, according to the above recipe, the following additional examples are prepared:

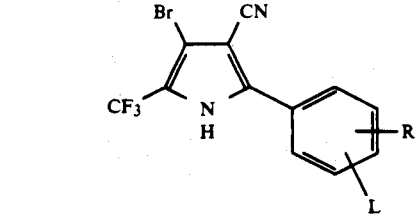

| R | L | m.p. °C. |
|---|---|---|
| H | H | 235–238 |
| H | 4-CH₃ | 244–245 |
| 3-Cl | 4-Cl | 218–223 |
| H | 4-CF₃ | 225–226 |

EXAMPLE 59

Preparation of 2-(4-chlorophenyl)-5-trifluoromethylpyrrole-3,4-dicarbonitrile

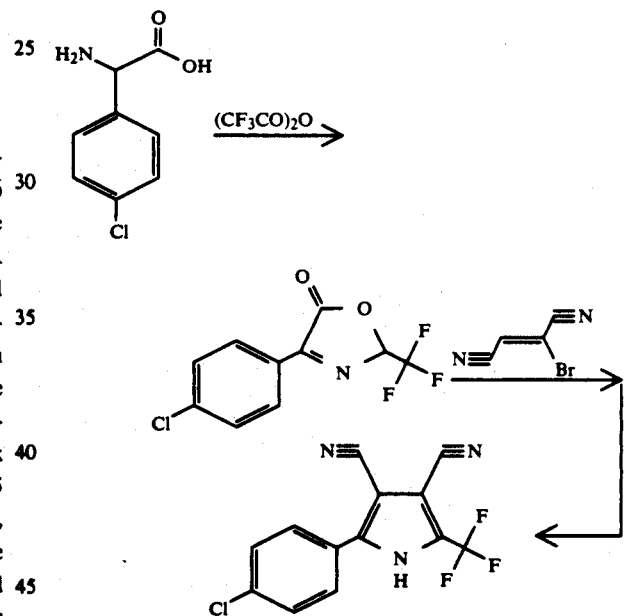

Trifluoroacetic anhydride (3.1 mL; 0.022 mol) is added in a single portion to (4-chlorophenyl)glycine (2.0 g; 0.011 mol), causing an immediate yellow color and some refluxing. The mixture is slowly heated to reflux, causing all the material to dissolve to a yellow/orange solution which is heated 2 hours further. The reaction mixture is cooled, and solvent removed under reduced pressure. Toluene, is twice added and removed under reduced pressure to yield a very thick oil (ν$_{CO}$=1800 cm⁻¹). This residue is dissolved (some insolubles) in CH₃NO₂ (40 mL) and bromofumaronitrile (2.7 g; 0.018 mol) is added in a single portion. The resulting solution is heated at reflux 18 hours, yielding a dark red solution. Solvent is removed under reduced pressure and the dark residue is dissolved in CH₂Cl₂, some insolubles being removed by filtration. The material is fractionated via dry column chromatography (silica gel; 3% 2-PrOH in CH₂Cl₂), and appropriate fractions are taken. Evaporation of one fraction yields the desired compound as a yellow solid which is recrystallized from CH₃CN (DARCO treatment) to yield a pale yellow solid (0.2 g). m.p.=238°-241° C. (some dec).

EXAMPLE 60

Insecticide and acaricide evaluations

All tests are preformed using technical materials. All concentrations reported herein are in terms of active ingredient. All tests are kept at 27° C.

*Spodoptera eridania.* 3rd instar larvae, southern armyworm

A Sieva lima bean leaf expanded to 7-8 cm in length is dipped in the test suspension with agitation for 3 seconds and placed in a hood to dry. The leaf is then placed in a 100×10 mm petri dish containing a damp filter paper on the bottom and ten 3rd instar caterpillars. The dish is maintained for 5 days before observations are made of mortality, reduced feeding, or any interference with normal moulting.

*Spodoptera eridania.* 7-day residual

The plants treated in the above Test are maintained under high intensity lamps in the greenhouse for 7 days. These lamps duplicate the effects of a bright sunny day in June in New Jersey and are kept on for 14 hour day length. After 7 days, the foliage is sampled and assayed as in the above-said Test.

*Aphis fabae.* mixed instar, bean aphid

Pots containing single nasturtium plants (Tropaeolum sp.) about 5 cm tall are infested with about 100-200 aphids one day before the test. Each pot is sprayed with the test formulation for 2 revolutions of a 4 rpm turntable in a hood, using a #154 DeVilbiss atomizer. The spray tip is held about 15 cm from the plant and the spray directed so as to give complete coverage of the plants and the aphids. The sprayed pots are set on their sides on white enamel trays and held for 2 days, following which mortality estimates are made.

*Tetrantchus urticae*(P-resistant strain),2-spotted spider mite

Sieva lima bean plants with primary leaves expaned to 7-8 cm are selected and cut back to one plant per pot. A small piece is cut from a leaf taken from the main colony and placed on each leaf of the test plants. This is done about 2 hours before treatment to allow the mites to move over to the test plant and to lay eggs. The size of the cut piece is varied to obtain about 100 mites per leaf. At the time of the treatment, the piece of leaf used to transfer the mites is removed and discarded. The mite-infested plants are dipped in the test formulation for 3 seconds with agitation and set in the hood to dry. Plants are kept for 2 days before estimates of adult kill are made using the first leaf. The second leaf is kept on the plant for another 5 days before observations are made of the kill of eggs and/or newly emerged nymphs.

*Diabrotic undecimounctata howardi.* 3rd instar southern corn rootworm

One cc of fine talc is placed in a 30 ml wide-mouth screw-top glass jar. One ml of the appropriate acetone suspension is pepetted onto the talc so as to provide 1.25 and 0.25 mg of active ingredient per jar. The jars are set under a gentle air flow until the acetone is evaporated. The dried talc is loosened, 1 cc of millet seed is added to serve as food for the insects and 25 ml of moist soil is added to each jar. The jar is capped and the contents thoroughly mixed on a Vortex Mixer. Following this, ten 3rd instar rootorms are added to each jar and the jars are loosely capped to allow air exchange for the larvae. The treatments are held for 6 days before mortality counts are made. Missing larvae are presumed dead, since they decompose rapidly and can not be found. The concentrations used in this test correspond approximately to 50 and 10 kg/ha, respectively.

| Rating Scale: | |
|---|---|
| 0 = no effect | 5 = 56–65% kill |
| 1 = 10–25% kill | 6 = 66–75% kill |
| 2 = 26–35% kill | 7 = 76–85% kill |
| 3 = 36–45% kill | 8 = 86–99% kill |
| 4 = 46–55% kill | 9 = 100% kill |
| | R - reduced feeding |

TABLE I

| Compound | BEAN APHIDS ppm 100 | ARMYWORMS ppm 1000 | ARMYWORMS ppm 100 | ARMYWORMS 7 days | P. RES MITES ppm 300 | SCRW kg/ha 50 |
|---|---|---|---|---|---|---|
| 4,5-dichloro-2-phenylpyrrole-3-carbonitrile | 0 | 9 | 8.5 | 9 | 0 | 0 |
| 4,5-dichloro-2-(p-chlorophenyl)-pyrrole-3-carbonitrile | 0 | 9 | 9 | 9 | 0 | 5.5 |
| 4,5-dichloro-2-(3,4-dichlorophenyl)pyrrole-3-carbonitrile | 0 | 9 | 9 | 9 | 0 | 0 |
| 4,5-dichloro-2-[-(trifluoromethoxy)phenyl-pyrrole-3-carbonitrile | 7.5 | 9 | 9 | 9 | 9 | 7.7 |
| 4,5-dichloro-2-(o-chlorophenyl)-pyrrole-3-carbonitrile | 0 | 9 | 9 | | 0 | 0 |
| 2-(p-bromophenyl)4,5-dichloropyrrole-3- | 0 | 9 | 9 | | 8 | 0 |

TABLE I-continued

| Compound | BEAN APHIDS ppm 100 | ARMYWORMS 1000 | ARMYWORMS ppm 100 | ARMYWORMS 7 days | P. RES MITES ppm 300 | SCRW kg/ha 50 |
|---|---|---|---|---|---|---|
| carbonitrile | | | | | | |
| 4,5-dichloro-2-(alpha,alpha,alpha-trifluoro-p-tolyl)pyrrole-3-carbonitrile | 0 | 9 | 9 | | 9 | 8 |
| 4,5-dibromo-2-(o-chlorophenyl)-pyrrole-3-carbonitrile | 0 | 9 | 4 | | 0 | 0 |
| 4,5-dibromo-2-(p-chlorophenyl)-pyrrole-3-carbonitrile | 0 | 9 | 9 | | 0 | 0 |
| 4,5-dibromo-2-(alpha,alpha,alpha-trifluoro-p-tolyl)pyrrole-3-carbonitrile | 0 | 9 | 9 | | 9 | 9 |
| 4,5-dichloro-2-(2,4-dichlorophenyl)pyrrole-3-carbonitrile | 0 | 9 | 9 | 9 | 0 | 0 |
| 4,5-dibromo-2-(2,4-dichlorophenyl)pyrrole-3-carbonitrile | 0 | 9 | 9 | 9 | 0 | 0 |
| 4,5-dichloro-2-(m-chlorophenyl)-pyrrole-3-carbonitrile | 0 | 9 | 9 | 9 | 0 | 0 |
| 2,3-dichloro-4-nitro-5-phenylpyrrole | 0 | 9 | 9 | 9 | 0 | 0 |
| 2,3-dichloro-5-(p-chlorophenyl)-4-nitropyrrole | 0 | 9 | 9 | 9 | 7.5 | 8 |
| 2,3-dibromo-5-(p-chlorophenyl)-4-nitropyrrole | 0 | 9 | 9 | 9 | 0 | 7.5 |
| 2,3-dibromo-4-nitro-5-phenylpyrrole | 0 | 9 | 9 | 9 | 0 | 0 |
| 2,3-dichloro-5-(3,4-dichlorophenyl)-4-nitropyrrole | 0 | 9 | 9 | 9 | 0 | 0 |
| 2-(p-bromophenyl)4,5-dichloro-3-nitropyrrole | 8 | 9 | 9 | 9 | 8.5 | 8 |
| 2,3-dichloro-4-nitro-5-(alpha,alpha,alpha-trifluoro-p-tolyl)pyrrole | 8.3 | 9 | 9 | 9 | 9 | 8.3 |

EXAMPLE 61

Insecticidal evaluations

*Heliothis virescens*, 3rd instar tobacco budworm

Cotton cotyledons are dipped in the test formulation and allowed to dry in a hood. When dry, each is cut into quarters and ten sections placed individually in 30 ml plastic medicine cups containing a 5-7 mm long piece of damp dental wick. One third-instar caterpillar is added to each cup and a cardboard lid placed on the cup. Treatments are maintained for 3 days at before mortality counts and estimates of reduction in feeding damage are made.

*Empoasca abrupta*, adults, western potato leafhopper

A Sieva lima bean leaf about 5 cm long is dipped in the test formulation for 3 seconds with agitation and placed in a hood to dry. The leaf is placed in a mm petri dish containing a moist filter paper on the bottom. About 10 adult leafhoppers are added to each dish and the treatments are kept for 3 days before mortality counts are made.

*Blattella germanica.* bait test, adult male German cockroach

A 0.1% bait is prepared by pipetting 1 ml of a 1000 ppm solution of the test compound in acetone onto 1 gram of cornmeal in a 30 ml wide-mouth bottle. The bait is dried by passing a gentle stream of air into the bottle. The bait is placed in a 1 pint wide-mouth Mason jar and ten adult male cockroaches are added. A screen lid is placed on the jar and a small piece of cotton soaked in 10% honey is put on the top of the screen lid. Mortality counts are made after 3 days.

*Blattela germanica*, residue test, adult male German cockroach

One ml of a 1000 ppm acetone solution of the test material is pipetted slowly over the bottom of a 150×15 mm petri dish so as to give as uniform coverage as possible. After the deposit has dried, 10 adult male cockroaches are placed in each dish and the lid is added. Mortality counts are made after 3 days.

*Spodoptera eridania*, systemic uptake, 3rd instar larvae, southern armyworm

The compound is formulated as an emulsion containing 0.1 gm of the test material, 0.2 gm of Emulphor EL-620 ® emulsifier, 10 ml of acetone and 90 ml of water. This is diluted 10-fold with water to give a 100 ppm emulsion for the test. Subsequent 10-fold dilutions are made with water as needed. Sieva lima bean plants, with the primary leaves expanded to a length of 7–8 cm, are cut off at least 3 cm above the soil level to avoid contamination with soil bacteria that will cause decay of the stem during the test. The cut stems are placed in the test emulsions and each stem is wrapped with a bit of cotton to hold the stem off the bottom of the bottle and to limit evaporation and volatilization of the compound. The test is maintained for 3 days at 27° C. to allow the compounds to be taken up into the plant. Following this, one leaf is removed from the plant and placed in a 100×10 mm petri dish with 10 southern armyworms as described in Test III. Mortality counts and observations of feeding damage are made 3 and 5 days later.

*Empoasca abrupta*, Adults, Western Potato Leafhoppers, Systemic Uptake

The compound is formulated as an emulsion containing 0.1 gm of the test material, 0.2 gm of Emulphor EL-620 ® emulsifier, 10 ml of acetone and 90 ml of water. This is diluted 10-fold with water to give a 100 ppm emulsion for the test. Subsequent 10-fold dilutions are made with water as needed. Sieva lima bean plants, with the primary leaves expanded to a length of 7–8 cm, are cut off at least 3 cm above the soil level to avoid contamination with soil bacteria that will cause decay of the stem during the test. The cut stems are placed in the test emulsions and each stem is wrapped with a bit of cotton to hold the stem off the bottom of the bottle and to limit evaporation and volatilization of the compound. The test is maintained for 3 days at 27° C. to allow the compounds to be taken up into the plant. Following this, one leaf is removed from the plant and placed in a 100×10 mm petri dish and tested as in Test VIII, above.

The rating scale for the above tests is the same as described in Example 9.

TABLE II

| | LEAF HOPPER ppm 100 | TBW[3] ppm 1000 | | SAW ppm 100 | C-S SYSTEMIC LEAF HOPPER ppm 100 | G. COCKROACH BAIT ppm 1000 | RES. ppm 1000 |
|---|---|---|---|---|---|---|---|
| | | | 100 | | | | |
| 4,5,-dichloro-2-phenylpyrrole-3-carbonitrile | 0 | 8 | | 0 | — | 0 | 0 |
| 4,5-dichloro-2-(p-chlorophenyl)-pyrrole-3-carbonitrile | 0 | 9 | 8.5 | 9 | 0 | 0 | 7 |
| 4,5-dichloro-2-(3,4-dichlorophenyl)pyrrole-3-carbonitrile | 0 | 9 | 9 | 9 | 0 | 7 | 7 |
| 4,5-dichloro-2-[p-(trifluoromethoxy)phenyl-pyrrole-3-carbonitrile | 9 | 9 | 9 | 9 | 9 | 0 | 8 |
| 4,5-dichloro-2-(o-chlorophenyl)-pyrrole-3-carbonitrile | 0 | | 0 | 7 | 0 | 0 | 0 |
| 2-(p-bromophenyl)-4,5-dichloropyrrole-3-carbonitrile | 0 | 9 | 9 | — | — | 0 | 0 |
| 4,5-dichloro-2-(alpha,alpha,alpha-trifluoro-p-tolyl)pyrrole-3-carbonitrile | 9 | 9 | 9 | — | 9 | 0 | 9 |
| 4,5-dibromo-2-(o-chlorophenyl)-pyrrole-3-carbonitrile | 0 | | 0 | 7 | 0 | 0 | 0 |
| 4,5-dibromo-2-(p-chlorophenyl)-pyrrole-3-carbonitrile | 0 | 9 | 9 | — | 0 | 0 | 0 |
| 4,5-dibromo-2-(alpha,alpha, | 9 | 9 | 9 | — | 9 | 0 | 9 |

TABLE II-continued

| | LEAF HOPPER ppm 100 | TBW[3] ppm 1000 | | C-S SYSTEMIC SAW ppm 100 | LEAF HOPPER ppm 100 | G. COCKROACH BAIT ppm 1000 | RES. ppm 1000 |
|---|---|---|---|---|---|---|---|
| | | | 100 | | | | |
| alpha-trifluoro-p-tolyl)pyrrole-3-carbonitrile | | | | | | | |
| 4,5-dichloro-2-(2,4-dichlorophenyl)pyrrole-3-carbonitrile | 0 | 9 | 9 | — | 0 | 0 | 0 |
| 4,5-dibromo-2-(2,4-dichlorophenyl)pyrrole-3-carbonitrile | 0 | | 0 | — | 0 | 0 | 0 |
| 4,5-dichloro-2-(m-chlorophenyl)-pyrrole-3-carbonitrile | 0 | 9 | 9 | — | 0 | 0 | 0 |
| 2,3-dichloro-4-nitro-5-phenylpyrrole | 0 | 9 | 6 | 8 | 9 | 0 | 4 |
| 2,3-dichloro-5-(p-chlorophenyl)-4-nitropyrrole | 8.5 | 9 | 8 | 9 | 0 | 9 | 9 |
| 2,3-dibromo-5-(p-chlorophenyl)-4-nitropyrrole | 0 | 8.5 | 6 | 0 | 0 | 0 | 9 |
| 2,3-dibromo-4-nitro-5-phenylpyrrole | 0 | 8.5 | 0 | 9 | 0 | 0 | 0 |
| 2,3-dichloro-5-(3,4-dichlorophenyl)-4-nitropyrrole | 9 | 9 | 9 | 9 | 9 | 0 | 9 |
| 2-(p-bromophenyl)-4,5-dichloro-3-nitropyrrole | 8 | 9 | 6.5 | 9 | 9 | 0 | 9 |
| 2,3-dichloro-4-nitro-5-alpha, alpha,alpha-trifluoro-p-tolyl)pyrrole | 9 | 9 | 8 | 9 | 9 | 0 | 9 |

EXAMPLE 62

(A) Evaluation of test compounds as nematicidal agents

Culture Maintenance: Cultures of *C. elegans* (Bristol strain from J. Lewis) are maintained on *E. coli* lawns on NG Agar Plates at 20° C. New cultures are established weekly.

Nematodes for testing are washed from 4-5 day old cultures using Fresh Ascaris Ringers Solution (FARS). The worms are further washed with FARS, containing gentamycin, to reduce bacterial contamination and centrifuged to separate worms from wash solution. This procedure is repeated three times. The washed worms are then added to *C. briggsae* Maintenance Medium (CbMM), from GIBCOa to which is added gentamycin (600 units/ml) and mycostatin (0.5 mg/ml).

The tests are then made with mixtures of three compounds, piggy-backed from another high capacity screening program to reduce additional labor and compound expenditures.

Compounds are dissolved in acetone and made up to volume with equal parts of water. The final test concentration of each compound in the mixture is 150 ppm. The test material is micropipetted (25 ul) into a single well of a 96-well sterile tissue culture plate (COSTAR)[b] and the solvent allowed to evaporate. These "treated" plates are used immediately or stored in a freezer without apparent adverse effects on the compounds.

A freshly prepared volume (50 ug) of *C. elegans* in CbMM is micropipetted into each treated well and several control wells per plate. Culture plate are incubated at 20° C.

Observations for efficacy are made under a dissecting microscope at 4, 24 and 48 hours post-immersion. Immediately prior to reading the plate, it is gently tapped to stimulate the movement of the worms. Activity is judged subjectively, but semi-quantitatively, based on the drug effects on motility of the adults and larvae. The criteria are as follows: 8=no motility, 7=markedly reduced motility in approximately 95% of worms, 6=reduced motility, 5=slightly reduced motility, 0=normal motility, same as controls. Other factors indicating activity are easily noted such as death, rigor mortis, contraction, coiling, paralysis, abnormal twitching, reduced worm population in 48 hours and other deviation from normal behavior.

| Day 0 | Inoculate E. Coli-NG Agar Dish With 30-50 C. Elegans |
| | Incubate At 20° C. |
| Day 4 | Harvest New C. Elegans Population |
| | Wash With Antibiotics |
| | Transfer To CbMM |
| | Add C. Elegans (25-100 UL) To "Medicated" |

-continued

| | Wells[a] |
|---|---|
| | Observe For Activity At 4 Hours Post-Immersion |
| Day 5 | Observe For Activity |
| Day 6 | Observe For Activity |

[1]Medicated Wells May Be Prepared Fresh Or Earlier And Stores In Freezer

Data obtained in these test are reported in Table III below.

(B) Root-Knot Nematode Assay

Populations of the root-knot nematode (*Meloidogyne incognita*) are maintained on Fireball tomatoes in the greenhouse. Egg masses are removed from the infested root surfaces and are kept on moistened filter paper for 24 hours to allow them to hatch. Larvae emerge and drop into the water beneath the paper. Larvae for test are transferred to cell plate wells containing test compounds at 300 ppm in 3% acetone, about 10 larvae per cell well. Infested wells are held at 27° C. and mortality is determined 24 hours after treatment.

Data obtained are reported in Table III below.

TABLE III

| | C. Ele. 150 ppm | | Root Knot Nematodes. |
|---|---|---|---|
| | L | A | 300 ppm |
| 4,5-dichloro-2-[p-(trifluoromethoxy)phenyl-pyrrole-3-carbonitrile | — | — | 4 |
| 4,5-dichloro-2-(alpha,alpha,alpha-trifluoro-p-tolyl)pyrrole-3-carbonitrile | 9 | 9 | 5 |
| 4,5-dibromo-2-(alpha,alpha,alpha-trifluoro-p-tolyl)pyrrole-3-carbonitrile | 9 | 9 | 0 |
| 2,3-dichloro-4-nitro-5-phenylpyrrole | 0 | 0 | 9 |
| 2,3-dichloro-5-(p-chlorophenyl)-4-nitropyrrole | 9 | 9 | 9 |
| 2,3-dichloro-5-(3,4-dichlorophenyl)-4-nitropyrrole | 9 | 9 | 0 |
| 2-(p-bromophenyl)-4,5-dichloro-3-nitropyrrole | 9 | 9 | 6 |
| 2,3-dichloro-4-nitro-5-(alpha,alpha,alpha-trifluoro-p-tolyl)pyrrole | 9 | 9 | — |

EXAMPLE 63

Following the procedures of Examples 59 and 60, compounds of the invention are evaluated against a variety of insect species including: leaf hoppers, tobacco budworm, southern armyworm, and the German cockroach. The rating system is the same system used in the above-said examples. Data obtained are reported in Table IV below. Where two or more tests have been conducted with the same test compound, the results are overaged. Also, a—in the table indicates no test.

TABLE IV

| | LEAF HOPPER | TBW[3] | | ARMYWORMS | | | C-S SYSTEMIC SAW | C-S SYSTEMIC LEAF HOPPER | G. COCKROACH RES. |
|---|---|---|---|---|---|---|---|---|---|
| Compound | ppm 100 | ppm 1000 | ppm 100 | ppm 1000 | ppm 100 | 7 days | ppm 100 | ppm 100 | ppm 1000 |
| 2,5-dichloro-4-phenylpyrrole-3-carbonitrile | 0 | 6 | 0 | 9 | 9 | 8 | 0 | 0 | 0 |
| 2,3-dibromo-4-nitro-5-phenyl-pyrrole | 0 | 9 | 0 | 9 | 9 | — | 9 | 0 | 0 |
| 4-chloro-2-(p-chlorophenyl)-pyrrole-3-carbonitrile | 0 | 9 | 2 | 9 | 9 | — | 9 | 9 | 0 |
| 4,5-dichloro-2-(o-chlorophenyl)pyrrole-3-carbonitrile | 0 | 0 | 0 | 9 | 9 | — | 7 | 0 | 0 |
| 5-bromo-2-(p-chlorophenyl)pyrrole-3-carbonitrile | 0 | 9 | 0 | 9 | 9 | — | — | 0 | 0 |
| 4,5-dichloro-2-(3,4-dichlorophenyl)-1-(ethoxymethyl)pyrrole-3-carbonitrile | 9 | 9 | 9 | 9 | 9 | 9 | 5 | 0 | 7 |
| 4,5-dichloro-2-(p-chlorophenyl)-1-methylpyrrole-3-carbonitrile | 0 | 9 | 9 | 9 | 9 | 9 | — | 0 | 9 |
| p-(4,5-dichloro-3-cyanopyrrole-2-yl)methylbenzoate | 0 | 4R8 | 0 | 9 | 0 | — | 3 | 0 | 0 |
| 4,5-dibromo-2-(3,4-dichlorophenyl)pyrrole-3-carbonitrile | 0 | 9 | 0 | 9 | 9 | 9 | 0 | 0 | 0 |
| 4,5-dichloro-2-(alpha,alpha,alpha-trifluoro-m-tolyl)pyrrole-3-carbonitrile | 0 | 9 | 9 | 9 | 9 | 9 | 9 | 0 | 9 |

TABLE IV-continued

| | LEAF HOPPER | TBW[3] | | ARMYWORMS | | | C-S SYSTEMIC | | G. COCKROACH RES. |
| | | | | | | | SAW | LEAF HOPPER | |
| Compound | ppm 100 | ppm 1000 | 100 | ppm 1000 | 100 | 7 days | ppm 100 | ppm 100 | ppm 1000 |
|---|---|---|---|---|---|---|---|---|---|
| 4,5-dichloro-2-(3,4-dichlorophenyl)-1-ethylpyrrole-3-carbonitrile | 0 | 9 | 9 | 9 | 9 | 9 | 9 | 9 | 0 |
| 4,5-dichloro-2-(3,4-difluorophenyl)pyrrole-3-carbonitrile | 0 | 9 | 9 | 9 | 9 | 9 | 9 | 9 | 0 |
| 4,5-dichloro-2-(3,4-dichlorophenyl)-1-methylpyrrole-3-carbonitrile | 0 | 9 | 9 | 9 | 9 | 9 | 9 | 9 | 9 |
| 4,5-dichloro-2-[p-(methylsulfonyl)phenyl]pyrrole-3-carbonitrile | 0 | — | 0 | 7 | 0 | 0 | 9 | 9 | 0 |
| 4,5-dibromo-1-methyl-2-(alpha,alpha,alpha-trifluoro-p-tolyl)pyrrole-3-carbonitrile | 0 | 9 | 8 | 9 | 9 | 9 | 9 | 9 | 8.5 |
| 4,5-dichloro-2-(p-fluorophenyl)pyrrole-3-carbonitrile | 0 | 9 | 9 | 9 | 9 | 9 | 9 | 9 | 0 |
| 4,5-dibromo-2-(3,4-difluorophenyl)pyrrole-3-carbonitrile | 0 | 9 | 9 | 9 | 9 | 9 | 4.5 | 4.5 | 0 |
| 4,5-dibromo-2-(p-fluorophenyl)pyrrole-3-carbonitrile | 0 | 9 | 9 | 9 | 9 | 9 | 0 | 0 | 0 |
| 4,5-dibromo-2-(p-nitrophenyl)pyrrole-3-carbonitrile | 0 | 9 | 6 | 9 | 9 | 4 | 4.5 | 9 | 9 |
| 4,5-dichloro-2-(-p-nitrophenyl)pyrrole-3-carbonitrile | 0 | 9 | 7 | 9 | 9 | 9 | 4.5 | 4.5 | 9 |
| 1-benzyl-4,5-dibromo-2-(alpha,alpha,alpha-trifluoro-p-tolyl)pyrrole-3-carbonitrile | 9 | 9 | 9 | 9 | 9 | 9 | 9 | 6 | 0 |
| 4,5-dichloro-2-(p-cyanophenyl)pyrrole-3-carbonitrile | 0 | 9 | 8 | 9 | 9 | — | 0 | 0 | 5 |
| 4,5-dibromo-2-[p-(methylsulfonyl)phenyl]pyrrole-3-carbonitrile | 0 | 2 | — | 9 | 0 | — | 0 | 0 | 0 |
| 4,5-dibromo-2-(p-chlorophenyl)pyrrole-3-carbonitrile | 0 | 9 | 7 | 9 | 9 | — | 0 | 0 | 0 |
| 4,5-dichloro-2-(3,4-dichlorophenyl)-1-[2-(methylthio)ethyl]pyrrole-3-carbonitrile | 0 | 8 | 5 | 9 | 0 | — | 9 | 0 | 0 |
| 1-methyl-4,5-dichloro-2-(3,4-dichlorophenyl)pyrrole-3-carbonitrile | 7 | 7 | 0 | 9 | 0 | — | 9 | 0 | 0 |
| 4,5-dichloro-1-methyl-2-(alpha,alpha,alpha-trifluoro-p-tolyl)pyrrole-3-carbonitrile | 9 | 9 | 9 | 9 | 9 | 0 | 9 | 9 | 9 |
| 5-bromo-4-chloro-2-(p-chlorophenyl)pyrrole-3-carbonitrile | 2.5 | — | 9 | 9 | 9 | 9 | 0 | 6 | 9 |
| 2,3-dichloro-5-(3,4-dichlorophenyl)-1-(ethoxymethyl)-4-nitropyrrole | 6 | 5 | 0 | 9 | 9 | — | 9 | 9 | 9 |
| 4-bromo-5-chloro- | 0 | 9 | 9 | 9 | 9 | 9 | 7 | 0 | 9 |

TABLE IV-continued

| | LEAF HOPPER | TBW[3] | | ARMYWORMS | | | C-S SYSTEMIC | | G. COCKROACH RES. |
|---|---|---|---|---|---|---|---|---|---|
| | | | | | | | SAW | LEAF HOPPER | |
| | ppm | ppm | | ppm | | 7 | ppm | ppm | ppm |
| Compound | 100 | 1000 | 100 | 1000 | 100 | days | 100 | 100 | 1000 |
| 2-(p-chlorophenyl)pyrrole-3-carbonitrile | | | | | | | | | |
| 1-benzyl-4,5-dichloro-2-(3,4-dichlorophenyl)pyrrole-3-carbonitrile | 0 | 9 | 0 | 9 | 9 | 5.5 | 9 | 9 | 2 |
| Ethyl 2,3-dichloro-5-(3,4-dichlorophenyl)-4-cyanopyrrole-1-acetate | 0 | 9 | 4 | 9 | 9 | 7 | 9 | 0 | 0 |
| 4,5-dichloro-1-(ethoxymethyl)-2-(alpha,alpha,alpha-trifluoro-p-tolyl)pyrrole-3-carbonitrile | 9 | 9 | 9 | 9 | 9 | 9 | 9 | 9 | 9 |
| 3-bromo-5-(3,4-dichlorophenyl)pyrrole-2,4-dicarbonitrile | 0 | 9 | 8.5 | 9 | 9 | 9 | 5 | 0 | 9 |
| 4,5-dichloro-2-(3,4-dichlorophenyl)-1-(2-propynyl)pyrrole-3-carbonitrile | 8 | 9 | 9 | 9 | 9 | 9 | 9 | 9 | 9 |
| 4,5-dibromo-3-(p-chlorophenyl)pyrrole-2-carbonitrile | 0 | 9 | 3 | 9 | 9 | 9 | 0 | 0 | 0 |
| 5-(3,4-dichlorophenyl)pyrrole-2,4-dicarbonitrile | 7 | 9 | 9 | 9 | 9 | 9 | 5 | 9 | 7 |
| 5-bromo-4-chloro-(3,4-dichlorophenyl)pyrrole-3-carbonitrile | 0 | 9 | 9 | 9 | 9 | 9 | 0 | 6 | 9 |
| 4,5-dibromo-3-(p-chlorophenyl)-1-methylpyrrole-2-carbonitrile | 0 | — | — | 9 | 9 | 0 | 0 | 0 | 9 |
| 2-bromo-5-phenylpyrrole-3,4-dicarbonitrile | 0 | 2 | 0 | 9 | 0 | 9 | 0 | 0 | 0 |
| 4-bromo-2-phenyl-5-(trifluoromethyl)pyrrole-3-carbonitrile | 0 | 9 | 9 | 9 | 9 | 9 | 9 | 9 | 0 |
| 2-(3,4-dichlorophenyl)-5-nitropyrrole-3-carbonitrile | 7 | 9 | 0 | 9 | 9 | 9 | 0 | 0 | 0 |
| 4-bromo-2-(3,4-dichlorophenyl)-5-nitropyrrole-3-carbonitrile | 0 | 5 | 0 | 9 | 0 | 3 | 0 | 0 | 0 |
| 2,4-dibromo-5-phenylpyrrole-3-carbonitrile | 0 | 9 | 9 | 9 | 9 | 9 | 0 | 0 | 0 |
| 2-(3,4-dichlorophenyl)-4,5-diiodopyrrole-3-carbonitrile | 0 | 9 | 9 | 9 | 9 | 9 | 5 | 7 | 9 |
| 2,3-dibromo-5-(p-chlorophenyl)-1-(ethoxymethyl)-4-nitropyrrole | 9 | 9 | 9 | 9 | 9 | 9 | 9 | 5 | 9 |
| 1-benzyl-2,3-dibromo-5-(p-chlorophenyl)-4-nitropyrrole | 0 | 4 | 0 | 9 | 8 | 0 | 9 | 9 | 3 |
| 2,3-dibromo-5-(p-chlorophenyl)-1-methyl-4-nitropyrrole | 0 | 8 | 7 | 9 | 9 | 7 | 0 | 4 | 0 |
| 4,5-dibromo-2-[p-(trifluoromethoxy)phenyl] | 9 | 9 | 9 | 9 | 9 | 9 | 9 | 0 | 0 |

TABLE IV-continued

| Compound | LEAF HOPPER ppm 100 | TBW[3] ppm 1000 | | ARMYWORMS ppm 1000 | 100 | 7 days | C-S SYSTEMIC SAW ppm 100 | LEAF HOPPER ppm 100 | G. COCKROACH RES. ppm 1000 |
|---|---|---|---|---|---|---|---|---|---|
| pyrrole-3-carbonitrile | | | | | | | | | |
| 4,5-dichloro-1-(ethoxymethyl)-2-[p-(trifluoromethoxy)phenyl]pyrrole-3-carbonitrile | 9 | 9 | 9 | 9 | 9 | 9 | 9 | 9 | 9 |
| 5-(p-chlorophenyl)-pyrrole-2,4-dicarbonitrile | 3 | 9 | 9 | 9 | 9 | 9 | 0 | 0 | 8 |
| 1-benzyl-4,5-dichloro-2[p-(trifluoromethoxy)phenyl]pyrrole-3-carbonitrile | 9 | 9 | 0 | 9 | 9 | 9 | 9 | 9 | 0 |
| 4,5-dichloro-2-(p-chlorophenyl)-1-(ethoxymethyl)pyrrole-3-carbonitrile | 8.5 | 9 | 9 | 9 | 9 | 9 | 9 | 9 | 0 |
| 4,5-dichloro-2-(3,4-dichlorophenyl)-1-(2-hydroxyethyl)pyrrole-3-carbonitrile | 0 | 9 | ? | 9 | 9 | 9 | 0 | 9 | 0 |
| 2-(p-chlorophenyl)-5-nitropyrrole-3-carbonitrile | 7 | 9 | 0 | 9 | 0 | 7 | 0 | 9 | 0 |
| 4-bromo-2-(p-chlorophenyl)-5-(trifluoromethyl)-pyrrole-3-carbonitrile | 9 | 9 | 9 | 9 | 9 | 9 | 9 | 9 | 9 |
| 4-bromo-2-(p-chlorophenyl)-5-nitropyrrole-3-carbonitrile | 0 | 9 | 0 | 9 | 9 | 9 | 0 | 7 | 0 |
| 3-bromo-5-(p-chlorophenyl)pyrrol-2,4-dicarbonitrile | 6 | 8 | 5 | 9 | 9 | 9 | 0 | 3 | 9 |
| 4,5-dichloro-2-(3,4-dichlorophenyl)pyrrole-1,3-dicarbonitrile | 0 | 9 | 0 | 9 | 9 | 9 | 0 | 0 | 9 |
| 1-[(benzyloxy)methyl]-4,5-dichloro-2-(3,4-dichlorophenyl)pyrrole-3-carbonitrile | 5 | 9 | 0 | 9 | 9 | 9 | 9 | 9 | 0 |
| 4,5-dichloro-2-(2,4-dichloro-5-fluorophenyl)pyrrole-3-carbonitrile | 4 | 5 | 0 | 9 | 9 | 9 | 9 | 0 | 9 |
| 5-[p-(trifluoromethoxy)phenyl]pyrrole-2,4-dicarbonitrile | 7 | 7 | 0 | 9 | 9 | 9 | 8 | 0 | 8 |
| 4,5-dichloro-1-[(p-chlorophenoxy)methyl-2-(3,4-dichlorophenyl)pyrrole-3-carbonitrile | 0 | 8 | 0 | 9 | 9 | 9 | 9 | 9 | 0 |
| 4,5-dichloro-2-(3,4-dichlorophenyl)-1-(3-iodo-2-propynyl)pyrrole-3-carbonitrile | 9 | 9 | 0 | 9 | 9 | 9 | 9 | 0 | 0 |
| 5-(3,4-dichlorophenyl)-4-nitropyrrole-2-carbonitrile | 9 | 9 | 9 | 9 | 9 | 9 | 0 | 0 | 9 |
| 2,4-dibromo-5-(p- | 0 | 9 | 9 | 9 | 9 | 9 | 9 | 0 | 0 |

TABLE IV-continued

| Compound | LEAF HOPPER ppm 100 | TBW[3] ppm 1000 | TBW[3] ppm 100 | ARMYWORMS ppm 1000 | ARMYWORMS ppm 100 | ARMYWORMS 7 days | C-S SYSTEMIC SAW ppm 100 | C-S SYSTEMIC LEAF HOPPER ppm 100 | G. COCKROACH RES. ppm 1000 |
|---|---|---|---|---|---|---|---|---|---|
| chlorophenyl)pyrrole-3-carbonitrile | | | | | | | | | |
| 3-bromo-5-[p-(trifluoromethoxy)phenyl]pyrrole-2,4-dicarbonitrile | 9 | 9 | 0 | 9 | 9 | 9 | 9 | 0 | 9 |
| 3-bromo-5-(3,4-dichlorophenyl)-4-nitropyrrole-2-carbonitrile | 9 | 6 | 0 | 9 | 9 | 9 | 0 | 0 | 0 |
| 4-bromo-2-(p-chlorophenyl)-1-methyl-5-(trifluoromethyl)pyrrole-3-carbonitrile | 9 | 9 | 0 | 9 | 9 | 9 | 0 | 0 | 9 |
| 3,4-dibromo-5-(3,4-dichlorophenyl)pyrrole-2-carbonitrile | 0 | 9 | 9 | 9 | 9 | 9 | 0 | 0 | 9 |
| 2-(3,4-dichlorophenyl)-5-(trifluoromethyl)pyrrole-3-carbonitrile | 0 | 9 | 9 | 9 | 9 | 9 | 0 | 0 | 9 |
| 5-(trifluoromethyl)-2-(alpha,alpha,alpha-trifluoro-p-tolyl)pyrrole-3-carbonitrile | 7 | 9 | 9 | 9 | 9 | 9 | 0 | 0 | 9 |
| 2,5-dibromo-4-(p-chlorophenyl)pyrrole-3-carbonitrile | 0 | 9 | 0 | 9 | 9 | 9 | 0 | 0 | 9 |
| 3,5-dibromo-4-(p-chlorophenyl)pyrrole-2-carbonitrile | 0 | 9 | 3 | 9 | 9 | 9 | 0 | 0 | 0 |
| 2-p-tolyl-5-(trifluoromethyl)pyrrole-3-carbonitrile | 0 | 9 | 0 | 7.5 | 0 | 0 | 0 | 0 | 0 |
| 4-bromo-2-p-tolyl-5-(trifluoromethyl)pyrrole-3-carbonitrile | 0 | 9 | 6 | 9 | 9 | 9 | — | — | 0 |
| 4-bromo-2-(p-chlorophenyl)-1-(ethoxymethyl)-5-(trifluoromethyl)pyrrole-3-carbonitrile | 9 | 9 | 9 | 9 | 9 | 9 | 0 | 0 | 9 |
| 4-bromo-2-(3,4-dichlorophenyl)-5-(trifluoromethyl)pyrrole-3-carbonitrile | 9 | 9 | 9 | 9 | 9 | 9 | 0 | 0 | 9 |
| 5-(alpha,alpha,alpha-trifluoro-p-tolyl)pyrrole-2,4-dicarbonitrile | 9 | 9 | 9 | 9 | 9 | 9 | 7 | 9 | 0 |
| 1-methyl-3-(alpha,alpha,alpha-trifluoro-p-tolyl)pyrrole-2,4-dicarbonitrile | 0 | 3 | 0 | 9 | 0 | 0 | 0 | 0 | 0 |
| 4-bromo-5-(trifluoromethyl)-2-(alpha,alpha,alpha-trifluoro-p-tolyl)pyrrole-3-carbonitrile | 9 | 9 | 9 | 9 | 9 | 9 | 0 | 0 | 9 |
| 3-bromo-1-methyl-5-(alpha,alpha,alpha-trifluoro-p-tolyl)pyrrole-2,4-dicarbonitrile | 0 | 7 | 0 | 9 | 0 | 0 | — | — | 0 |
| 4,5-dichloro-2-(alpha,alpha,alpha-trifluoro-p-tolyl)pyrrole-1,3-dicarbonitrile | 9 | 9 | 9 | 9 | 9 | — | — | — | 9 |

TABLE IV-continued

| | LEAF HOPPER | TBW[3] | ARMYWORMS | | | C-S SYSTEMIC SAW | LEAF HOPPER | G. COCKROACH RES. |
|---|---|---|---|---|---|---|---|---|
| | ppm | ppm | ppm | | 7 | ppm | ppm | ppm |
| Compound | 100 | 1000 | 100 | 1000 | 100 | days | 100 | 100 | 1000 |
| 3-bromo-5-(alpha, alpha,alpha-tri- fluoro-p-tolyl) pyrrole-2,4- dicarbonitrile | — | — | — | 9 | — | — | — | — | — |

What is claimed is:

1. A method for controlling insects, nematodes or acarina comprising: contacting said insects, nematodes or acarina, their infested breeding grounds, food supply or habitat with an insecticidally, nematicidally or acaricidally effective amount of a compound having the structure:

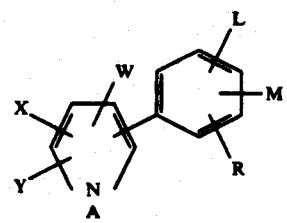

(I)

wherein X is H, F, Cl, Br, I, or $CF_3$; Y is F, Cl, Br, I, $CF_3$ or CN; W is CN or $NO_2$ and A is H; $C_1$–$C_4$ alkyl optionally substituted with from one to three halogen atoms, one hydroxy, one $C_1$–$C_4$ alkoxy, one $C_1$–$C_4$ alkylthio, one phenyl optionally substituted with $C_1$–$C_3$ alkyl, $C_1$–$C_3$ alkoxy or with one to three halogen atoms, one phenoxy optionally substituted with one to three halogen atoms or one benzyloxy optionally substituted with one halogen substituent; $C_1$–$C_4$ carbalkoxymethyl; $C_3$–$C_4$ alkenyl optionally substituted with from one to three halogen atoms; cyano; $C_3$–$C_4$ alkynyl optionally substituted with one halogen atom; di-($C_1$–$C_4$ alkyl) aminocarbonyl; or $C_4$–$C_6$ cycloalkylaminocarbonyl; L is H, F, Cl or Br; and M and R are each independently H, $C_1$–$C_3$ alkyl, $C_1$–$C_3$ alkoxy, $C_1$–$C_3$ alkylthio, $C_1$–$C_3$ alkylsulfinyl, $C_1$–$C_3$ alkylsulfonyl, cyano, F, Cl, Br, I, nitro, $CF_3$, $R_1CF_2Z$, $R_2CO$ or $NR_3R_4$, and when M and R are on adjacent positions and taken with the carbon atoms to which they are attached they may form a ring in which MR represents the structure:

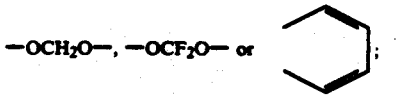

Z is S(O)n or O; $R_1$ is H, F, $CHF_2$, $CHFCl$, or $CF_3$; $R_2$ is $C_1$–$C_3$ alkyl, $C_1$–$C_3$ alkoxy, or $NR_3R_4$; $R_3$ is H or $C_1$–$C_3$ alkyl; $R_4$ is H, $C_1$–$C_3$ alkyl, or $R_5CO$; $R_5$ is H or $C_1$–$C_3$ alkyl; and n is an integer of 0, 1 or 2.

2. A method according to claim 1 wherein said compound is:

4,5-dichloro-2-(3,4-dichlorophenyl)pyrrole-3-carbonitrile;
4,5-dichloro-2-(α,α,α-trifluoro-p-tolyl)pyrrole-3-carbonitrile;
2,3-dichloro-4-nitro-5-(α,α,α-trifluoro-p-tolyl) pyrrole;
2,3-dichloro-5-(3,4-dichlorophenyl)-4-nitropyrrole;
4-bromo-2-(p-chlorophenyl)-5-(trifluoromethyl)pyrrole-3-carbonitrile;
3,4-dibromo-5-(3,4-dichlorophenyl)pyrrole-2-carbonitrile;
2,4-dibromo-5-(p-chlorophenyl)pyrrole-3-carbonitrile;
5-(p-chlorophenyl)pyrrole-2,4-dicarbonitrile;
3-bromo-5-(3,4-dichlorophenyl)pyrrole-2,4-dicarbonitrile;
4,5-dichloro-1-(ethoxymethyl)-2-(α,α,α-trifluoro-p-tolyl)pyrrole-3-carbonitrile;
4-bromo-2-(p-chlorophenyl)-1-(ethoxymethyl)-5-(trifluoromethyl)pyrrole-3-carbonitrile; or
4-bromo-2-(3,4-dichlorophenyl)-5-(trifluoromethyl) pyrrole-3-carbonitrile.

3. A method for controlling insects, nematodes or acarina on infested plants comprising applying to the foliage of said plants or to the soil or water in which said plants are growing, an insecticidally, nematicidally or acaricidally, effective amount of a formula I compound having the structure:

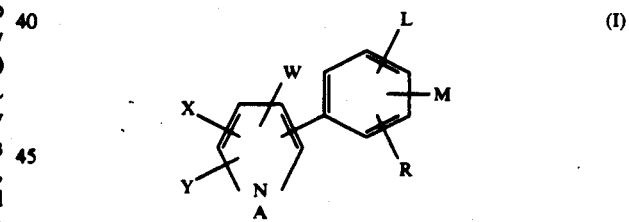

(I)

wherein X is H, F, Cl, Br, I, or $CF_3$; Y is F, Cl, Br, I, $CF_3$ or CN; W is CN or $NO_2$ and A is H; $C_1$–$C_4$ alkyl optionally substituted with from one to three halogen atoms, one hydroxy, one $C_1$–$C_4$ alkoxy, one $C_1$–$C_4$ alkylthio, one phenyl optionally substituted with $C_1$–$C_3$ alkyl, $C_1$–$C_3$ alkoxy or with one to three halogen atoms, one phenoxy optionally substituted with one to three halogen atoms or one benzyloxy optionally substituted with one halogen substituent; $C_1$–$C_4$ carbalkoxymethyl; $C_3$–$C_4$ alkenyl optionally substituted with from one to three halogen atoms; cyano; $C_3$–$C_4$ alkynyl optionally substituted with one halogen; di-($C_1$—$C_4$ alkyl) aminocarbonyl; or $C_4$–$C_6$ cycloalkylaminocarbonyl; L is H, F, Cl or Br; and M and R are each independently H, $C_1$–$C_3$ alkyl, $C_1$–$C_3$ alkoxy, $C_1$–$C_3$ alkylthio, $C_1$–$C_3$ alkylsulfinyl, $C_1$–$C_3$ alkylsulfonyl, cyano, F, Cl, Br, I, nitro, $CF_3$, $R_1CF_2Z$, $R_2CO$ or $NR_3R_4$, and when M and R are on adjacent positions and taken with the carbon atoms to which they are attached they may form a ring in which MR represents the structure:

—OCH$_2$O—, —OCF$_2$O— or 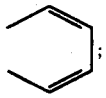;

Z is S(O)n or O; R$_1$ is H, F, CHF$_2$, CHFCl, or CF$_3$; R$_2$ is C$_1$–C$_3$ alkyl, C$_1$–C$_3$ alkoxy, or NR$_3$R$_4$; R$_3$ is H or C$_1$–C$_3$ alkyl; R$_4$ is H, C$_1$–C$_3$ alkyl, or R$_5$CO; R$_5$ is H or C$_1$–C$_3$ alkyl; and n is an integer of 0, 1 or 2.

4. A method according to claim 3 wherein said compound is:

4,5-dichloro-2-(3,4-dichlorophenyl)pyrrole-3-carbonitrile;

4,5-dichloro-2-($\alpha,\alpha,\alpha$-trifluoro-p-tolyl)pyrrole-3-carbonitrile;

2,3-dichloro-4-nitro-5-($\alpha,\alpha,\alpha$-trifluoro-p-tolyl) pyrrole;

2,3-dichloro-5-(3,4-dichlorophenyl)-4-nitropyrrole;

4-bromo-2-(p-chlorophenyl)-5-(trifluoromethyl)pyrrole-3-carbonitrile;

3,4-dibromo-5-(3,4-dichlorophenyl)pyrrole-2-carbonitrile;

2,4-dibromo-5-(p-chlorophenyl)pyrrole-3-carbonitrile;

5-(p-chlorophenyl)pyrrole-2,4-dicarbonitrile;

3-bromo-5-(3,4-dichlorophenyl)pyrrole-2,4-dicarbonitrile;

4,5-dichloro-1-(ethoxymethyl)-2-($\alpha,\alpha,\alpha$-trifluoro-p-tolyl)pyrrole-3-carbonitrile;

4-bromo-2-(p-chlorophenyl)-1-(ethoxymethyl)-5-(trifluoromethyl)pyrrole-3-carbonitrile; or 4-bromo-2-(3,4-dichlorophenyl)-5-(trifluoromethyl) pyrrole-3-carbonitrile.

5. A method according to claim 3 wherein said compound is applied to said plants or the soil in which they are growing, at about 0.125 kg/ha to about 4.0 kg/ha of said formula I compound.

6. A method according to claim 3 wherein said formula I compound is applied to the foliage of said plants to the soil or water in which said plants are growing, in the form of a liquid composition containing from about 10 ppm to about 10,000 ppm of said formula I compound.

* * * * *